(12) United States Patent
Jenkinson et al.

(10) Patent No.: US 9,783,831 B2
(45) Date of Patent: *Oct. 10, 2017

(54) CYCLODEXTRIN GLUCANOTRANSFERASE

(71) Applicant: GREEN BIOLOGICS LTD, Abingdon, Oxfordshire (GB)

(72) Inventors: Elizabeth Jenkinson, Abingdon (GB); Preben Krabben, Didcot (GB); Amanda Harding, Abingdon (GB)

(73) Assignee: GREEN BIOLOGICS LTD, Abingdon, Oxfordshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/436,611

(22) Filed: Feb. 17, 2017

(65) Prior Publication Data

US 2017/0166932 A1    Jun. 15, 2017

Related U.S. Application Data

(63) Continuation of application No. 15/293,189, filed on Oct. 13, 2016, which is a continuation of application No. 14/765,795, filed as application No. PCT/GB2014/050322 on Feb. 5, 2014, now Pat. No. 9,499,804.

(30) Foreign Application Priority Data

Feb. 5, 2013 (GB) .................................. 1302030.0
Feb. 28, 2013 (GB) .................................. 1303595.1

(51) Int. Cl.
| | | |
|---|---|---|
| C12N 9/10 | (2006.01) |
| C12P 7/06 | (2006.01) |
| C12P 7/16 | (2006.01) |
| C12P 7/28 | (2006.01) |
| C12N 15/74 | (2006.01) |
| C12N 15/75 | (2006.01) |

(52) U.S. Cl.
CPC ............ *C12P 7/065* (2013.01); *C12N 9/1074* (2013.01); *C12N 15/74* (2013.01); *C12N 15/75* (2013.01); *C12P 7/16* (2013.01); *C12P 7/28* (2013.01); *C12N 2510/02* (2013.01)

(58) Field of Classification Search
None
See application file for complete search history.

(56) References Cited

U.S. PATENT DOCUMENTS

| | | | |
|---|---|---|---|
| 2,945,786 A | 7/1960 | Motoyoshi |
| 4,536,477 A | 8/1985 | Katkocin et al. |
| 4,578,352 A | 3/1986 | Katkocin et al. |
| 5,501,968 A | 3/1996 | Starnes et al. |
| 5,786,196 A | 7/1998 | Cote |
| 5,888,776 A | 3/1999 | Cote |
| 5,889,179 A | 3/1999 | Cote |
| 2010/0330633 A1 | 12/2010 | Walther et al. |
| 2011/0296747 A1 | 12/2011 | Sonomoto et al. |

FOREIGN PATENT DOCUMENTS

| | | |
|---|---|---|
| EP | 0506790 | 10/1992 |
| EP | 0338057 | 12/1993 |
| EP | 1808497 A1 | 7/2007 |
| WO | WO 88/08031 | 10/1988 |
| WO | WO 89/01043 | 2/1989 |
| WO | WO 89/01044 | 2/1989 |
| WO | WO 89/03421 | 4/1989 |
| WO | WO 91/09962 | 7/1991 |
| WO | WO 99/43793 | 9/1999 |
| WO | WO 2006/035725 | 4/2006 |
| WO | WO 2008/052596 | 5/2008 |

OTHER PUBLICATIONS

Kitahata, et al., Action of Cyclodextrin Glycosyltransferance from Bacillus megaterium Strain No. 5 on Starch, Agr. Biol. Chem., vol. 38(12):2413-2417 (1974).

Al-Shorgani N. et al, "Fermentation of sago starch to biobutanol in a batch culture using Clostridium saccharoperbutylacetonicum N1-4 (ATCC 13564)"; Annals of Microbiology, vol. 62, No. 3, p. 1059-1070, Sep. 2012.

Ayaaki, Ishizaki et al., Extractive acetone-butanol-ethanol fermentation using methylated crude palm oil as extractant in batch culture of Clostridium saccaroperbutylacetonicum N1-4 (ATCC 13564); Journal of Bioscience and Bioengineering, vol. 87, No. 3, p. 352-356, Jan. 1999.

Cheng, CL et al., Bioresource Technology, vol. 113, 2012; "High yield bio-butanol production by solvent-producing bacterial microflora", 58-64.

C Cheng, J. et al., "High-level extracellular production of α-cyclodextrin glycosyltransferase with recombinant *Escherichia coli* BL21 (DE3)" J. Agric. Food Chem., vol. 59, pp. 3797-3802 (2011).

Chojeck, A. & Blaschek, H.P, "Effect of carbohydrate source on alpha-amylase and glucoamylase formation by Clostridium acetobutylicum SA1." J. Ind. Microbiol., 1, 63-67.1986.

Collins et al., Int. J. Syst. Bacteriol. (Oct. 1994), pp. 812-826.

Green, Edward M., Fermentative production of butanol the industrial perspective, Current Opinion in Biotechnology, vol. 22, No. 4, Mar. 1, 2011, pp. 337-343.

Hongo, M. et al., Bacterio phages of clostridium-saccaroperbutylacetonicum Part 16 isolation and some characters of a temperate phage; Agricultural and Biological Chemistry, vol. 33, No. 3, p. 337-342, 1969.

Keis, Stefanie et al., "Emended descriptions of *Clostridium acetobutylicum* and *Clostridium beijerinckii* and descriptions of *Clostridium saccharoperbutylacetonicum* sp. nov. and *Clostridium saccarobutylicum* sp. nov"; Int. J. of Systematic and Evolutionary Microbiology, Society for General Microbiology, Reading GB; vol. 51, No. 6, p. 2095-2103, Nov. 2001.

(Continued)

*Primary Examiner* — Suzanne M Noakes
(74) *Attorney, Agent, or Firm* — Knobbe Martens Olson & Bear LLP

(57) ABSTRACT

The present invention relates to a novel cyclodextrin glucanotransferase (CGTase) enzyme which is obtainable from *Clostridium saccharoperbutylacetonicum* N1-4, N1-4 (HMT) or N1-504. The invention further relates to nucleic acids encoding the enzyme, vectors and host cells, and uses of the CGTase.

18 Claims, 19 Drawing Sheets

(56) References Cited

OTHER PUBLICATIONS

Madihah, M.S. et al., "Partial purification and some properties of α-amylase and glucoamylase obtained as by-product from direct fermentation of sago starch to solvent by Clostridium acetobutylicum." Pak. J. Bio. Sci. 3(5), 744-749. 2000.
Martin Del Valle, E.M.; Cyclodextrin and their uses: a review, Process Biochemistry, vol. 39, No. 9, May 1, 2004, pp. 1033-5113.
Paquet et al., "Purification and characterization of the extracellular alpha-amylase from Clostridium acetobutylicum ATCC 824." Appl. Environ. Microbiol., 57(1), 212-8. 1991.
Poelein, A. & Daniel R., "Glycosidase" XP002723857; Database Accession No. M1MLV9 (M1MLV9_9CLOT); Database—UniProt (Online); Feb. 2013.
Poelein, A. & Daniel R., "Genome sequence of Clostridium saccharoperbutylacetonicum N1-4(HMT)", XP002723858; Database Accession No. CP004121; Database—GenBank (Online); Jan. 2014.
Sandoval-Espinola et al., "Comparative phenotypic analysis and genome sequence of Clostridium beijerinckii SA-1, an offspring of NCIMB 8052." Microbiology. Sep. 25, 2013.
Slominska, L., Starch, vol. 49, 1997, "Studies on cyclodextrin synthesis . . . ", pp. 301-305.
Soni, B.K. et al., "Inhibitory factors involved in acetone-butanol fermentation by clostridium-saccaroperbutylacetonicum"; Current Microbiology, vol. 16, No. 2, p. 61-68, 1987.
Tashiro, Y. et al., J Bioscience & Bioengineering, vol. 98, 2004; "High butanol production by Clostridium saccharoperbutylacetonicum N 1-4 in fed-batch culture", 263-268.
Thang V. H. et al., "Production of Acetone-Butanol-Ethanol (ABE) in Direct Fermentation of Cassava by Clostricium saccharoperbutylacetonicum N1-4"; Applied Biochemistry and Biotechnology, vol. 161, No. (1-8), p. 157-170, May 2010.
Watanabe, H. et al., Biosci. Biotechnol. Biochem., vol. 70, 2006, "Cloning, sequencing and expression of the genes encoding an lsocyclomaltooligosaccharide Glucanotransferase and an a-Amylase from a Bacillus circulans strain", Biosci. Biotechnol. Biochem., vol. 70, Iss. 11, pp. 2690-2702, 2006.
Alsaker and Papoutsakis, J. Bacteriol. 187 (7103-7118). (2005).
Al-Shorgani, Biotechnology (2011) 10(3) 280-285.
Altschul et al., "Gapped BLAST and PSI-BLAST: a new generation of protein database search programs"; Nucleic Acids Res. 25:3389-3402; 1997.
Bahl, H., "alpha-Amylase of Clostridium thermosulfurogenes EM1: nucleotide sequence of the gene, processing of the enzyme, and comparison of other alpha-amylases." Appl. Environ. Microbiol., 57(5), 1554-9. 1991.
Bergy, "Bergey's Manual of Systematic Bacteriology: vol. 3: The Firmicutes: Revised road map to the phylum Firmicutes" (2009) edited by Paul Vos, George Garrity, Dorothy Jones, Noel R. Krieg, Wolfgang Ludwig, Fred A. Rainey, Karl-Heinz Schleifer, William Whitman—entry # 133 (p. 809-810) http://www.bergeys.org/outlines/bergeys_vol_3_roadmap_outline.pdf.
Dayhoff et al., "Atlas of Protein Sequence and Structure" (Nat'l. Biomed. Res. Found., Washington, D.C.); 1978.
Del Cerro, Genome Announc 1 (2), E00070-13 (2013).
Euzéby, J.P., (1997). "List of Bacterial Names with Standing in Nomenclature: a folder available on the Internet". Int J Syst Bacteriol 47 (2): 590-2. doi:10.1099/00207713-47-2-590. ISSN 0020-7713. PMID 9103655.].
Ha et al., Proc Natl Acad Sci U S A. Jan. 11, 2011; 108(2): 504-509. Published online Dec. 27, 2010. doi: 0.1073/pnas.1010456108 "Engineered Saccharomyces cerevisiae capable of simultaneous cellobiose and xylose fermentation."
Hyun-Dong, Site-directed mutagenesis and functional analysis of maltose-binding site of B-cyclodextrin glucanotransferase from Bacillus firmus var. Alkalophilus Biotechnology Letters 22, 115-121, 2000.
Jang, Bioresource Technology xxx (2012) xxx-xxx "Butanol production from renewable biomass by clostridia".
Jones and Woods, Microbiological Reviews, 50:484-524;1986.
Knegtel, R.M., Crystal structure at 2.3 A resolution and revised nucleotide sequence of the thermostable cyclodextrin glycosyltransferase from Thermonanaerobacterium thermosulfurigenes EM1. J. Mol. Biol., 256(3), 611-22. 1996.
Kosaka, Biosci. Biotechnol. Biochem. (2007) 71(1), 58-68.
Lima, Applied Biochemistry and Biotechnology (1998), vol. 70-72, 789-804.
Ma et al., Bioinformatics. Mar; 18(3): 440-5; 2002.
Martin et al., Biocatalysis and Biotransformation (2001) vol. 19, pp. 21-23.
E.M. Martin El Valle., "Cyclodextrins and their uses: a review." Process Biochemistry Jul. 2, 2003, 14 pages.
Matuschek, M., Pullulanase of Thermoanaerobacterium thermosulfurigenes EM1 (Clostridiumthermosulfurogenes): molecular analysis of the gene, composite structure of the enzyme, and a common model for its attachment to the cell surface. J. Bacteriol., 176(11), 3295-302. 1994.
Mori, J. Appl. Glycosci (2011) 58, 39-46.
Poehlein et al., "Complete Genome Sequence of the Solvent Producer Clostridium saccharoperbutylacetonicum Strain DSM 14923", Genome Announcements, vol. 2 Sep. 2014, 2 pages.
Sahm, K., Molecular analysis of the amy gene locus of Thermoanaerobacterium thermosulfurigenes EM1 encoding starch-degrading enzymes and a binding protein-dependent maltose transport system.. J Bacteriol., 178(4), 1039-46. (1996).
Soni, Biotechnology and Bioengineering Symposium No. 17 (1986) pp. 591-603.
Soni, Biotechnology Letters (1982) vol. 4, 1, 19-22.
Stackebrandt et al., "Phylogenetic basis for a taxonomic dissection of the genus Clostridium"; FEMS Immunol. Med. Microbiol., 24(3), p. 253-8, 1999.
Taguchi, F. "Effect of amylase accumulation on hydrogen production by Clostridium beijerinckii, strain AM21B." Journal of Fermentation and Bioengineering, 77(5), 565-567. 1994.
Thang, V.H., Production of Acetone-Butanol-Ethanol (ABE) in Direct Fermentation of Cassava by Clostridium saccharoperbutylacetonicum N14. Appl. Biochem. Biotechnol., Sep. 22, 2009.
Thang, V.H., & Kobayashi, G., "A Novel Process for Direct Production of Acetone-Butanol-Ethanol from Native Starches Using Granular Starch Hydrolyzing Enzyme by Clostridium saccharoperbutylacetonicum N1-4." Appl Biochem Biotechnol. Nov. 26, 2013. [Epub ahead of print].
Watanabe, J. Appl. Glycosci. (2007) 54, 109-118.
Wind, R.D., Cyclodextrin formation by the thermostable alpha-amylase of Thermoanaerobacterium thermosulfurigenes EM1 and reclassification of the enzyme as a cyclodextrin glycosyltransferase. Appl Environ Microbiol., 61(4), 1257-65. 1995.
Wind, R.D., Engineering of factors determining alpha-amylase and cyclodextrin glycosyltransferase Specificity in the cyclodextrin glycosyltransferase from Thermoanaerobacterium thermosulfurigenes EM1. Eur. J. Biochem., 253(3), 598-605. 1998.
Wind, R.D., Engineering of cyclodextrin product specificity and pH optima of the thermostable cyclodextrin glycosyltransferase from Thermoanaerobacterium thermosulfurigenes EM1. J. Biol. Chem., 273(10), 5771-9. 1998.
Hillman et al., PerR acts as a switch for oxygen tolerance in the strict anaerobe Clostridium acetobutylicum, Molecular Microbiology (2008) 68(4), 848-860.

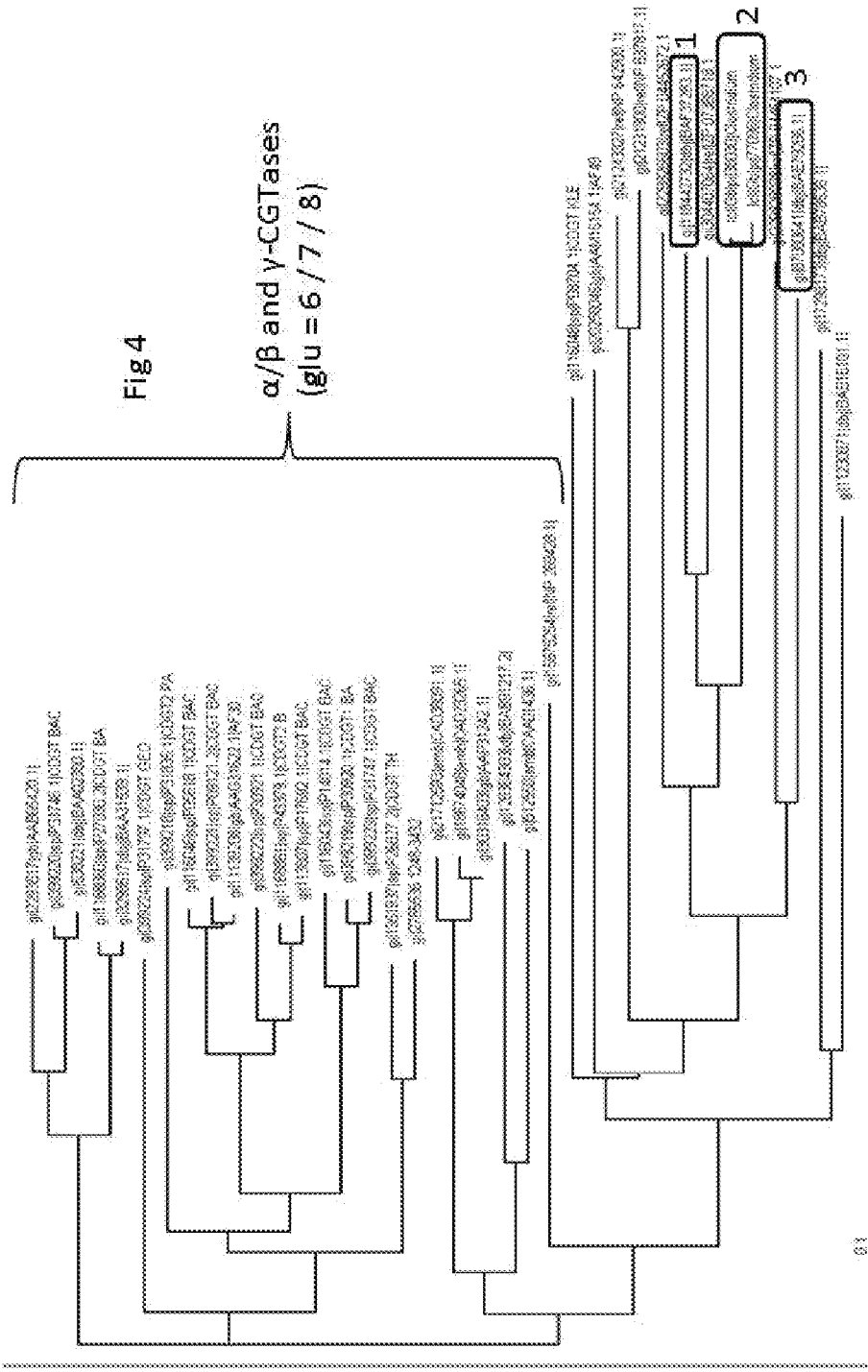

Figure 5

```
 1   gi|399220|sp|P  GTDFSSYEDSIY---------RNLYDLADYDLNNTVMDQYLKESI-KFWLDKGIDGIRVD
 2   gi|538221|dbj|  GTDFSSYEDSIY---------RNLYDLADYDLNNTVMDQYLKESI-KFWLDKGIDGIRVD
 3   gi|2293517|gb|  GTDFSSYEDSIY---------RNLYDLADYDLNNKVVDQYLKESI-KLWLIK-IDGIRVD
 4   gi|1168860|sp|  GTDFSSYEDSIY---------RNLYDLADYDLNNTVMDQYLKESI-KLWLDKGIDGIRVD
 5   gi|3298517|dbj  GTDFSSYEDSIY---------RNLYDLADYDLNNTVMDQYLKESI-KLWLDKGIDGIRVD
 6   gi|399221|sp|P  GTDFSIIENGIY---------KNLYDLADLNHNNSSVDVYLKDAI-KQMWLDLGVDGIRVD
 7   gi|11139208|gb  GTDFSIIENGIY---------KNLYDLADLNHNNSSVDVYLKDAI-KQMWLDLGVDGIRVD
 8   gi|116046|sp|P  GTDFSIIENGIY---------KNLYDLADLNHNNSSVDVYLKDAI-KQMWLDLGVDGIRVD
 9   gi|1168861|sp|  GTDFSTTENGIY---------KNLYDLADLNHNNSTVDVYLKDAI-KQMWLDLGIDGIRMD
10   gi|113807|sp|P  GTDFSTTENGIY---------KNLYDLADLNHNNSTSDVYLKDAI-KQMWLDLGIDGIRMD
11   gi|399222|sp|P  GTDFSTTENGIY---------KNLYDLADLNHNNSTVDTYLKDAI-KQMWLDLGIDGIRMD
12   gi|399219|sp|P  GSDFSSLENGIY---------KNLYDLADFNHNNATIDKYFKDAI-KLWLDMGVDGIRVD
13   gi|399223|sp|P  GSDFSSLENGIY---------KNLYDLADFNHNNATIDKYFKDAI-KLWLDMGVDGIRVD
14   gi|116043|sp|P  GSDFSTLENGIY---------KNLYDLADLNHNNSTIDTYFKDAI-KLWLDMGVDGIRVD
15   gi|399218|sp|P  GTDFSTTESGIY---------KNLYDLADINQNHNTIDSYLKESI-QLWLNLGVDGIRFD
16   gi|1351937|sp|  GTDFSSYEDGIY---------RNLFDLADLNQQNSTIDSYLKSAI-KVWLDMGIDGIRLD
17   gi|2765536|Tre  GTNFSSYEDGIY---------RNLFDLADLDQQNSTIDSYLKAAI-KLWLDMGIDGIRMD
18   gi|399224|sp|P  GTTFSSLEDGIY---------RNLFDLADLNHQNPVIDRYLKDAV-KMWIDMGIDGIRMD
19   gi|18674048|em  GTDFSNYEDEIY---------RNLFDLASFNHINSELNNYLEDAV-KKWLDLGIDGIRID
20   gi|30316403|gb  GTDFSNYEDEIY---------RNLFDLASFNHINSELNNYLEDAV-KKWLDLGIDGIRID
21   gi|21712593|em  GTDFSTYEDEIY---------RNLFDLASFNHINAELNNYLEDAV-KKWLDLGIDGIRID
22   gi|126364303|d  GSDFSDYENSIY---------RNLYDLASLNQQHSFIDKYLKESI-QLWLDTGIDGIRVD
23   gi|512550|emb|  GSDFSSYEDSIY---------RNLYDLASLNQQHSFIDRYLKESI-QMWLDLGIDGIRVD
24   gi|15675254|re  WTDFSTYENSIY---------HSMYGLADLNNNINPKVDQYMKEAI-DKWLDLGVDGIRVD
25   gi|17298173|db  IYTWSG-IPLKY---------ANLYGLADFNQLNPWVDSYLIEGA-MLFVDSGACGLRID
26   gi|11230871|db  ITNWNDRWEVRY---------KNLFNLADLNQLNPWVDNYLKEST-VSYLEAGIGGIRID
27   gi|116048|sp|P  VTNWNDFFQVKN---------HNLFNLSDLNQSNTDVYQYLLDGS-KFWIDAGVDAIRID
28   gi|20258046|gb  VQNWEDEWQVQN---------CELAGLATFNENNSDYRQYIKSAI-KQWLDRGVDALRVD
29   gi|118442732|d  DINWSLADGRYDQWAQDYLENHDLGGLDDIDFDVPAAKQAIFSSIKGWFDYTGADGARVD
30   gi|304407064|r  DINWSLVDGSYIAATQDYLENHDLAGLDDIDFDNAQAKQAMFDSIKGWFDYTGADGARVD
31   lcl|GBLpi|3803  DIDWSREHS-----DPQMLDDHDLGGLDDLNQDNSDAKAAMNNAIKSWFDYTGADAARVD
32   lcl|GBLpi|7709  DIDWSREHS-----DPQMLDDHDLGGLDDLNQDNSDAK-AMNNAIKSWFDYTGADAARVD
33   gi|229828603|r  DIDWNKEFPR-TAESIQMMEDHDLSMLDDIDYDVPEAKQAMLEAMKNWYNYTGADGARID
34   gi|87080641|db  DCLFNGLET------QTQIENCDLGGLDDLDQSNPVVSSHLMSTYKDWV-DMGFDGIRVD
35   gi|381398655|r  DCLFNGTET------QTQIENCDLGGLDDLDQSNPTVSNYLINTYKDWV-DMGFDGIRVD
36   gi|283783751|r  DCKFDNTES------QSDIEQCDLGGLDDLDQSNPQVSKYLIKTYKDWI-DMGFDGMRVD
37   gi|298252508|r  DCKFDNTES------QSDIEQCDLGGLDDLDQSNPQVSKYLIKTYKDWI-DMGFDGMRVD
38   gi|229828038|r  D--IDDWNN------ENQVLNYDLGGLDDLDQSNPEARKAIEDAYYQWVHDTGADGVRID
39   gi|21243327|re  HNPLHAFYNTGG----------GLAELSDLNENNPAVLDYLAGAY-LQWMEQGADAFRID
40   gi|21231900|re  HNPLHAFYNTSG----------GLAELSDLNEDNPAVLDYLAGAY-LQWMEQGADAFRID
41   gi|157834520|p  ITDWDNLTMVEDCWEG-----DTIVSLPDLDTTEIAVRTIWYDWVADLVSNYSVDGLRID ruler            90·······300·······310·······320·······330·······340·······3
```

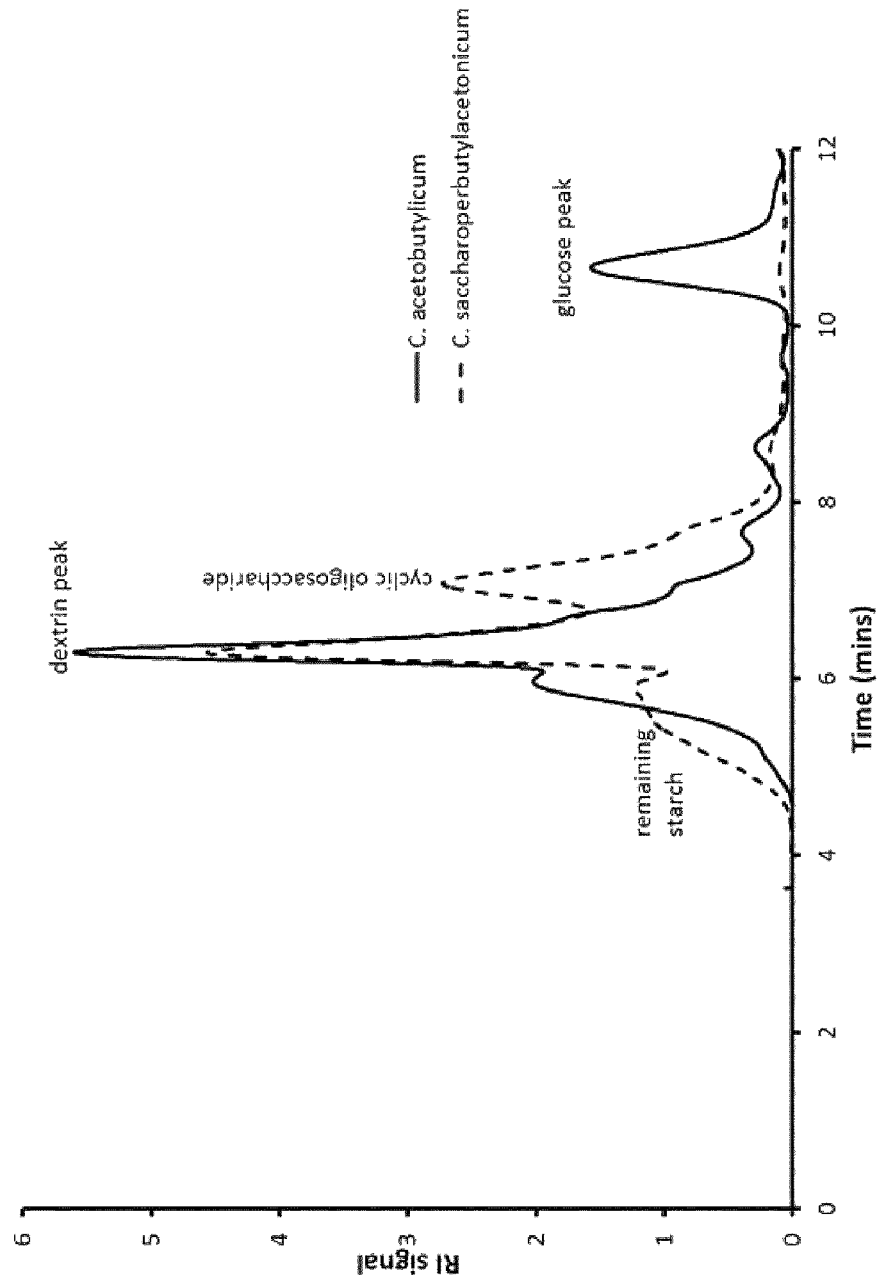

SEQUENCE LISTING

<160> NUMBER OF SEQ ID NOS: 55

<210> SEQ ID NO 1
<211> LENGTH: 674
<212> TYPE: PRT
<213> ORGANISM: Clostridium saccharoperbutylacetonicum

<400> SEQUENCE: 1

```
Met Phe Arg Arg Lys Phe Asn Lys Val Ile Leu Ser Ile Leu Val Ala
1               5                   10                  15

Thr Ile Val Ser Ser Thr Asn Met Phe Met Ser Gly Ser Lys Ala Gln
            20                  25                  30

Ala Ala Ile Gly Asn Leu Ser Glu Asn Asp Thr Ile Tyr Gln Ile Met
            35                  40                  45

Val Asp Arg Phe Tyr Asp Gly Asp Lys Thr Asn Asn Ala Thr Gly Asp
        50                  55                  60

Ala Phe Arg Asn Thr Glu Asn Leu Glu Asp Asp Phe Arg Tyr Met His
65                  70                  75                  80

Gly Gly Asp Trp Gln Gly Val Ile Asp Lys Leu Asp Tyr Ile Lys Gly
                85                  90                  95

Met Gly Tyr Ser Ala Ile Trp Ile Ser Pro Val Ala Glu Pro Gln Met
            100                 105                 110

Trp Ser Arg Ala Asp Gly Thr Gly Lys Val Trp Pro Thr Ala Tyr His
        115                 120                 125

Gly Tyr Asn Val Lys Asp Pro Asn Lys Ala Asn Pro Tyr Phe Gly Thr
    130                 135                 140

Lys Glu Lys Leu Lys Glu Leu Val Asp Lys Ala His Glu Lys Gly Ile
145                 150                 155                 160

Lys Val Ile Ile Asp Ile Val Pro Asn His Val Gly Asp Tyr Met Leu
                165                 170                 175

Gly Lys Gln Ala Tyr Tyr Asp Ile Lys Gly Phe Glu Pro Ala Ala Pro
            180                 185                 190

Phe Asn Asn Pro Asn Trp Tyr His His Asn Gly Asp Ile Asp Trp Ser
        195                 200                 205

Arg Glu His Ser Asp Pro Gln Met Leu Asp Asp His Asp Leu Gly Gly
    210                 215                 220
```

-continued

Leu Asp Asp Leu Asn Gln Asp Asn Ser Asp Ala Lys Ala Ala Met Asn
225                 230                 235                 240

Asn Ala Ile Lys Ser Trp Phe Asp Tyr Thr Gly Ala Asp Ala Ala Arg
            245                 250                 255

Val Asp Ala Ala Lys Cys Met Lys Pro Ser Tyr Ile Asn Glu Leu Gln
        260                 265                 270

Lys Tyr Ile Gly Val Asn Thr Phe Gly Glu Asn Phe Asp Met Asn Val
    275                 280                 285

Asp Phe Val Lys Lys Trp Val Gly Ser Asp Ala Glu Trp Gly Met Leu
290                 295                 300

Asp Phe Pro Leu Tyr Gln Ala Ile Asn Asn Asp Phe Ala Ser Gly Gln
305                 310                 315                 320

Ser Phe Asp Asp Met Ser Ser Ser Gly Thr Cys Ser Ile Lys Asn Ile
                325                 330                 335

Leu Ala Gln Asp Asn Lys Tyr Asn Gly Tyr Ala Asn His Met Val Thr
                340                 345                 350

Phe Ile Asp Asn His Asp Arg Asn Arg Phe Leu Thr Val Ala Asn Gly
            355                 360                 365

Asn Val Lys Lys Leu Gln Asn Ala Leu Val Phe Met Phe Thr Val Arg
370                 375                 380

Gly Val Pro Thr Val Phe Gln Gly Thr Glu Gln Asn Lys Gly Asn Ala
385                 390                 395                 400

Asn Gly Ala Ser Ile Asn Gly Ile Ala Asp Thr Trp Asn Arg Trp Ser
                405                 410                 415

Met Val Lys Lys Asp Tyr Asn Gly Asn Val Ile Thr Asp Tyr Phe Asn
                420                 425                 430

Glu Asn Thr Asp Thr Tyr Lys Leu Ile Asn Lys Leu Asn Ser Phe Arg
            435                 440                 445

Gln Lys Tyr Glu Ala Leu Arg Glu Gly Thr Gln Arg Glu Met Trp Ser
450                 455                 460

Ser Pro His Leu Tyr Ala Phe Ser Arg Arg Met Asp Ser Gly Glu Asn
465                 470                 475                 480

Val Gly Gln Glu Val Val Asn Val Phe Asn Asn Ser Asp Gly Asp Gln
                485                 490                 495

Ser Ala Thr Ile Pro Ile Arg Ala Glu Ser Thr Ile Lys Val Gly Asp
                500                 505                 510

Lys Phe Val Asn Leu Phe Asp Val Asn Asp Ser Ile Thr Val Gln Gln
            515                 520                 525

Gly Gly Val Thr Gly Lys Gln Ile Ser Val Asn Leu Gly Glu Asn Ser
530                 535                 540

Gly Lys Ile Tyr Val Val Asn Asn Glu Thr Pro Asn Pro Asp Gln Lys
545                 550                 555                 560

Asn Val Gln Tyr Lys Val Ser Tyr Lys Asn Thr Asn Ala Gln Lys Val
                565                 570                 575

Thr Leu His Tyr Gly Thr Asn Gly Trp Lys Asn Ile Gln Asp Val Asn
                580                 585                 590

Met Thr Lys Asn Ser Asn Gly Glu Phe Glu Ala Thr Ile Thr Val Asn
            595                 600                 605

Asn Asn Asp Ile Leu Asn Tyr Cys Ile His Ile Ile Ser Pro Thr Asp
            610                 615                 620

Tyr Trp Asp Asn Asn Gly Gly Gln Asn Trp Asn Val Lys Val Thr Lys
625                 630                 635                 640

Ala Glu Asp Tyr Ile Asn Asp Gly Val Lys Ser Asn Leu Lys Ser Val
            645                 650                 655

Asn Thr Thr Thr Ser Ala Ala Ile Asp Ser Gly Ile Asp Ser Thr Val
            660                 665                 670

Asn Arg

<210> SEQ ID NO 2
<211> LENGTH: 2025
<212> TYPE: DNA
<213> ORGANISM: Clostridium saccharoperbutylacetonicum

<400> SEQUENCE: 2

| | | | | | |
|---|---|---|---|---|---|
| atgtttagaa | gaaaatttaa | caaggtaata | ttatctatct | tagttgcaac | aattgtttca | 60 |
| agcactaaca | tgtttatgag | tggaagcaag | gcacaagcgg | caattggaaa | tctaagtgaa | 120 |
| aacgatacta | tttatcaaat | tatggtagac | agattttatg | atggagataa | aacaaataat | 180 |
| gctacaggag | atgcatttcg | taatacagaa | atcttgaag | atgattttag | atatatgcac | 240 |
| ggcggagatt | ggcaaggtgt | tattgataag | ttagattata | ttaagggcat | gggatactca | 300 |
| gccatttgga | tatcaccggt | tgcggaacca | caaatgtggt | ctagagctga | tggcacagga | 360 |
| aaagtatggc | ctacagctta | tcatggatat | aatgtgaaag | atcccaataa | ggcaaatcct | 420 |
| tattttggaa | caaagaaaa | gctaaaggag | ttagtagata | agctcacga | aaagggatt | 480 |
| aaagtaataa | tagatatagt | tccaaatcat | gttggggatt | atatgttagg | aaaacaagct | 540 |
| tattatgaca | tcaaggggtt | tgagccggca | gcaccttta | ataatccaaa | ttggtatcat | 600 |
| cataatggcg | atattgattg | gtcaagagaa | cactctgatc | cccaaatgtt | agatgatcat | 660 |
| gatttgggcg | gtttagatga | tttaaatcaa | gataattctg | atgctaaggc | agctatgaat | 720 |
| aatgctatta | gtcatggtt | tgattatact | ggagctgatg | cagcaagggt | tgacgcagca | 780 |
| aaatgtatga | aaccatctta | tattaacgag | ttacaaaagt | atataggagt | taatactttt | 840 |
| ggagaaaatt | ttgatatgaa | tgtagatttt | gtgaagaagt | gggttggatc | cgatgcagaa | 900 |
| tggggaatgc | tagattttcc | attatatcaa | gcaataaata | tgatttttgc | atcaggacaa | 960 |
| tcttttgatg | acatgtcatc | atcaggtact | tgctctatta | aaaatatttt | agcacaagac | 1020 |
| aataaatata | atggttatgc | aaatcatatg | gtgacttta | tagataatca | tgatcgtaat | 1080 |
| agatttttaa | cagtagcaaa | tggtaatgta | aaaaaacttc | aaaatgcact | tgttttcatg | 1140 |
| tttactgtaa | gagggtacc | aacagtatt | caaggtacag | aacaaaacaa | aggtaatgca | 1200 |
| aatggagcaa | gtataaatgg | tattgcagat | acatggaatc | gttggtcaat | ggttaaaaag | 1260 |
| gattacaatg | gaaatgtaat | tacagattat | tttaatgaga | atacagatac | ttataaacta | 1320 |
| attaacaaat | tgaattcatt | taggcaaaaa | tatgaagcct | taagagaagg | tactcaaaga | 1380 |
| gaaatgtggt | cttcaccaca | tttatatgca | ttctcaagaa | ggatggattc | aggagaaaat | 1440 |
| gttggacaag | aagttgtaaa | tgtatttaat | aattcagatg | gagatcaaag | tgcgaccatt | 1500 |
| ccaattagag | ctgaaagtac | tataaaagtt | ggagataaat | ttgtaaatct | ttttgatgta | 1560 |
| aatgattcga | tcacagttca | acaaggaggt | gttacaggaa | acaaatatc | agtgaattta | 1620 |
| ggagaaaata | gtgggaagat | ttatgttgtt | aataatgaaa | caccaaatcc | agatcaaaag | 1680 |
| aacgtacaat | ataaagtttc | ataaagaat | actaatgcac | aaaaagtaac | acttcattat | 1740 |
| ggaactaatg | gatggaaaaa | cattcaagat | gtaaatatga | ctaagaattc | caatggagaa | 1800 |
| tttgaagcaa | ctattacagt | aaataataat | gatattctaa | attactgtat | tcatattatt | 1860 |
| tcaccaacag | actattggga | taataatggt | ggacagaatt | ggaatgtaaa | agtgactaag | 1920 |

-continued

```
gcagaagatt atataaatga tggtgtaaag agtaatttga agagcgttaa tacaactaca    1980
tcagcagcta tagactctgg gattgatagt actgtaaatc gttaa                    2025
```

<210> SEQ ID NO 3
<211> LENGTH: 674
<212> TYPE: PRT
<213> ORGANISM: Clostridium saccharoperbutylacetonicum

<400> SEQUENCE: 3

```
Met Phe Arg Arg Lys Phe Asn Lys Val Ile Leu Ser Ile Leu Val Ala
1               5                   10                  15

Thr Ile Val Ser Ser Thr Asn Met Phe Met Ser Gly Ser Lys Ala Gln
            20                  25                  30

Ala Ala Ile Gly Asn Leu Ser Glu Asn Asp Thr Ile Tyr Gln Ile Met
        35                  40                  45

Val Asp Arg Phe Tyr Asp Gly Asp Lys Thr Asn Asn Ala Thr Gly Asp
    50                  55                  60

Ala Phe Arg Asn Thr Glu Asn Leu Glu Asp Asp Phe Arg Tyr Met His
65                  70                  75                  80

Gly Gly Asp Trp Gln Gly Val Ile Asp Lys Leu Asp Tyr Ile Lys Gly
                85                  90                  95

Met Gly Tyr Ser Ala Ile Trp Ile Ser Pro Val Ala Glu Pro Gln Met
            100                 105                 110

Trp Ser Arg Ala Asp Gly Thr Gly Lys Val Trp Pro Thr Ala Tyr His
        115                 120                 125

Gly Tyr Asn Val Lys Asp Pro Asn Lys Ala Asn Pro Tyr Phe Gly Thr
    130                 135                 140

Lys Glu Lys Leu Lys Glu Leu Val Asp Lys Ala His Glu Lys Gly Ile
145                 150                 155                 160

Lys Val Ile Ile Asp Ile Val Pro Asn His Val Gly Asp Tyr Met Leu
                165                 170                 175

Gly Lys Gln Ala Tyr Tyr Asp Ile Lys Gly Phe Glu Pro Ala Ala Pro
            180                 185                 190

Phe Asn Asn Pro Asn Trp Tyr His His Asn Gly Asp Ile Asp Trp Ser
        195                 200                 205

Arg Glu His Ser Asp Pro Gln Met Leu Asp Asp His Asp Leu Gly Gly
    210                 215                 220

Leu Asp Asp Leu Asn Gln Asp Asn Ser Asp Ala Lys Ala Ala Met Asn
225                 230                 235                 240

Asn Ala Ile Lys Ser Trp Phe Asp Tyr Thr Gly Ala Asp Ala Ala Arg
                245                 250                 255

Val Asp Ala Ala Lys Cys Met Lys Pro Ser Tyr Ile Asn Glu Leu Gln
            260                 265                 270

Lys Tyr Ile Gly Val Asn Thr Phe Gly Glu Asn Phe Asp Met Asn Val
        275                 280                 285

Asp Phe Val Lys Lys Trp Val Gly Ser Asp Ala Glu Trp Gly Met Leu
    290                 295                 300

Asp Phe Pro Leu Tyr Gln Ala Ile Asn Asn Asp Phe Ala Ser Gly Gln
305                 310                 315                 320

Ser Phe Asp Asp Met Ser Ser Ser Gly Thr Cys Ser Ile Lys Asn Ile
                325                 330                 335

Leu Ala Gln Asp Asn Lys Tyr Asn Gly Tyr Ala Asn His Met Val Thr
            340                 345                 350
```

Phe Ile Asp Asn His Asp Arg Asn Arg Phe Leu Thr Val Ala Asn Gly
355                 360                 365

Asn Val Lys Lys Leu Gln Asn Ala Leu Val Phe Met Phe Thr Val Arg
    370                 375                 380

Gly Val Pro Thr Val Phe Gln Gly Thr Glu Gln Asn Lys Gly Asn Gly
385                 390                 395                 400

Asn Gly Ala Ile Leu Asn Gly Ile Ala Asp Thr Trp Asn Arg Trp Ser
                405                 410                 415

Met Val Lys Lys Asp Tyr Asn Gly Asn Ile Ile Thr Asp Tyr Phe Asn
            420                 425                 430

Glu Asn Thr Asp Thr Tyr Lys Leu Ile Ser Lys Leu Asn Ser Phe Arg
        435                 440                 445

Gln Lys Tyr Glu Ala Leu Arg Glu Gly Thr Gln Arg Glu Met Trp Ser
    450                 455                 460

Ser Pro His Leu Tyr Ala Phe Ser Arg Arg Met Asp Ser Gly Glu Asn
465                 470                 475                 480

Val Gly Gln Glu Val Val Asn Val Phe Asn Asn Ser Asp Gly Asp Gln
                485                 490                 495

Ser Ala Thr Ile Pro Ile Arg Ala Glu Ser Thr Ile Lys Val Gly Asp
            500                 505                 510

Lys Leu Val Asn Leu Phe Asp Val Asn Asp Ser Ile Thr Val Gln Gln
        515                 520                 525

Gly Gly Val Thr Gly Lys Gln Ile Ser Val Asn Leu Gly Glu Asn Ser
    530                 535                 540

Gly Lys Ile Tyr Val Val Asn Asn Glu Thr Pro Asn Pro Asp Gln Lys
545                 550                 555                 560

Asn Val Gln Tyr Lys Val Ser Tyr Lys Asn Thr Asn Ala Gln Lys Val
                565                 570                 575

Thr Leu His Tyr Gly Thr Asn Gly Trp Lys Asn Ile Gln Asp Val Asn
            580                 585                 590

Met Thr Lys Asn Ser Asn Gly Glu Phe Glu Ala Thr Ile Thr Val Asn
        595                 600                 605

Asn Asn Asp Ile Leu Asn Tyr Cys Ile His Ile Ser Pro Thr Asp
    610                 615                 620

Tyr Trp Asp Asn Asn Gly Gly Gln Asn Trp Asn Val Lys Val Thr Lys
625                 630                 635                 640

Ala Glu Asp Tyr Ile Asn Asp Gly Val Lys Ser Asn Leu Lys Ser Val
                645                 650                 655

Asn Thr Thr Thr Ser Ala Ala Ile Glu Ser Gly Ile Asp Ser Thr Val
            660                 665                 670

Asn Arg

<210> SEQ ID NO 4
<211> LENGTH: 2025
<212> TYPE: DNA
<213> ORGANISM: Clostridium saccharoperbutylacetonicum

<400> SEQUENCE: 4
atgtttagaa gaaaatttaa caaggtaata ttatctattt tagttgcaac aattgtttca      60
agcactaaca tgtttatgag tggaagcaag gcacaagcgg caattggaaa tttaagtgaa     120
aacgatacta tttatcaaat tatggtagac agatttatg atggagataa aacaaataat     180
gctacaggag atgcatttcg taatacagaa atcttgaag atgatttag atatatgcac     240 ggcggagatt ggcaaggtgt tattgataag ttagattata ttaagggcat gggatactca     300

```
gccatttgga tatcaccggt tgcggaacca caaatgtggt ctagagctga tggcacagga      360
aaagtatggc ctacagctta ccatggatat aatgtgaaag atcccaataa ggcaaatcct      420
tattttggaa caaaagaaaa gctaaaggag ttagtagata agctcacga aaaggggatt       480 aaagtaataa tagatatagt tccaaatcat gttgggggatt atatgttagg aaaacaagct     540
tattatgaca tcaaggggtt tgagccggca gcacctttta ataatccaaa ttggtatcat      600
cataatggcg atattgattg gtcaagagaa cactctgatc cccaaatgtt agatgatcat      660
gatttgggcg gtttagatga tttaaatcaa gataattctg atgctaaggc agctatgaat      720
aatgctatta agtcatggtt tgattatact ggagctgatg cagcaagggt tgacgcagca      780
aaatgtatga aaccatctta tattaacgag ttacaaaagt atataggagt taatactttt      840
ggagaaaatt ttgatatgaa tgtagatttt gtgaagaagt gggttggatc cgatgcagaa      900
tggggaatgc tagattttcc attatatcaa gcaataaata atgatttgc atcaggacaa       960 tcttttgatg acatgtcatc atcaggtact tgctctatta aaatatttt agcacaagac      1020 aataaatata atggttatgc aaatcatatg gtgactttta tagataatca tgatcgtaat     1080 agattttaa cagtagcaaa tggtaatgtt aaaaaacttc aaaatgcact tgttttcatg      1140
tttactgtaa gaggggtacc aacagtattt caaggtacag aacaaaacaa aggtaatgga     1200
aatggagcaa ttctaaatgg tattgcagat acatggaatc gttggtcaat ggttaaaaag     1260
gactataatg gaaatataat tacagattat tttaatgaga atacagatac ttataaacta     1320
attagcaaat tgaattcatt taggcaaaaa tatgaagcct taagagaagg tactcaaaga     1380
gaaatgtggt cttcaccaca tttatatgca ttctcaagaa ggatggattc aggagaaaat     1440
gttggacaag aagttgtaaa tgtatttaat aattcagatg gagatcaaag tgcgaccatt     1500
ccaattagag ctgaaagtac tataaaagtt ggagataaac ttgtaaatct ttttgatgta     1560
aatgattcga tcacagttca acaaggaggt gttacaggaa acaaatatc agtgaattta      1620 ggagaaaata gtgggaagat ttatgttgtt aataatgaaa caccaaatcc agatcaaaag     1680
aacgtacaat ataaagtttc atataagaat actaatgcac aaaaagtaac acttcattat     1740
ggaactaatg gatggaaaaa cattcaagat gtaaatatga ctaagaattc caatgggagaa    1800 tttgaagcaa ctattacagt aaataataat gatattctaa attactgtat tcatattatt     1860
tcaccaacag actattggga taataatggt ggacagaatt ggaatgtaaa agtgactaag     1920
gcagaagatt atataaatga tggtgtaaag agtaatttga agagcgttaa tacaactaca     1980
tcagcagcga tagaatctgg tattgatagt actgtaaatc gttaa                     2025
```

<210> SEQ ID NO 5
<211> LENGTH: 13357
<212> TYPE: DNA
<213> ORGANISM: Clostridium saccharoperbutylacetonicum

<400> SEQUENCE: 5

```
gttcatggtt ttttcaatag gctagattca cgtataagta atttaggtga tattagggtt       60
atttcattct gagaatttgg attttgaatt tttttcatta aaatttcagc tgccacttca      120
ccaagtttaa atgtatctac atctagacaa gttaaggatg gagtggtgta agcagaaaat      180
ggttcattgt caaagtcac aattccaata tctgtggggc tatttaagcc cttttcttta       240
agtgctttaa gtacaccaaa tgcaacataa ttatttatgc atagtatggc atctatttca      300
ggaaaatctg ataataattg aagtgtaagt tcataaccac tttccttgtc tgagttgcct      360
```

```
tcttttatgt ataaattatt tttagtaaaa tttaatttag aaagtatgtt tttataacca      420
agaagccgat tgaaagatat tatttcattt gatttgccac caataaaggc tatattttta     480
taaccttgtt ctattaaatg acatgtggcc agttctcctc ctacagtatt attaacatca     540
acccagctgg tactattctt aaattccttt ggctgaccaa taaggacata aggaaagttt     600
aaaccgttga gcttactaat aatttccgaa ttgactattg aggtaggtat tatgattcca     660
tctacttttt tactatatat caatcgattt agaaattctg ctttgcattc tagtgaattt     720
atgtttgata gggttaactc atagttattg attccaacta tactttcaac tccaccaata     780
atattataga aaaagaaatc aagaaaatat tcctttctgc taatatctac tagaagacct     840
atattaaaac tattctggcg agctagctgc cttgccgaat tatttggaat atagttaagc     900
tctttcataa tgtttcttac tttgagcttt gtactttcag aaatagattt atgattattt     960
ataactttgg ataccgttga tttagataca tttgctgcgt gagctatatc atttatagta    1020 actttcatt ttaactcctt atgtgtgaaa ttgattattt aaatattata aaacattatt     1080 tgatttttt cgatatgtac attgttatta ataatattac tatttattgt aaagtatttt     1140
agaaattttt tatacttcta taagtttagc ataataatct aaaaatacat atatagttgc    1200
acatttcagt gctaaagatt aaatttattt atatcatcta aatcctctta aactcattta    1260
aagttccttc tctaaattga aaatgaatt tccaattgta ctcattgcat aatttataga    1320
tttgttcaca agcataaaga ctattaccta aaatgtaggt attaagtgtt ataaacttat    1380 atttaattt tttcataagt cttttagcat atgccttaat aaaacaatat atctggtgga    1440
agttaataca atatattgaa attgattcaa tattgcagta tactaaaatg agtaaaccgg    1500
tttcttaaat tttcaatgta tttaaagaat ttgtaagaca gaagaatata attttcaact    1560
ttataatatg cttatttgaa tgaattaata aaaagatgat ttttagtatt ttgtttataa    1620
gcctagtagt tacaagaagt aaatattttc tgtaaaagat tataaattag gagggagaat    1680
tgaaaaatgg taaaaaaaaa taagtatta gcatcaatcg tggcagcaac tttagttgca    1740
ggaacatttg taggatgtgg aggaacaaca gctacaagta ataatgctaa agaaattaca    1800
gtttggtcac atttgaaaga aaagagatt acagagctta ctaaagtagc ggaaaaatgg    1860
ggaagtgaaa agggagttaa ggttaatgtt gtagatgata aggggagat gcaagcatat    1920 atacaagccg ctaatagttc taaggtccaa gatatacttt ttggtgtacc taatgataac    1980
ttaggaacat ttcaaaaagc tggtttactt tcagaagtgc caagtggttt tatagatgag    2040
agtaaatata catctaaaca agtaatagat tcagtgacta tagaaggaaa aaaatatgca    2100
gttccattag cagctgaaac tagtgctcta ttttataata agataaagt ttcagaagta    2160 ccaaaaacta tggaagaagt tgttgaatta ggcaaaaaag taggatttga atacgatgta    2220 actgattat acagaagtta tggatttta gcatcgcaag gtagctatat ttttaaaaat    2280
aataatggaa ctgttgattc aaacgatatt ggattaggca atgaaggtgc gataaaagga    2340
tatcaattca ttcaagattt aattgttaaa gacaaattaa tgtctcaaga tattactgat    2400
gatatagcta aagcagattt ccaatcaggt aaatcagcat tttatatttc aggaccatgg    2460
gatatagaag catttaaaga ttcaggaatt aattttggta tagctccaat gccaacatta    2520
ggtgggaaaa ctgtttcaac attgatggga gttcaaactg catttgtaag ttcaaagtca    2580
cctaatcaag acttatcatg ggagttaatg aagtatctta tggaaaatag tgatgaccta    2640
atgattaagc aaggaaatag aattccagtt tcaaaagcag gtatagaaag tgatgcgttt    2700
aaagcggccg gaaacatgga tgtatttgct aaacaattag aagttgctac agcaatgcct    2760
```

```
aatattccag aaattcaaac tacttggact ccggtaaaaa ataatataat atctttaata    2820
agcggatcaa tggattcgaa agaaactgca aaacaaatag tagatcaaat taagaaggt     2880 ataaagcaac aaaaataaaa aagtaaatta agaaaataac atgtagtgct aaagtgattg    2940
aaaacaatta actttagcat cttttttaata ttaatatttt caaaatacac aagccaaaag   3000
aagttctcta gctatatagt ggagtttagt gtacattcta tgtaattata ttggtaaatg    3060
ttttcagaaa tgtattgaaa tccatttaag atggtagtat actaaatagg gaaaccggtt   3120
tacctaatgt aatacattta aagaaataaa ggaatgcgaa gacgacgata tttttgattt   3180
ttatgtgctt attttgatga aattatgaca aggtaatttt ataaaatcat ttattagttt    3240
ttcataatta tgtgaatgac taataaaaat ataatagt gggggaaagt tatgtttaga     3300
agaaaattta acaaggtaat attatctatc ttagttgcaa caattgtttc aagcactaac   3360
atgtttatga gtggaagcaa ggcacaagcg gcaattggaa atctaagtga aaacgatact   3420
atttatcaaa ttatggtaga cagattttat gatggagata aaacaaataa tgctacagga   3480
gatgcatttc gtaatacaga aaatcttgaa gatgatttta gatatatgca cggcggagat   3540
tggcaaggtg ttattgataa gttagattat attaagggca tgggatactc agccatttgg   3600
atatcaccgg ttgcggaacc acaaatgtgg tctagagctg atggcacagg aaaagtatgg   3660
cctacagctt atcatggata taatgtgaaa gatcccaata aggcaaatcc ttattttgga   3720
acaaaagaaa agctaaagga gttagtagat aaagctcacg aaaaggggat taagtaata    3780 atagatatag ttccaaatca tgttggggat tatatgttag gaaaacaagc ttattatgac   3840
atcaaggggt ttgagccggc agcacctttt aataatccaa attggtatca tcataatggc   3900
gatattgatt ggtcaagaga acactctgat ccccaaatgt tagatgatca tgatttgggc   3960
ggtttagatg attaaaatca agataattct gatgctaagg cagctatgaa taatgctatt   4020
aagtcatggt ttgattatac tggagctgat gcagcaaggg ttgacgcagc aaaatgtatg   4080
aaaccatctt atattaacga gttacaaaag tatataggag ttaatacttt tggagaaaat   4140
tttgatatga atgtagattt tgtgaagaag tgggttggat ccgatgcaga atggggaatg   4200
ctagattttc cattatatca agcaataaat aatgattttg catcaggaca atctttttgat   4260 gacatgtcat catcaggtac ttgctctatt aaaaatattt tagcacaaga caataaaatat   4320 aatggttatg caaatcatat ggtgactttt atagataatc atgatcgtaa tagatttta    4380 acagtagcaa atggtaatgt aaaaaaactt caaaatgcac ttgtttttcat gtttactgta   4440 agaggggtac caacagtatt tcaaggtaca gaacaaaaca aaggtaatgc aaatggagca   4500
agtataaatg gtattgcaga tacatggaat cgttggtcaa tggttaaaaa ggattacaat    4560
ggaaatgtaa ttcagatta ttttaatgag aatacagata cttataaact aattaacaaa    4620
ttgaattcat ttaggcaaaa atatgaagcc ttaagagaag gtactcaaag agaaatgtgg   4680
tcttcaccac atttatatgc attctcaaga aggatggatt caggagaaaa tgttggacaa   4740
gaagttgtaa atgtatttaa taattcagat ggagatcaaa gtgcgaccat tccaattaga   4800
gctgaaagta ctataaaagt tggagataaa tttgtaaatc ttttttgatgt aaatgattcg   4860 atcacagttc aacaaggagg tgttacagga aaacaaatat cagtgaattt aggagaaaat   4920
agtgggaaga tttatgttgt taataatgaa acaccaaatc cagatcaaaa gaacgtacaa   4980
tataaagttt catataagaa tactaatgca caaaaagtaa cacttcatta tggaactaat   5040
ggatggaaaa acattcaaga tgtaaatatg actaagaatt ccaatggaga atttgaagca   5100
```

-continued

```
actattacag taaataataa tgatattcta aattactgta ttcatattat ttcaccaaca      5160
gactattggg ataataatgg tggacagaat tggaatgtaa aagtgactaa ggcagaagat      5220
tatataaatg atggtgtaaa gagtaatttg aagagcgtta atacaactac atcagcagct      5280
atagactctg ggattgatag tactgtaaat cgttaaatat aaatgttaat ttaaagaaaa      5340
atttcatcat gcatattata tttggcacac aaaaatatta aatatctact tttcgcttct      5400
aaatggaaaa accgcatggt tagatcctaa agccttataa aatccatgtt tccataattg      5460
aagcgaaata taggtagata ataatgtata aattaggagg ataaattgat gaaaggtgaa      5520
ataatatatc aaattttttcc agacagattt aataaatcaa gacaaaataa taatgttgaa     5580
ggtttaaaag aatgggaaag tgaagttgat ggacaatgtg ttatgggagg tgatttaatt      5640
ggaattaaag agaaacttga ttatctatca aaactcggtg ttagtgcaat ttatttaaat      5700
ccaattttttc aggcaaattc taatcataag tatgatactg ttaactatta taatatagat     5760
agttctttttg gaactttaga tgattttaga gaattagtag attcatgtca taaaaaaat      5820
ataaaagtta ttattgatgg agttttttaac catactagcc cagatttttt tgctttcaaa    5880
gatatattag aaaatcaaga aagatcaaaa tataaggatt ggtatactat ttttagttat     5940
ccagttaaag tggaaagtcc acctaattat agaaattttg gaggatgtat agatatgccg     6000
cgtcttaata ctgaaaatgt tgaagttcaa aagtatatag ttgatgttat taagtattgg     6060
gaagggatga aaatagatgg attaagacta gatgtaccat attatattga agactctatg     6120
ttagaaaaaa taagaaaatc tactagctta tatatagtag gtgaaatatg ggggtgtggc      6180
aagaaatttg tgcctcaata ttttgatgga gtaatgaatt attcatttag agatttagtg      6240
caaaaagcag ttataagaca aagcattgat gcatcaatat tcatagatga atggaatttc     6300
atagaagaaa catacgggca gaatatacat tgctgcttta atatgtctgg aagtcatgat      6360
acagaaagga ttttttaattt ctgcagagga gatataaaga gagaaaaatt attctatgca    6420
ttttttatttt tattcccagg aatgcctctt gtatattatg gagatgaaat aggtatgaaa     6480
ggagaaaatg acccttattg tagaggaact atggaatgga atgaaagtaa atggaattat      6540
gatatatata atcatgtaaa aggtttaata gaacttagaa atagtagtga agcattgcaa      6600
aaagggacta tacaatttgt tggacataaa gaaatgatgt ttgcatttga aagagtgtat      6660
gcagaaaaaa gagttaaagt atttatgaat tttggacata gcaaacagtc tattgatgga      6720
tttgaactag atggtcttag ttataaagtt atagtttagc attcaaggat aactttgcaa      6780
gttataaaat agcaacttta aacaatcaat gttctttaat tggacattgg ttatcacaat      6840
atgtttatct gtttggataa atatatgaat aaatttcatt aattttattt ttttccatga     6900
taaaaatcat agagaaaaag gcatatattt aaatttggct ttattagtaa attcaattag     6960
tataatatat tttagtgata ttgacataag agattaaata aattatttat ataaaaaaag    7020
taagattaag aaatactaga tttaaattttt tttatatcaa agaggtgggc aattatgaaa    7080
caagccaaaa caaaaaaaat aacacatact ttgaaatcag tgccgtattt attaccagcc      7140
attatttcaa taattatatt ttcaatatta ccaatactta atacaatata tttggcattt      7200
acagactata ctatgtattc acaaggaaaa attaattttg taggaattgc aaattttaaa     7260
gaagtatttg ctggtccatt taaagaagta ttttttccgg tatttatatg gacatgtgtc     7320
tttgctacat tggcaactgc aggaacattt tgttaggac taattatggc aattcttgta      7380
aataatgaaa atataaaaga acgagggctt tataaagcaa ttttaattat tccatgggca     7440
ttaccagcta ctgttgcaat actttcatgg caaggtttat taaatggaag ttatggggca     7500
```

```
attaataatt tacttataag tgtacatgct atttcagcgc ctattccatg gttaactaat    7560
ccattatggg caagaattgc aataatcata gtaactatat ggctaggatt tccatatgcc    7620
atgaatattt gtttgggttc acttcaatcg atacctaaaa catattatga agcagctgac    7680
gttgatggag ccagcaagtt tgtaaaattt attaaaataa ctttaccttc gcttgcacaa    7740
acagcatatc cattagttat ttcatccttt gcatttaact ttaataattt tggtcaagca    7800
tatttaatta ctaatggtaa tccggcaaga cctggaacac aatttgcagg tttcacagat    7860
atattggctt cagtaaatta taaattgtca ataacatttg aagatatgaa aattgcttcc    7920
actataagca ttattatatt tataatttta gctacaattt catacataca aatgaaagca    7980
tcaggacaat ttgaggaggt tgattaaaat gacatcaaat gcagggaatt tgaaattaaa    8040
taatacagaa ggacaaagtg aagaaataca aaacataaaa ttaaaatatg taaaaaaatt    8100
aagaccagca gaaataagaa ctgcatggat ttcaaggata gtactttgga ttatgattgt    8160
aatagttctt attccaatca tggcagttgt ttcagcatct atggctaaag gtaattcatt    8220
tacgcaaacc tctattttc ctaaatcatt tactttagag aattatgtaa aagtaataac    8280
tcaaactaag tttttaatat gggcaagaaa ttcattagtt gtttgtttta gcgttgctat    8340
gatgcagcta atcatgacaa ttccagcagc ttttgcgttt tctaagctta ggtttaaagg    8400
tagaaaattt ggacttatga cacttttgat attacagatg tttccaaata caatggcatt    8460
accagcaatt ttaagtgttg catataatat tcggggtgga atggataatt tattaccatt    8520
aatattaatt atatcagtag gtagtgcata taacatctgg cttatgaagg gatacatgga    8580
tggaattcca aaagaattaa ctgaaactgc atatatagat ggagcaacaa cttttcaagc    8640
tttcattaag gtagtattgc cactaataaa gaatatgata atagtaatat ttatatttgc    8700
ttttgttgga gcttatagcg aatttttatt tacatcagct cttataaaag atcaatatac    8760
agaaactcta gcaacaggta tgcaaggatt cattaaagat catttttcag ctaactggac    8820
tcaatattca gcggctgcaa taatggcatc attaccagtt gttttgatat cagtattttc    8880
acaaaaattc tttgcaaaag gattaactgc tggatcagta aaaggctaaa gtggggacgt    8940
gagtatataa tgaagccaac taaggattag aaaataagta gcaattttaa taaaattaaa    9000 aagttttct ataaaaatct ttcaactaaa gaaaattcaa aaaacaatga tgtaactatt    9060
aaaaaatcta aaagtttgca ttttaaatta ttggaaagta tgttctgtat ttcaattatt    9120
ccaataataa ttatttgcag cgttacttt attaaaatta attttattaa gtaatgttaa    9180
ttcataagct gaagatgtga attcagaatc attgatttta aatgataaaa gtaaggaatt    9240
atcgttagct atatctaatg taaatgagac tttaggcaag attgatcttg gaactataga    9300
ttctacaaat aatttggaat ctttagtgtt aaatatggag gaggtatcaa atccaatgat    9360
caaagtagcg taatagttat atataagtga aaaggggaag gaattcttat gagattcgaa    9420
gctgtatatc atagagcctc agataactta tgttattcaa ttgataaaga caatttaatt    9480
gtaaatataa agactggtta tgatgtagaa aaagtgttta tatattatgg tgatccattt    9540
gatggaggaa tttaggtgg cgaatggaaa tggaaaggaa aaagagaaga aattccattt    9600 aaaagagat taaagcacca aatatggtgg acaactactt tgaaactgaa gtataaaaga    9660
tgtaaatact attttgaatt aacggggaat gaagaaacct ggttttattt tgaagattgt    9720
tttttaagtg aaaaacaaat gcaattggac ggaaaaatgt tgcaatgttt tacatttcca    9780
tggatgaatg aagctgatat aaataaaaca ccagcatggg taaatgatat ggtttggtat    9840
```

```
cagatattcc cagagcgttt ttgtaatgga aatccttcaa ttaatcccaa aggggtccag    9900
ccttggcata aaggaggcgt tacaaatgaa gagttttatg gtggggattt gcaggggata    9960
ataaataaat taaattattt aaaagaaata ggaattacag gcatatattt aaatccaata   10020
ttcgaatctc cgtcagcaca taaatatgat acaactgatt atatgaaaat agatcctaat   10080
tttggagatg aaaatgtatt tagaaagctt gtaaataaag cacatgaaaa agggattagg   10140
attatgcttg atggagtgtt taatcattgt ggagctaagt ttggaccatg gttagatgta   10200
cttgaaaatg gtcctagttc caaatattat agttggttta tggtaaataa gtggcctttt   10260
gatgataata atcacgatac aaaggatgga cgatttttatt cttttgcctt taatcagaaa   10320
atgccaaaat taaatacaaa taatccagaa gtaattgatt atttaattaa ggtatgtgag   10380
tattgggtaa aaaattataa gattgatgga ttaagattag atgttgcaaa tgaaatttcg   10440
cataagttct gtaagaagct tagagaaaaa atgaaatcgt taaatccaga cttctatatt   10500
ttaggtgaaa tatggcatga ttctattcct tggcttagag gtgatgaatt tgatgctatt   10560
atgaattatt cactaactag tagtatatca gacttctgga tagataagag tttaactaag   10620
gatgattttg agtacacaat aaatagatgc tatacaatat atatgcagca aaataatgat   10680
gtgttattta atttgttgga ttctcatgat acagaacgct taatttcaag agtaaaagac   10740
attaacgtat tttatcaaca gctagctgta ctatttacga tgccaggaag tccatgcata   10800 tttttatggta cagaagttgc acttgaagga aagtatgatc ccgattgccg aagatgtatg   10860
ccatgggatg aaataaaaag tggaatttat gatgataaga ttaatataat gaaggcgttg   10920 attaattttaa gaaaagagca aaaattattt agaagccgta attttcattt tccaaataca   10980
attaaaaata gcagggtaat agaatatatt aaaatagatg aaaatgggaa taggttagaa   11040
attttactaa attgttcaaa tatagatgtt ttaatagaaa ataatggtag tgttttgttt   11100
agtaatttat attctaataa tagactgctt aaaaaaggtg tattaattag gaaggttgat   11160
tctatataag gttcaatcaa ataaataaca agtccgttta catcatgggc tgataaaaaa   11220
tatccatttt gcgatttgat tttatttata aatgaaaaag atatttaatt aaatcagcaa   11280
tatgtactta ttaattataa atgaaaaaat aattttgaag aggagtagtc atggaattaa   11340
catataggtt cggaagagga tactggagaa atataaagga aggaaacgag agagaatgga   11400
tgataggcaa tggtattggc gggtataagca gtcaaactat cattaatagt ggatttagat   11460
gtcataatgg gtatttaata gcagcaatga atccgccagt agaacgttat tcaatattat   11520
atagaactca ggaaaaaatc gtcacagatg gaagaacata tgatttgact tgtcaggaat   11580
ataaggatta tacgaagaat ggttatgagt atctcaaaag ttttatattt gattcagtgc   11640
ctcaatatat ttatcaaata gaagatataa atgtaaaaaa aactatagct atggaatatg   11700
gatataatac tgtagctata tgttatgaga ttgaaaatgg aagttctaag gctaaaattg   11760 atattcacacc actgtttaat tttaaggaag ctggtacatt taaggcttct gagcagctgg   11820 atttttaaaac tgaattacaa gacgatatat taaaattgta tcctaatgaa gatgataaga   11880
agataataag ttttatgtca tcagcaggca tatttaagga cagaagtctt ataaaagtac   11940
agaatgattt taattataat ccattaattg aagagaatca ttactatgaa tttgaaaata   12000
gaaatggatt tattgggtta aataatcatt atacgccata tgatattgaa attgaattag   12060
agccttttga aactaaaaag tttttatttaa aatgtacagt agaagagtta ggtgataaag   12120
acggatttga tattgttaaa gaatataagg aaagaacaaa tgaattattg aatagatcag   12180
gctataaaga ttttttttgca ttaaatttag taaaagcagc tgaccatttt attgtagata   12240
```

-continued

```
gaaaaagtac tggattgaaa acaatacttg caggatttcc ttggtttgtt gattggggga    12300
gagacactat gatagctttt gaaggtttaa cgctgtgtac aaagagattt gaggatgcaa    12360
gagaaatatt aaagtctttt gcagaatata taaagatgg acttgttcca aatgttttg     12420 cggataaagg aacacaagcg ttttacaata ctgcagatgc atcattatgg tatatacaag   12480
ctgtatataa gtatttaaaa tatactggaa agaaaagtga ttttaagttt gttaatgata   12540
aattattcga caagttaatt gaaattattg atgcttattc aaatggcaca cattttcaa    12600 taggtatgga tgatgattgt cttattcatg ctggcagcgg attggatcaa gtaacgtgga   12660
tggatgtaag agtagacgaa atggttgtta ctccaaggca tggtaaacca gtagaaataa   12720
atgctctttg gtataatgcc ctttgcataa tggattggtt atgtagaaag tatgaaatga   12780
atggatcaaa atatgaaagt ttagcgagaa aagttaaaaa ctcctttaac aaaaaattct   12840
ggaatgaaaa agaacagtgt ttatttgatg ttgttgatga ttatgatggg aaagttaggc   12900
caaatcaaat atgggcagta tcattgccat ttactatgtt agaaaaagaa aaggaagcga   12960
aagttgtgaa taaagtatat aaagaattat attcgactta tggattgaga tcgctgtcat   13020
acttagataa agattttaag agcgaatata taggaccact tatgaaaagg gatttagcat   13080
atcatatggg gacaacatgg gcattcttaa tagggagctt tatatcagca tattgtaagg   13140
taaataatca ctctaaagaa gcagtaagta gagcaaaaga aatgtgtgaa gtatttcagg   13200
atcatatgaa agatggatgc ataaatggaa tagctgaagt atttgatgga aaattttcag   13260
ctacaggcag gggatgctat agtcaagcct ggagtgtagg cgaagtttta agagcatata   13320
ctaacgatgt actgccattt atttgatcta ctttgca                            13357
```

<210> SEQ ID NO 6
<211> LENGTH: 50
<212> TYPE: PRT
<213> ORGANISM: Bacillus sp. 1-1

<400> SEQUENCE: 6

Gly Thr Asp Phe Ser Ser Tyr Glu Asp Ser Ile Tyr Arg Asn Leu Tyr
1               5                   10                  15

Asp Leu Ala Asp Tyr Asp Leu Asn Asn Thr Val Met Asp Gln Tyr Leu
            20                  25                  30

Lys Glu Ser Ile Lys Phe Trp Leu Asp Lys Gly Ile Asp Gly Ile Arg
        35                  40                  45

Val Asp
    50

<210> SEQ ID NO 7
<211> LENGTH: 50
<212> TYPE: PRT
<213> ORGANISM: Bacillus sp. KC201

<400> SEQUENCE: 7

Gly Thr Asp Phe Ser Ser Tyr Glu Asp Ser Ile Tyr Arg Asn Leu Tyr
1               5                   10                  15

Asp Leu Ala Asp Tyr Asp Leu Asn Asn Thr Val Met Asp Gln Tyr Leu
            20                  25                  30

Lys Glu Ser Ile Lys Phe Trp Leu Asp Lys Gly Ile Asp Gly Ile Arg
        35                  40                  45

Val Asp
    50

<210> SEQ ID NO 8
<211> LENGTH: 49
<212> TYPE: PRT
<213> ORGANISM: Brevibacillus brevis

<400> SEQUENCE: 8

Gly Thr Asp Phe Ser Ser Tyr Glu Asp Ser Ile Tyr Arg Asn Leu Tyr
1               5                   10                  15

Asp Leu Ala Asp Tyr Asp Leu Asn Asn Lys Val Val Asp Gln Tyr Leu
            20                  25                  30

Lys Glu Ser Ile Lys Leu Trp Leu Ile Lys Ile Asp Gly Ile Arg Val
        35                  40                  45

Asp

<210> SEQ ID NO 9
<211> LENGTH: 50
<212> TYPE: PRT
<213> ORGANISM: Bacillus ohbensis

<400> SEQUENCE: 9

Gly Thr Asp Phe Ser Ser Tyr Glu Asp Ser Ile Tyr Arg Asn Leu Tyr
1               5                   10                  15

Asp Leu Ala Asp Tyr Asp Leu Asn Asn Thr Val Met Asp Gln Tyr Leu
            20                  25                  30

Lys Glu Ser Ile Lys Leu Trp Leu Asp Lys Gly Ile Asp Gly Ile Arg
        35                  40                  45

Val Asp
    50

<210> SEQ ID NO 10
<211> LENGTH: 50
<212> TYPE: PRT
<213> ORGANISM: Bacillus sp.

<400> SEQUENCE: 10

Gly Thr Asp Phe Ser Ser Tyr Glu Asp Ser Ile Tyr Arg Asn Leu Tyr
1               5                   10                  15

Asp Leu Ala Asp Tyr Asp Leu Asn Asn Thr Val Met Asp Gln Tyr Leu
            20                  25                  30

Lys Glu Ser Ile Lys Leu Trp Leu Asp Lys Gly Ile Asp Gly Ile Arg
        35                  40                  45

Val Asp
    50

<210> SEQ ID NO 11
<211> LENGTH: 50
<212> TYPE: PRT
<213> ORGANISM: Bacillus sp. 38-2

<400> SEQUENCE: 11

Gly Thr Asp Phe Ser Thr Ile Glu Asn Gly Ile Tyr Lys Asn Leu Tyr
1               5                   10                  15

Asp Leu Ala Asp Leu Asn His Asn Asn Ser Ser Val Asp Val Tyr Leu
            20                  25                  30

Lys Asp Ala Ile Lys Met Trp Leu Asp Leu Gly Val Asp Gly Ile Arg
        35                  40                  45

Val Asp
    50

```
<210> SEQ ID NO 12
<211> LENGTH: 50
<212> TYPE: PRT
<213> ORGANISM: Bacillus circulans

<400> SEQUENCE: 12

Gly Thr Asp Phe Ser Thr Ile Glu Asn Gly Ile Tyr Lys Asn Leu Tyr
1               5                   10                  15

Asp Leu Ala Asp Leu Asn His Asn Asn Ser Ser Val Asp Val Tyr Leu
            20                  25                  30

Lys Asp Ala Ile Lys Met Trp Leu Asp Leu Gly Val Asp Gly Ile Arg
        35                  40                  45

Val Asp
    50

<210> SEQ ID NO 13
<211> LENGTH: 50
<212> TYPE: PRT
<213> ORGANISM: Bacillus sp. 1011

<400> SEQUENCE: 13

Gly Thr Asp Phe Ser Thr Ile Glu Asn Gly Ile Tyr Lys Asn Leu Tyr
1               5                   10                  15

Asp Leu Ala Asp Leu Asn His Asn Asn Ser Ser Val Asp Val Tyr Leu
            20                  25                  30

Lys Asp Ala Ile Lys Met Trp Leu Asp Leu Gly Val Asp Gly Ile Arg
        35                  40                  45

Val Asp
    50

<210> SEQ ID NO 14
<211> LENGTH: 50
<212> TYPE: PRT
<213> ORGANISM: Bacillus circulans

<400> SEQUENCE: 14

Gly Thr Asp Phe Ser Thr Thr Glu Asn Gly Ile Tyr Lys Asn Leu Tyr
1               5                   10                  15

Asp Leu Ala Asp Leu Asn His Asn Asn Ser Thr Val Asp Val Tyr Leu
            20                  25                  30

Lys Asp Ala Ile Lys Met Trp Leu Asp Leu Gly Ile Asp Gly Ile Arg
        35                  40                  45

Met Asp
    50

<210> SEQ ID NO 15
<211> LENGTH: 50
<212> TYPE: PRT
<213> ORGANISM: Bacillus sp. B1018

<400> SEQUENCE: 15

Gly Thr Asp Phe Ser Thr Thr Glu Asn Gly Ile Tyr Lys Asn Leu Tyr
1               5                   10                  15

Asp Leu Ala Asp Leu Asn His Asn Asn Ser Thr Ser Asp Val Tyr Leu
            20                  25                  30

Lys Asp Ala Ile Lys Met Trp Leu Asp Leu Gly Ile Asp Gly Ile Arg
        35                  40                  45

Met Asp
    50
```

<210> SEQ ID NO 16
<211> LENGTH: 50
<212> TYPE: PRT
<213> ORGANISM: Bacillus sp. 17-1

<400> SEQUENCE: 16

Gly Thr Asp Phe Ser Thr Thr Glu Asn Gly Ile Tyr Lys Asn Leu Tyr
1               5                   10                  15

Asp Leu Ala Asp Leu Asn His Asn Asn Ser Thr Val Asp Thr Tyr Leu
            20                  25                  30

Lys Asp Ala Ile Lys Met Trp Leu Asp Leu Gly Ile Asp Gly Ile Arg
        35                  40                  45

Met Asp
    50

<210> SEQ ID NO 17
<211> LENGTH: 50
<212> TYPE: PRT
<213> ORGANISM: Bacillus circulans

<400> SEQUENCE: 17

Gly Ser Asp Phe Ser Ser Leu Glu Asn Gly Ile Tyr Lys Asn Leu Tyr
1               5                   10                  15

Asp Leu Ala Asp Phe Asn His Asn Asn Ala Thr Ile Asp Lys Tyr Phe
            20                  25                  30

Lys Asp Ala Ile Lys Leu Trp Leu Asp Met Gly Val Asp Gly Ile Arg
        35                  40                  45

Val Asp
    50

<210> SEQ ID NO 18
<211> LENGTH: 50
<212> TYPE: PRT
<213> ORGANISM: Bacillus sp. 6.3.3

<400> SEQUENCE: 18

Gly Ser Asp Phe Ser Ser Leu Glu Asn Gly Ile Tyr Lys Asn Leu Tyr
1               5                   10                  15

Asp Leu Ala Asp Phe Asn His Asn Asn Ala Thr Ile Asp Lys Tyr Phe
            20                  25                  30

Lys Asp Ala Ile Lys Leu Trp Leu Asp Met Gly Val Asp Gly Ile Arg
        35                  40                  45

Val Asp
    50

<210> SEQ ID NO 19
<211> LENGTH: 50
<212> TYPE: PRT
<213> ORGANISM: Bacillus licheniformis

<400> SEQUENCE: 19

Gly Ser Asp Phe Ser Thr Leu Glu Asn Gly Ile Tyr Lys Asn Leu Tyr
1               5                   10                  15

Asp Leu Ala Asp Leu Asn His Asn Asn Ser Thr Ile Asp Thr Tyr Phe
            20                  25                  30

Lys Asp Ala Ile Lys Leu Trp Leu Asp Met Gly Val Asp Gly Ile Arg
        35                  40                  45

Val Asp

```
<210> SEQ ID NO 20
<211> LENGTH: 50
<212> TYPE: PRT
<213> ORGANISM: Paenibacillus macerans

<400> SEQUENCE: 20

Gly Thr Asp Phe Ser Thr Thr Glu Ser Gly Ile Tyr Lys Asn Leu Tyr
1               5                   10                  15

Asp Leu Ala Asp Ile Asn Gln Asn Asn Asn Thr Ile Asp Ser Tyr Leu
            20                  25                  30

Lys Glu Ser Ile Gln Leu Trp Leu Asn Leu Gly Val Asp Gly Ile Arg
        35                  40                  45

Phe Asp
    50

<210> SEQ ID NO 21
<211> LENGTH: 50
<212> TYPE: PRT
<213> ORGANISM: Thermoanaerobacterium thermosulfurigenes

<400> SEQUENCE: 21

Gly Thr Asp Phe Ser Ser Tyr Glu Asp Gly Ile Tyr Arg Asn Leu Phe
1               5                   10                  15

Asp Leu Ala Asp Leu Asn Gln Gln Asn Ser Thr Ile Asp Ser Tyr Leu
            20                  25                  30

Lys Ser Ala Ile Lys Val Trp Leu Asp Met Gly Ile Asp Gly Ile Arg
        35                  40                  45

Leu Asp
    50

<210> SEQ ID NO 22
<211> LENGTH: 50
<212> TYPE: PRT
<213> ORGANISM: Thermoanaerobacter sp. ATCC 53627

<400> SEQUENCE: 22

Gly Thr Asn Phe Ser Ser Tyr Glu Asp Gly Ile Tyr Arg Asn Leu Phe
1               5                   10                  15

Asp Leu Ala Asp Leu Asp Gln Asn Ser Thr Ile Asp Ser Tyr Leu
            20                  25                  30

Lys Ala Ala Ile Lys Leu Trp Leu Asp Met Gly Ile Asp Gly Ile Arg
        35                  40                  45

Met Asp
    50

<210> SEQ ID NO 23
<211> LENGTH: 50
<212> TYPE: PRT
<213> ORGANISM: Geobacillus stearothermophilus

<400> SEQUENCE: 23

Gly Thr Thr Phe Ser Ser Leu Glu Asp Gly Ile Tyr Arg Asn Leu Phe
1               5                   10                  15

Asp Leu Ala Asp Leu Asn His Gln Asn Pro Val Ile Asp Arg Tyr Leu
            20                  25                  30

Lys Asp Ala Val Lys Met Trp Ile Asp Met Gly Ile Asp Gly Ile Arg
        35                  40                  45
```

Met Asp
    50

<210> SEQ ID NO 24
<211> LENGTH: 50
<212> TYPE: PRT
<213> ORGANISM: [Bacillus] agaradhaerens (unclassified
      Sporolactobacillaceae)

<400> SEQUENCE: 24

Gly Thr Asp Phe Ser Asn Tyr Glu Asp Glu Ile Tyr Arg Asn Leu Phe
1               5                   10                  15

Asp Leu Ala Ser Phe Asn His Ile Asn Ser Glu Leu Asn Asn Tyr Leu
            20                  25                  30

Glu Asp Ala Val Lys Lys Trp Leu Asp Leu Gly Ile Asp Gly Ile Arg
        35                  40                  45

Ile Asp
    50

<210> SEQ ID NO 25
<211> LENGTH: 50
<212> TYPE: PRT
<213> ORGANISM: [Bacillus] agaradhaerens (unclassified
      Sporolactobacillaceae)

<400> SEQUENCE: 25

Gly Thr Asp Phe Ser Asn Tyr Glu Asp Glu Ile Tyr Arg Asn Leu Phe
1               5                   10                  15

Asp Leu Ala Ser Phe Asn His Ile Asn Ser Glu Leu Asn Asn Tyr Leu
            20                  25                  30

Glu Asp Ala Val Lys Lys Trp Leu Asp Leu Gly Ile Asp Gly Ile Arg
        35                  40                  45

Ile Asp
    50

<210> SEQ ID NO 26
<211> LENGTH: 50
<212> TYPE: PRT
<213> ORGANISM: [Bacillus] agaradhaerens (unclassified
      Sporolactobacillaceae)

<400> SEQUENCE: 26

Gly Thr Asp Phe Ser Thr Tyr Glu Asp Glu Ile Tyr Arg Asn Leu Phe
1               5                   10                  15

Asp Leu Ala Ser Phe Asn His Ile Asn Ala Glu Leu Asn Asn Tyr Leu
            20                  25                  30

Glu Asp Ala Val Lys Lys Trp Leu Asp Leu Gly Ile Asp Gly Ile Arg
        35                  40                  45

Ile Asp
    50

<210> SEQ ID NO 27
<211> LENGTH: 50
<212> TYPE: PRT
<213> ORGANISM: [Bacillus] clarkia (unclassified Sporolactobacillaceae)

<400> SEQUENCE: 27

Gly Ser Asp Phe Ser Asp Tyr Glu Asn Ser Ile Tyr Arg Asn Leu Tyr
1               5                   10                  15

Asp Leu Ala Ser Leu Asn Gln Gln His Ser Phe Ile Asp Lys Tyr Leu
            20                  25                  30

```
Lys Glu Ser Ile Gln Leu Trp Leu Asp Thr Gly Ile Asp Gly Ile Arg
        35                  40                  45
Val Asp
    50

<210> SEQ ID NO 28
<211> LENGTH: 50
<212> TYPE: PRT
<213> ORGANISM: Bacillus

<400> SEQUENCE: 28

Gly Ser Asp Phe Ser Ser Tyr Glu Asp Ser Ile Tyr Arg Asn Leu Tyr
1               5                   10                  15
Asp Leu Ala Ser Leu Asn Gln Gln Asn Ser Phe Ile Asp Arg Tyr Leu
            20                  25                  30
Lys Glu Ser Ile Gln Met Trp Leu Asp Leu Gly Ile Asp Gly Ile Arg
        35                  40                  45
Val Asp
    50

<210> SEQ ID NO 29
<211> LENGTH: 50
<212> TYPE: PRT
<213> ORGANISM: Streptococcus pyogenes M1 GAS

<400> SEQUENCE: 29

Trp Thr Asp Phe Ser Thr Tyr Glu Asn Ser Ile Tyr His Ser Met Tyr
1               5                   10                  15
Gly Leu Ala Asp Leu Asn Asn Ile Asn Pro Lys Val Asp Gln Tyr Met
            20                  25                  30
Lys Glu Ala Ile Asp Lys Trp Leu Asp Leu Gly Val Asp Gly Ile Arg
        35                  40                  45
Val Asp
    50

<210> SEQ ID NO 30
<211> LENGTH: 49
<212> TYPE: PRT
<213> ORGANISM: Thermococcus kodakarensis KOD1

<400> SEQUENCE: 30

Ile Tyr Thr Trp Ser Gly Ile Pro Leu Lys Tyr Ala Asn Leu Tyr Gly
1               5                   10                  15
Leu Ala Asp Phe Asn Gln Leu Asn Pro Trp Val Asp Ser Tyr Leu Thr
            20                  25                  30
Glu Gly Ala Met Leu Phe Val Asp Ser Gly Ala Cys Gly Leu Arg Ile
        35                  40                  45
Asp

<210> SEQ ID NO 31
<211> LENGTH: 50
<212> TYPE: PRT
<213> ORGANISM: Thermococcus sp. B1001

<400> SEQUENCE: 31

Ile Thr Asn Trp Asn Asp Arg Trp Glu Val Arg Tyr Lys Asn Leu Phe
1               5                   10                  15
Asn Leu Ala Asp Leu Asn Gln Leu Asn Pro Trp Val Asp Asn Tyr Leu
            20                  25                  30
```

Lys Glu Ser Thr Val Ser Tyr Leu Glu Ala Gly Ile Gly Gly Ile Arg
            35                  40                  45

Ile Asp
    50

<210> SEQ ID NO 32
<211> LENGTH: 50
<212> TYPE: PRT
<213> ORGANISM: Klebsiella oxytoca

<400> SEQUENCE: 32

Val Thr Asn Trp Asn Asp Phe Phe Gln Val Lys Asn His Asn Leu Phe
1               5                   10                  15

Asn Leu Ser Asp Leu Asn Gln Ser Asn Thr Asp Val Tyr Gln Tyr Leu
            20                  25                  30

Leu Asp Gly Ser Lys Phe Trp Ile Asp Ala Gly Val Asp Ala Ile Arg
            35                  40                  45

Ile Asp
    50

<210> SEQ ID NO 33
<211> LENGTH: 50
<212> TYPE: PRT
<213> ORGANISM: Nostoc sp. PCC 9229

<400> SEQUENCE: 33

Val Gln Asn Trp Glu Asp Glu Trp Gln Val Gln Asn Cys Glu Leu Ala
1               5                   10                  15

Gly Leu Ala Thr Phe Asn Glu Asn Asn Ser Asp Tyr Arg Gln Tyr Ile
            20                  25                  30

Lys Ser Ala Ile Lys Gln Trp Leu Asp Arg Gly Val Asp Ala Leu Arg
            35                  40                  45

Val Asp
    50

<210> SEQ ID NO 34
<211> LENGTH: 60
<212> TYPE: PRT
<213> ORGANISM: Bacillus circulans

<400> SEQUENCE: 34

Asp Ile Asn Trp Ser Leu Ala Asp Gly Arg Tyr Asp Gln Trp Ala Gln
1               5                   10                  15

Asp Tyr Leu Glu Asn His Asp Leu Gly Gly Leu Asp Ile Asp Phe
            20                  25                  30

Asp Val Pro Ala Ala Lys Gln Ala Ile Phe Ser Ser Ile Lys Gly Trp
            35                  40                  45

Phe Asp Tyr Thr Gly Ala Asp Gly Ala Arg Val Asp
    50                  55                  60

<210> SEQ ID NO 35
<211> LENGTH: 60
<212> TYPE: PRT
<213> ORGANISM: Paenibacillus curdlanolyticus YK9

<400> SEQUENCE: 35

Asp Ile Asn Trp Ser Leu Val Asp Gly Ser Tyr Thr Ala Ala Thr Gln
1               5                   10                  15

Asp Tyr Leu Glu Asn His Asp Leu Ala Gly Leu Asp Asp Ile Asp Phe

```
                20                  25                  30

Asp Asn Ala Gln Ala Lys Gln Ala Met Phe Asp Ser Ile Lys Gly Trp
            35                  40                  45

Phe Asp Tyr Thr Gly Ala Asp Gly Ala Arg Val Asp
        50                  55                  60

<210> SEQ ID NO 36
<211> LENGTH: 55
<212> TYPE: PRT
<213> ORGANISM: Clostridium saccharoperbutylacetonicum N1-504

<400> SEQUENCE: 36

Asp Ile Asp Trp Ser Arg Glu His Ser Asp Pro Gln Met Leu Asp Asp
1               5                   10                  15

His Asp Leu Gly Gly Leu Asp Asp Leu Asn Gln Asp Asn Ser Asp Ala
            20                  25                  30

Lys Ala Ala Met Asn Asn Ala Ile Lys Ser Trp Phe Asp Tyr Thr Gly
        35                  40                  45

Ala Asp Ala Ala Arg Val Asp
    50                  55

<210> SEQ ID NO 37
<211> LENGTH: 54
<212> TYPE: PRT
<213> ORGANISM: Clostridium saccharoperbutylacetonicum N1-4 (HMT)

<400> SEQUENCE: 37

Asp Ile Asp Trp Ser Arg Glu His Ser Asp Pro Gln Met Leu Asp Asp
1               5                   10                  15

His Asp Leu Gly Gly Leu Asp Asp Leu Asn Gln Asp Asn Ser Asp Ala
            20                  25                  30

Lys Ala Met Asn Asn Ala Ile Lys Ser Trp Phe Asp Tyr Thr Gly Ala
        35                  40                  45

Asp Ala Ala Arg Val Asp
    50

<210> SEQ ID NO 38
<211> LENGTH: 59
<212> TYPE: PRT
<213> ORGANISM: Abiotrophia defectiva ATCC 49176

<400> SEQUENCE: 38

Asp Ile Asp Trp Asn Lys Glu Phe Pro Arg Thr Ala Glu Ser Ile Gln
1               5                   10                  15

Met Met Glu Asp His Asp Leu Ser Met Leu Asp Asp Ile Asp Tyr Asp
            20                  25                  30

Val Pro Glu Ala Lys Gln Ala Met Leu Glu Ala Met Lys Asn Trp Tyr
        35                  40                  45

Asn Tyr Thr Gly Ala Asp Gly Ala Arg Ile Asp
    50                  55

<210> SEQ ID NO 39
<211> LENGTH: 53
<212> TYPE: PRT
<213> ORGANISM: Arthrobacter globiformis

<400> SEQUENCE: 39

Asp Cys Leu Phe Asn Gly Leu Glu Thr Gln Thr Gln Ile Glu Asn Cys
1               5                   10                  15
```

-continued

Asp Leu Gly Gly Leu Asp Asp Leu Asp Gln Ser Asn Pro Val Val Ser
            20                  25                  30

Ser His Leu Met Ser Thr Tyr Lys Asp Trp Val Asp Met Gly Phe Asp
        35                  40                  45

Gly Ile Arg Val Asp
    50

<210> SEQ ID NO 40
<211> LENGTH: 53
<212> TYPE: PRT
<213> ORGANISM: Microbacterium laevaniformans OR221

<400> SEQUENCE: 40

Asp Cys Leu Phe Asn Gly Thr Glu Thr Gln Thr Gln Ile Glu Asn Cys
1               5                   10                  15

Asp Leu Gly Gly Leu Asp Asp Leu Asp Gln Ser Asn Pro Thr Val Ser
            20                  25                  30

Asn Tyr Leu Ile Asn Thr Tyr Lys Asp Trp Val Asp Met Gly Phe Asp
        35                  40                  45

Gly Ile Arg Val Asp
    50

<210> SEQ ID NO 41
<211> LENGTH: 53
<212> TYPE: PRT
<213> ORGANISM: Gardnerella vaginalis 409-05

<400> SEQUENCE: 41

Asp Cys Lys Phe Asp Asn Thr Glu Ser Gln Ser Asp Ile Glu Gln Cys
1               5                   10                  15

Asp Leu Gly Gly Leu Asp Asp Leu Asp Gln Ser Asn Pro Gln Val Ser
            20                  25                  30

Lys Tyr Leu Ile Lys Thr Tyr Lys Asp Trp Ile Asp Met Gly Phe Asp
        35                  40                  45

Gly Met Arg Val Asp
    50

<210> SEQ ID NO 42
<211> LENGTH: 53
<212> TYPE: PRT
<213> ORGANISM: Gardnerella vaginalis 5-1

<400> SEQUENCE: 42

Asp Cys Lys Phe Asp Asn Thr Glu Ser Gln Ser Asp Ile Glu Gln Cys
1               5                   10                  15

Asp Leu Gly Gly Leu Asp Asp Leu Asp Gln Ser Asn Pro Gln Val Ser
            20                  25                  30

Lys Tyr Leu Ile Lys Thr Tyr Lys Asp Trp Ile Asp Met Gly Phe Asp
        35                  40                  45

Gly Met Arg Val Asp
    50

<210> SEQ ID NO 43
<211> LENGTH: 52
<212> TYPE: PRT
<213> ORGANISM: Shuttleworthia satelles DSM 14600

<400> SEQUENCE: 43

Asp Ile Asp Asp Trp Asn Asn Glu Asn Gln Val Leu Asn Tyr Asp Leu
1               5                   10                  15

```
Gly Gly Leu Asp Asp Leu Asp Gln Ser Asn Pro Glu Ala Arg Lys Ala
            20                  25                  30

Ile Glu Asp Ala Tyr Tyr Gln Trp Val His Asp Thr Gly Ala Asp Gly
        35                  40                  45

Val Arg Ile Asp
    50

<210> SEQ ID NO 44
<211> LENGTH: 49
<212> TYPE: PRT
<213> ORGANISM: Xanthomonas axonopodis pv. citri str. 306

<400> SEQUENCE: 44

His Asn Pro Leu His Ala Phe Tyr Asn Thr Gly Gly Gly Leu Ala Glu
1               5                   10                  15

Leu Ser Asp Leu Asn Glu Asn Asn Pro Ala Val Leu Asp Tyr Leu Ala
            20                  25                  30

Gly Ala Tyr Leu Gln Trp Met Glu Gln Gly Ala Asp Ala Phe Arg Ile
        35                  40                  45

Asp

<210> SEQ ID NO 45
<211> LENGTH: 49
<212> TYPE: PRT
<213> ORGANISM: Xanthomonas campestris pv. campestris str. ATCC 33913

<400> SEQUENCE: 45

His Asn Pro Leu His Ala Phe Tyr Asn Thr Ser Gly Gly Leu Ala Glu
1               5                   10                  15

Leu Ser Asp Leu Asn Glu Asp Asn Pro Ala Val Leu Asp Tyr Leu Ala
            20                  25                  30

Gly Ala Tyr Leu Gln Trp Met Glu Gln Gly Ala Asp Ala Phe Arg Ile
        35                  40                  45

Asp

<210> SEQ ID NO 46
<211> LENGTH: 55
<212> TYPE: PRT
<213> ORGANISM: Aspergillus niger

<400> SEQUENCE: 46

Ile Thr Asp Trp Asp Asn Leu Thr Met Val Glu Asp Cys Trp Glu Gly
1               5                   10                  15

Asp Thr Ile Val Ser Leu Pro Asp Leu Asp Thr Thr Glu Thr Ala Val
            20                  25                  30

Arg Thr Ile Trp Tyr Asp Trp Val Ala Asp Leu Val Ser Asn Tyr Ser
        35                  40                  45

Val Asp Gly Leu Arg Ile Asp
    50                  55

<210> SEQ ID NO 47
<211> LENGTH: 341
<212> TYPE: PRT
<213> ORGANISM: Clostridium saccharoperbutylacetonicum

<400> SEQUENCE: 47

Met Lys Val Thr Ile Asn Asp Ile Ala His Ala Ala Asn Val Ser Lys
1               5                   10                  15
```

```
Ser Thr Val Ser Lys Val Ile Asn Asn His Lys Ser Ile Ser Glu Ser
            20                  25                  30

Thr Lys Leu Lys Val Arg Asn Ile Met Lys Glu Leu Asn Tyr Ile Pro
        35                  40                  45

Asn Asn Ser Ala Arg Gln Leu Ala Arg Gln Asn Ser Phe Asn Ile Gly
    50                  55                  60

Leu Leu Val Asp Ile Ser Arg Lys Glu Tyr Phe Leu Asp Phe Phe Phe
65                  70                  75                  80

Tyr Asn Ile Ile Gly Gly Val Glu Ser Ile Val Gly Ile Asn Asn Tyr
                85                  90                  95

Glu Leu Thr Leu Ser Asn Ile Asn Ser Leu Glu Cys Lys Ala Glu Phe
            100                 105                 110

Leu Asn Arg Leu Ile Tyr Ser Lys Lys Val Asp Gly Ile Ile Ile Pro
        115                 120                 125

Thr Ser Ile Val Asn Ser Glu Ile Ile Ser Lys Leu Asn Gly Leu Asn
130                 135                 140

Phe Pro Tyr Val Leu Ile Gly Gln Pro Lys Glu Phe Lys Asn Ser Thr
145                 150                 155                 160

Ser Trp Val Asp Val Asn Asn Thr Val Gly Gly Glu Leu Ala Thr Cys
                165                 170                 175

His Leu Ile Glu Gln Gly Tyr Lys Asn Ile Ala Phe Ile Gly Gly Lys
            180                 185                 190

Ser Asn Glu Ile Ile Ser Phe Asn Arg Leu Leu Gly Tyr Lys Asn Ile
        195                 200                 205

Leu Ser Lys Leu Asn Phe Thr Lys Asn Leu Tyr Ile Lys Glu Gly
210                 215                 220

Asn Ser Asp Lys Glu Ser Gly Tyr Glu Leu Thr Leu Gln Leu Leu Ser
225                 230                 235                 240

Asp Phe Pro Glu Ile Asp Ala Ile Leu Cys Ile Asn Asn Tyr Val Ala
                245                 250                 255

Phe Gly Val Leu Lys Ala Leu Lys Glu Lys Gly Leu Asn Ser Pro Thr
            260                 265                 270

Asp Ile Gly Ile Val Thr Phe Asp Asn Glu Pro Phe Ser Ala Tyr Thr
        275                 280                 285

Thr Pro Ser Leu Thr Cys Leu Asp Val Asp Thr Phe Lys Leu Gly Glu
290                 295                 300

Val Ala Ala Glu Ile Leu Met Lys Lys Ile Gln Asn Pro Asn Ser Gln
305                 310                 315                 320

Asn Glu Ile Thr Leu Ile Ser Pro Lys Leu Leu Ile Arg Glu Ser Ser
                325                 330                 335

Leu Leu Lys Lys Pro
            340

<210> SEQ ID NO 48
<211> LENGTH: 403
<212> TYPE: PRT
<213> ORGANISM: Clostridium saccharoperbutylacetonicum

<400> SEQUENCE: 48

Met Val Lys Lys Asn Lys Val Leu Ala Ser Ile Val Ala Ala Thr Leu
1               5                   10                  15

Val Ala Gly Thr Phe Val Gly Cys Gly Gly Thr Thr Ala Thr Ser Asn
            20                  25                  30

Asn Ala Lys Glu Ile Thr Val Trp Ser His Leu Lys Glu Lys Glu Ile
        35                  40                  45
```

Thr Glu Leu Thr Lys Val Ala Glu Lys Trp Gly Ser Glu Lys Gly Val
    50              55                  60

Lys Val Asn Val Val Asp Lys Gly Glu Met Gln Ala Tyr Ile Gln
65              70                  75                  80

Ala Ala Asn Ser Ser Lys Gly Pro Asp Ile Leu Phe Gly Val Pro Asn
                85                  90                  95

Asp Asn Leu Gly Thr Phe Gln Lys Ala Gly Leu Leu Ser Glu Val Pro
            100                 105                 110

Ser Gly Phe Ile Asp Glu Ser Lys Tyr Thr Ser Lys Gln Val Ile Asp
            115                 120                 125

Ser Val Thr Ile Glu Gly Lys Lys Tyr Ala Val Pro Leu Ala Ala Glu
            130                 135                 140

Thr Ser Ala Leu Phe Tyr Asn Lys Asp Lys Val Ser Glu Val Pro Lys
145                 150                 155                 160

Thr Met Glu Glu Val Val Glu Leu Gly Lys Lys Val Gly Phe Glu Tyr
                165                 170                 175

Asp Val Thr Asp Leu Tyr Arg Ser Tyr Gly Phe Leu Ala Ser Gln Gly
            180                 185                 190

Ser Tyr Ile Phe Lys Asn Asn Gly Thr Val Asp Ser Asn Asp Ile
            195                 200                 205

Gly Leu Gly Asn Glu Gly Ala Ile Lys Gly Tyr Gln Phe Ile Gln Asp
210                 215                 220

Leu Ile Val Lys Asp Lys Leu Met Ser Gln Asp Ile Thr Asp Asp Ile
225                 230                 235                 240

Ala Lys Ala Asp Phe Gln Ser Gly Lys Ser Ala Phe Tyr Ile Ser Gly
                245                 250                 255

Pro Trp Asp Ile Glu Ala Phe Lys Asp Ser Gly Ile Asn Phe Gly Ile
            260                 265                 270

Ala Pro Met Pro Thr Leu Gly Gly Lys Thr Val Ser Thr Leu Met Gly
            275                 280                 285

Val Gln Thr Ala Phe Val Ser Ser Lys Ser Pro Asn Gln Asp Leu Ser
290                 295                 300

Trp Glu Leu Met Lys Tyr Leu Met Glu Asn Ser Asp Asp Leu Met Ile
305                 310                 315                 320

Lys Gln Gly Asn Arg Ile Pro Val Ser Lys Ala Gly Ile Glu Ser Asp
                325                 330                 335

Ala Phe Lys Ala Ala Gly Asn Met Asp Val Phe Ala Lys Gln Leu Glu
            340                 345                 350

Val Ala Thr Ala Met Pro Asn Ile Pro Glu Ile Gln Thr Thr Trp Thr
            355                 360                 365

Pro Val Lys Asn Ile Ile Ser Leu Ile Ser Gly Ser Met Asp Ser
370                 375                 380

Lys Glu Thr Ala Lys Gln Ile Val Asp Gln Ile Lys Glu Gly Ile Lys
385                 390                 395                 400

Gln Gln Lys

<210> SEQ ID NO 49
<211> LENGTH: 416
<212> TYPE: PRT
<213> ORGANISM: Clostridium saccharoperbutylacetonicum

<400> SEQUENCE: 49

Met Lys Gly Glu Ile Ile Tyr Gln Ile Phe Pro Asp Arg Phe Asn Lys
1               5                   10                  15

Ser Arg Gln Asn Asn Val Glu Gly Leu Lys Glu Trp Glu Ser Glu
            20                  25                  30

Val Asp Gly Gln Cys Val Met Gly Asp Leu Ile Gly Ile Lys Glu
        35                  40                  45

Lys Leu Asp Tyr Leu Ser Lys Leu Gly Val Ser Ala Ile Tyr Leu Asn
50                  55                  60

Pro Ile Phe Gln Ala Asn Ser Asn His Lys Tyr Asp Thr Val Asn Tyr
65                  70                  75                  80

Tyr Asn Ile Asp Ser Ser Phe Gly Thr Leu Asp Asp Phe Arg Glu Leu
                85                  90                  95

Val Asp Ser Cys His Lys Lys Asn Ile Lys Val Ile Ile Asp Gly Val
            100                 105                 110

Phe Asn His Thr Ser Pro Asp Phe Phe Ala Phe Lys Asp Ile Leu Glu
            115                 120                 125

Asn Gln Glu Arg Ser Lys Tyr Lys Asp Trp Tyr Thr Ile Phe Ser Tyr
130                 135                 140

Pro Val Lys Val Glu Ser Pro Pro Asn Tyr Arg Asn Phe Gly Gly Cys
145                 150                 155                 160

Ile Asp Met Pro Arg Leu Asn Thr Glu Asn Val Glu Val Gln Lys Tyr
                165                 170                 175

Ile Val Asp Val Ile Lys Tyr Trp Glu Gly Met Lys Ile Asp Gly Leu
            180                 185                 190

Arg Leu Asp Val Pro Tyr Tyr Ile Glu Asp Ser Met Leu Glu Lys Ile
        195                 200                 205

Arg Lys Ser Thr Ser Leu Tyr Ile Val Gly Glu Ile Trp Gly Cys Gly
210                 215                 220

Lys Lys Phe Val Pro Gln Tyr Phe Asp Gly Val Met Asn Tyr Ser Phe
225                 230                 235                 240

Arg Asp Leu Val Gln Lys Ala Val Ile Arg Gln Ser Ile Asp Ala Ser
                245                 250                 255

Ile Phe Ile Asp Glu Trp Asn Phe Ile Glu Glu Thr Tyr Gly Gln Asn
            260                 265                 270

Ile His Cys Cys Phe Asn Met Ser Gly Ser His Asp Thr Glu Arg Ile
        275                 280                 285

Phe Asn Phe Cys Arg Gly Asp Ile Lys Arg Glu Lys Leu Phe Tyr Ala
290                 295                 300

Phe Leu Phe Leu Phe Pro Gly Met Pro Leu Val Tyr Tyr Gly Asp Glu
305                 310                 315                 320

Ile Gly Met Lys Gly Glu Asn Asp Pro Tyr Cys Arg Gly Thr Met Glu
                325                 330                 335

Trp Asn Glu Ser Lys Trp Asn Tyr Asp Ile Tyr Asn His Val Lys Gly
            340                 345                 350

Leu Ile Glu Leu Arg Asn Ser Ser Glu Ala Leu Gln Lys Gly Thr Ile
        355                 360                 365

Gln Phe Val Gly His Lys Glu Met Met Phe Ala Phe Glu Arg Val Tyr
370                 375                 380

Ala Glu Lys Arg Val Lys Val Phe Met Asn Phe Gly His Ser Lys Gln
385                 390                 395                 400

Ser Ile Asp Gly Phe Glu Leu Asp Gly Leu Ser Tyr Lys Val Ile Val
                405                 410                 415

<210> SEQ ID NO 50
<211> LENGTH: 310

<212> TYPE: PRT
<213> ORGANISM: Clostridium saccharoperbutylacetonicum

<400> SEQUENCE: 50

```
Met Lys Gln Ala Lys Thr Lys Ile Thr His Thr Leu Lys Ser Val
1               5                   10                  15

Pro Tyr Leu Leu Pro Ala Ile Ile Ser Ile Ile Phe Ser Ile Leu
                20                  25                  30

Pro Ile Leu Asn Thr Ile Tyr Leu Ala Phe Thr Asp Tyr Thr Met Tyr
                35                  40                  45

Ser Gln Gly Lys Ile Asn Phe Val Gly Ile Ala Asn Phe Lys Glu Val
            50                  55                  60

Phe Ala Gly Pro Phe Lys Glu Val Phe Pro Val Phe Ile Trp Thr
65                  70                  75                  80

Cys Val Phe Ala Thr Leu Ala Thr Ala Gly Thr Phe Leu Leu Gly Leu
                    85                  90                  95

Ile Met Ala Ile Leu Val Asn Asn Glu Asn Ile Lys Glu Arg Gly Leu
                100                 105                 110

Tyr Lys Ala Ile Leu Ile Ile Pro Trp Ala Leu Pro Ala Thr Val Ala
            115                 120                 125

Ile Leu Ser Trp Gln Gly Leu Leu Asn Gly Ser Tyr Gly Ala Ile Asn
        130                 135                 140

Asn Leu Leu Ile Ser Val His Ala Ile Ser Ala Pro Ile Pro Trp Leu
145                 150                 155                 160

Thr Asn Pro Leu Trp Ala Arg Ile Ala Ile Ile Val Thr Ile Trp
                165                 170                 175

Leu Gly Phe Pro Tyr Ala Met Asn Ile Cys Leu Gly Ser Leu Gln Ser
            180                 185                 190

Ile Pro Lys Thr Tyr Tyr Glu Ala Ala Asp Val Asp Gly Ala Ser Lys
        195                 200                 205

Phe Val Lys Phe Ile Lys Ile Thr Leu Pro Ser Leu Ala Gln Thr Ala
210                 215                 220

Tyr Pro Leu Val Ile Ser Ser Phe Ala Phe Asn Phe Asn Asn Phe Gly
225                 230                 235                 240

Gln Ala Tyr Leu Ile Thr Asn Gly Asn Pro Ala Arg Pro Gly Thr Gln
                245                 250                 255

Phe Ala Gly Phe Thr Asp Ile Leu Ala Ser Val Asn Tyr Lys Leu Ser
            260                 265                 270

Ile Thr Phe Gly Arg Tyr Glu Ile Ala Ser Thr Ile Ser Ile Ile
        275                 280                 285

Phe Ile Ile Leu Ala Thr Ile Ser Tyr Ile Gln Met Lys Ala Ser Gly
    290                 295                 300

Gln Phe Glu Glu Val Asp
305                 310
```

<210> SEQ ID NO 51
<211> LENGTH: 306
<212> TYPE: PRT
<213> ORGANISM: Clostridium saccharoperbutylacetonicum

<400> SEQUENCE: 51

```
Met Thr Ser Asn Ala Gly Asn Leu Lys Leu Asn Asn Thr Glu Gly Gln
1               5                   10                  15

Ser Glu Glu Ile Gln Asn Ile Lys Leu Lys Tyr Val Lys Leu Arg
                20                  25                  30
```

-continued

```
Pro Ala Glu Ile Arg Thr Ala Trp Ile Ser Arg Ile Val Leu Trp Ile
             35                  40                  45
Met Ile Val Ile Val Leu Ile Pro Ile Met Ala Val Ser Ala Ser
 50                  55                  60
Met Ala Lys Gly Asn Ser Phe Thr Gln Thr Ser Ile Phe Pro Lys Ser
 65                  70                  75                  80
Phe Thr Leu Glu Asn Tyr Val Lys Val Ile Thr Gln Thr Lys Phe Leu
                 85                  90                  95
Ile Trp Ala Arg Asn Ser Leu Val Val Cys Phe Ser Val Ala Met Met
            100                 105                 110
Gln Leu Ile Met Thr Ile Pro Ala Ala Phe Ala Phe Ser Lys Leu Arg
        115                 120                 125
Phe Lys Gly Arg Lys Phe Gly Leu Met Thr Leu Leu Ile Leu Gln Met
130                 135                 140
Phe Pro Asn Thr Met Ala Leu Pro Ala Ile Leu Ser Val Ala Tyr Asn
145                 150                 155                 160
Ile Arg Gly Gly Met Asp Asn Leu Leu Pro Leu Ile Leu Ile Ile Ser
                165                 170                 175
Val Gly Ser Ala Tyr Asn Ile Trp Leu Met Lys Gly Tyr Met Asp Gly
            180                 185                 190
Ile Pro Lys Glu Leu Thr Glu Thr Ala Tyr Ile Asp Gly Ala Thr Thr
        195                 200                 205
Phe Gln Ala Phe Ile Lys Val Val Leu Pro Leu Ile Lys Asn Met Ile
210                 215                 220
Ile Val Ile Phe Ile Phe Ala Phe Val Gly Ala Tyr Ser Glu Phe Leu
225                 230                 235                 240
Phe Thr Ser Ala Leu Ile Lys Asp Gln Tyr Thr Glu Thr Leu Ala Thr
                245                 250                 255
Gly Met Gln Gly Phe Ile Lys Asp His Phe Ser Ala Asn Trp Thr Gln
            260                 265                 270
Tyr Ser Ala Ala Ala Ile Met Ala Ser Leu Pro Val Val Leu Ile Ser
        275                 280                 285
Val Phe Ser Gln Lys Phe Phe Ala Lys Gly Leu Thr Ala Gly Ser Val
290                 295                 300
Lys Gly
305
```

<210> SEQ ID NO 52
<211> LENGTH: 53
<212> TYPE: PRT
<213> ORGANISM: Clostridium saccharoperbutylacetonicum

<400> SEQUENCE: 52

```
Leu Ile Leu Asn Asp Lys Ser Lys Glu Leu Ser Leu Ala Ile Ser Asn
 1               5                  10                  15
Val Asn Glu Thr Leu Gly Lys Ile Asp Leu Gly Thr Ile Asp Ser Thr
             20                  25                  30
Asn Asn Leu Glu Ser Leu Val Leu Asn Met Glu Glu Val Ser Asn Pro
         35                  40                  45
Met Ile Lys Val Ala
     50
```

<210> SEQ ID NO 53
<211> LENGTH: 586
<212> TYPE: PRT
<213> ORGANISM: Clostridium saccharoperbutylacetonicum

<400> SEQUENCE: 53

Met Arg Phe Glu Ala Val Tyr His Arg Ala Ser Asp Asn Leu Cys Tyr
1               5                   10                  15

Ser Ile Asp Lys Asp Asn Leu Ile Val Asn Ile Lys Thr Gly Tyr Asp
            20                  25                  30

Val Glu Lys Val Phe Ile Tyr Tyr Gly Asp Pro Phe Asp Gly Gly Ile
        35                  40                  45

Leu Gly Gly Glu Trp Lys Trp Lys Gly Lys Arg Glu Glu Ile Pro Phe
    50                  55                  60

Lys Lys Arg Leu Lys His Gln Ile Trp Trp Thr Thr Thr Leu Lys Leu
65                  70                  75                  80

Lys Tyr Lys Arg Cys Lys Tyr Tyr Phe Glu Leu Thr Gly Asn Glu Glu
                85                  90                  95

Thr Trp Phe Tyr Phe Glu Asp Cys Phe Leu Ser Glu Lys Gln Met Gln
            100                 105                 110

Leu Asp Gly Lys Met Leu Gln Cys Phe Thr Phe Pro Trp Met Asn Glu
        115                 120                 125

Ala Asp Ile Asn Lys Thr Pro Ala Trp Val Asn Asp Met Val Trp Tyr
130                 135                 140

Gln Ile Phe Pro Glu Arg Phe Cys Asn Gly Asn Pro Ser Ile Asn Pro
145                 150                 155                 160

Lys Gly Val Gln Pro Trp His Lys Gly Gly Val Thr Asn Glu Glu Phe
                165                 170                 175

Tyr Gly Gly Asp Leu Gln Gly Ile Ile Asn Lys Leu Asn Tyr Leu Lys
            180                 185                 190

Glu Ile Gly Ile Thr Gly Ile Tyr Leu Asn Pro Ile Phe Glu Ser Pro
        195                 200                 205

Ser Ala His Lys Tyr Asp Thr Thr Asp Tyr Met Lys Ile Asp Pro Asn
210                 215                 220

Phe Gly Asp Glu Asn Val Phe Arg Lys Leu Val Asn Lys Ala His Glu
225                 230                 235                 240

Lys Gly Ile Arg Ile Met Leu Asp Gly Val Phe Asn His Cys Gly Ala
                245                 250                 255

Lys Phe Gly Pro Trp Leu Asp Val Leu Glu Asn Gly Pro Ser Ser Lys
            260                 265                 270

Tyr Tyr Ser Trp Phe Met Val Asn Lys Trp Pro Phe Asp Asp Asn Asn
        275                 280                 285

His Asp Thr Lys Asp Gly Arg Phe Tyr Ser Phe Ala Phe Asn Gln Lys
290                 295                 300

Met Pro Lys Leu Asn Thr Asn Asn Pro Glu Val Ile Asp Tyr Leu Ile
305                 310                 315                 320

Lys Val Cys Glu Tyr Trp Val Lys Asn Tyr Lys Ile Asp Gly Leu Arg
                325                 330                 335

Leu Asp Val Ala Asn Glu Ile Ser His Lys Phe Cys Lys Lys Leu Arg
            340                 345                 350

Glu Lys Met Lys Ser Leu Asn Pro Asp Phe Tyr Ile Leu Gly Glu Ile
        355                 360                 365

Trp His Asp Ser Ile Pro Trp Leu Arg Gly Asp Glu Phe Asp Ala Ile
    370                 375                 380

Met Asn Tyr Ser Leu Thr Ser Ser Ile Ser Asp Phe Trp Ile Asp Lys
385                 390                 395                 400

Ser Leu Thr Lys Asp Asp Phe Glu Tyr Thr Ile Asn Arg Cys Tyr Thr

```
                    405                 410                 415
Ile Tyr Met Gln Gln Asn Asn Asp Val Leu Phe Asn Leu Leu Asp Ser
            420                 425                 430

His Asp Thr Glu Arg Leu Ile Ser Arg Val Lys Asp Ile Asn Val Phe
        435                 440                 445

Tyr Gln Gln Leu Ala Val Leu Phe Thr Met Pro Gly Ser Pro Cys Ile
    450                 455                 460

Phe Tyr Gly Thr Glu Val Ala Leu Gly Lys Tyr Asp Pro Asp Cys
465                 470                 475                 480

Arg Arg Cys Met Pro Trp Asp Glu Ile Lys Ser Gly Ile Tyr Asp Asp
                485                 490                 495

Lys Ile Asn Ile Met Lys Ala Leu Ile Asn Leu Arg Lys Glu Gln Lys
            500                 505                 510

Leu Phe Arg Ser Arg Asn Phe His Phe Pro Asn Thr Ile Lys Asn Ser
        515                 520                 525

Arg Val Ile Glu Tyr Ile Lys Ile Asp Glu Asn Gly Asn Arg Leu Glu
    530                 535                 540

Ile Leu Leu Asn Cys Ser Asn Ile Asp Val Leu Ile Glu Asn Asn Gly
545                 550                 555                 560

Ser Val Leu Phe Ser Asn Leu Tyr Ser Asn Arg Leu Leu Lys Lys
                565                 570                 575

Gly Val Leu Ile Arg Lys Val Asp Ser Ile
            580                 585

<210> SEQ ID NO 54
<211> LENGTH: 671
<212> TYPE: PRT
<213> ORGANISM: Clostridium saccharoperbutylacetonicum

<400> SEQUENCE: 54

Met Glu Leu Thr Tyr Arg Phe Gly Arg Gly Tyr Trp Arg Asn Ile Lys
1               5                   10                  15

Glu Gly Asn Glu Arg Glu Trp Met Ile Gly Asn Gly Ile Gly Gly Tyr
            20                  25                  30

Ser Ser Gln Thr Ile Ile Asn Ser Gly Phe Arg Cys His Asn Gly Tyr
        35                  40                  45

Leu Ile Ala Ala Met Asn Pro Pro Val Glu Arg Tyr Ser Ile Leu Tyr
    50                  55                  60

Arg Thr Gln Glu Lys Ile Val Thr Asp Gly Arg Thr Tyr Asp Leu Thr
65                  70                  75                  80

Cys Gln Glu Tyr Lys Asp Tyr Thr Lys Asn Gly Tyr Glu Tyr Leu Lys
                85                  90                  95

Ser Phe Ile Phe Asp Ser Val Pro Gln Tyr Ile Tyr Gln Ile Glu Asp
            100                 105                 110

Ile Asn Val Lys Lys Thr Ile Ala Met Glu Tyr Gly Tyr Asn Thr Val
        115                 120                 125

Ala Ile Cys Tyr Glu Ile Glu Asn Gly Ser Ser Lys Ala Lys Ile Asp
    130                 135                 140

Ile Thr Pro Leu Phe Asn Phe Lys Glu Ala Gly Thr Phe Lys Ala Ser
145                 150                 155                 160

Glu Gln Leu Asp Phe Lys Thr Glu Leu Gln Asp Ile Leu Lys Leu
                165                 170                 175

Tyr Pro Asn Glu Asp Asp Lys Lys Ile Ile Ser Phe Met Ser Ser Ala
            180                 185                 190
```

```
Gly Ile Phe Lys Asp Arg Ser Leu Ile Lys Val Gln Asn Asp Phe Asn
            195                 200                 205
Tyr Asn Pro Leu Ile Glu Glu Asn His Tyr Tyr Glu Phe Glu Asn Arg
210                 215                 220
Asn Gly Phe Ile Gly Leu Asn Asn His Tyr Thr Pro Tyr Asp Ile Glu
225                 230                 235                 240
Ile Glu Leu Glu Pro Phe Glu Thr Lys Lys Phe Tyr Leu Lys Cys Thr
                245                 250                 255
Val Glu Glu Leu Gly Asp Lys Asp Gly Phe Asp Ile Val Lys Glu Tyr
                260                 265                 270
Lys Glu Arg Thr Asn Glu Leu Leu Asn Arg Ser Gly Tyr Lys Asp Phe
            275                 280                 285
Phe Ala Leu Asn Leu Val Lys Ala Ala Asp His Phe Ile Val Asp Arg
290                 295                 300
Lys Ser Thr Gly Leu Lys Thr Ile Leu Ala Gly Phe Pro Trp Phe Val
305                 310                 315                 320
Asp Trp Gly Arg Asp Thr Met Ile Ala Phe Glu Gly Leu Thr Leu Cys
                325                 330                 335
Thr Lys Arg Phe Glu Asp Ala Arg Glu Ile Leu Lys Ser Phe Ala Glu
                340                 345                 350
Tyr Ile Lys Asp Gly Leu Val Pro Asn Val Phe Ala Asp Lys Gly Thr
            355                 360                 365
Gln Ala Phe Tyr Asn Thr Ala Asp Ala Ser Leu Trp Tyr Ile Gln Ala
370                 375                 380
Val Tyr Lys Tyr Leu Lys Tyr Thr Gly Lys Lys Ser Asp Phe Lys Phe
385                 390                 395                 400
Val Asn Asp Lys Leu Phe Asp Lys Leu Ile Glu Ile Asp Ala Tyr
                405                 410                 415
Ser Asn Gly Thr His Phe Ser Ile Gly Met Asp Asp Cys Leu Ile
            420                 425                 430
His Ala Gly Ser Gly Leu Asp Gln Val Thr Trp Met Asp Val Arg Val
                435                 440                 445
Asp Glu Met Val Val Thr Pro Arg His Gly Lys Pro Val Glu Ile Asn
450                 455                 460
Ala Leu Trp Tyr Asn Ala Leu Cys Ile Met Asp Trp Leu Cys Arg Lys
465                 470                 475                 480
Tyr Glu Met Asn Gly Ser Lys Tyr Glu Ser Leu Ala Arg Lys Val Lys
                485                 490                 495
Asn Ser Phe Asn Lys Lys Phe Trp Asn Glu Lys Glu Gln Cys Leu Phe
            500                 505                 510
Asp Val Val Asp Asp Tyr Asp Gly Lys Val Arg Pro Asn Gln Ile Trp
515                 520                 525
Ala Val Ser Leu Pro Phe Thr Met Leu Glu Lys Glu Lys Glu Ala Lys
530                 535                 540
Val Val Asn Lys Val Tyr Lys Glu Leu Tyr Ser Thr Tyr Gly Leu Arg
545                 550                 555                 560
Ser Leu Ser Tyr Leu Asp Lys Asp Phe Lys Ser Glu Tyr Ile Gly Pro
                565                 570                 575
Leu Met Lys Arg Asp Leu Ala Tyr His Met Gly Thr Thr Trp Ala Phe
            580                 585                 590
Leu Ile Gly Ser Phe Ile Ser Ala Tyr Cys Lys Val Asn Asn His Ser
            595                 600                 605
Lys Glu Ala Val Ser Arg Ala Lys Glu Met Cys Glu Val Phe Gln Asp
```

```
                    610             615               620
His Met Lys Asp Gly Cys Ile Asn Gly Ile Ala Glu Val Phe Asp Gly
625                 630             635                 640

Lys Phe Ser Ala Thr Gly Arg Gly Cys Tyr Ser Gln Ala Trp Ser Val
                645             650                 655

Gly Glu Val Leu Arg Ala Tyr Thr Asn Asp Val Leu Pro Phe Ile
            660             665             670

<210> SEQ ID NO 55
<211> LENGTH: 13357
<212> TYPE: DNA
<213> ORGANISM: Clostridium saccharoperbutylacetonicum

<400> SEQUENCE: 55
tgcaaagtag atcaaataaa tggcagtaca tcgttagtat atgctcttaa aacttcgcct      60
acactccagg cttgactata gcatccctg cctgtagctg aaaattttcc atcaaatact     120
tcagctattc catttatgca tccatctttc atatgatcct gaaatacttc acacatttct     180
tttgctctac ttactgcttc tttagagtga ttatttacct tacaatatgc tgatataaag     240
ctccctatta agaatgccca tgttgtcccc atatgatatg ctaaatccct tttcataagt     300
ggtcctatat attcgctctt aaaatcttta tctaagtatg acagcgatct caatccataa     360
gtcgaatata attctttata tactttattc acaactttcg cttcctttc ttttctaac      420
atagtaaatg gcaatgatac tgcccatatt tgatttggcc taactttccc atcataatca     480
tcaacaacat caaataaaca ctgttctttt tcattccaga attttttgtt aaaggagttt     540
ttaactttc tcgctaaact ttcatatttt gatccattca tttcatactt tctacataac     600
caatccatta tgcaaagggc attataccaa agagcattta tttctactgg tttaccatgc     660
cttggagtaa caaccatttc gtctactctt acatccatcc acgttacttg atccaatccg     720
ctgccagcat gaataagaca atcatcatcc atacctattg aaaaatgtgt gccatttgaa     780
taagcatcaa taatttcaat taacttgtcg aataatttat cattaacaaa cttaaaatca     840
cttttctttc cagtatattt taaatactta tacagcttt gtatatacca taatgatgca     900
tctgcagtat tgtaaaacgc ttgtgttcct ttatccgcaa aaacatttgg aacaagtcca     960
tcttttatat attctgcaaa agactttaat atttctcttg catcctcaaa tctctttgta    1020
cacagcgtta aaccttcaaa agctatcata gtgtctctcc cccaatcaac aaaccaagga    1080
aatcctgcaa gtattgtttt caatccagta cttttttctat ctacaataaa atggtcagct    1140
gcttttacta aatttaatgc aaaaaaatct ttatagcctg atctattcaa taattcattt    1200
gttctttcct tatattcttt aacaatatca aatccgtctt tatcacctaa ctcttctact    1260
gtacatttta aataaaactt tttagtttca aaaggctcta attcaatttc aatatccat     1320
ggcgtataat gattatttaa cccaataaat ccatttctat tttcaaattc atagtaatga    1380
ttctcttcaa ttaatggatt ataattaaaa tcattctgta cttttataag acttctgtcc    1440
ttaaatatgc ctgctgatga cataaaactt attatcttct tatcatcttc attaggatac    1500
aatttttaata tatcgtcttg taattcagtt ttaaaatcca gctgctcaga agccttaaat    1560
gtaccagctt cctaaaaatt aaacagtggt gtaatatcaa ttttagcctt agaacttcca    1620
ttttcaatct cataacatat agctacagta ttatatccat attccatagc tatagttttt    1680
tttacattta tatcttctat ttgataaata tattgaggca ctgaatcaaa tataaaactt    1740
ttgagatact cataaccatt cttcgtataa tccttatatt cctgacaagt caaatcatat    1800
```

```
gttcttccat ctgtgacgat ttttcctga gttctatata atattgaata acgttctact    1860
ggcggattca ttgctgctat taaatacca ttatgacatc taaatccact attaatgata    1920
gtttgactgc tatacccgcc aataccattg cctatcatcc attctctctc gtttccttcc    1980
tttatatttc tccagtatcc tcttccgaac ctatatgtta attccatgac tactcctctt    2040
caaaattatt ttttcattta taattaataa gtacatattg ctgatttaat taaatatctt    2100
tttcatttat aaataaaatc aaatcgcaaa atggatattt tttatcagcc catgatgtaa    2160
acggacttgt tatttatttg attgaacctt atatagaatc aaccttccta attaatacac    2220
cttttttaag cagtctatta ttagaatata aattactaaa caaaacacta ccattattct    2280
ctattaaaac atctatattt gaacaattta gtaaaatttc taacctattc ccattttcat    2340
ctattttaat atattctatt accctgctat ttttaattgt atttggaaaa tgaaaattac    2400
ggcttctaaa taatttttgc tcttttctta aattaatcaa cgccttcatt atattaatct    2460
tatcatcata aattccactt tttatttcat cccatggcat acatcttcgg caatcgggat    2520
catactttcc ttcaagtgca acttctgtac cataaaatat gcatggactt cctggcatcg    2580
taaatagtac agctagctgt tgataaaata cgttaatgtc ttttactctt gaaattaagc    2640
gttctgtatc atgagaatcc aacaaattaa ataacacatc attattttgc tgcatatata    2700
ttgtatagca tctatttatt gtgtactcaa aatcatcctt agttaaactc ttatctatcc    2760
agaagtctga tatactacta gttagtgaat aattcataat agcatcaaat tcatcacctc    2820
taagccaagg aatagaatca tgccatattt cacctaaaat atagaagtct ggatttaacg    2880
atttcatttt ttctctaagc ttcttacaga acttatgcga aatttcattt gcaacatcta    2940
atcttaatcc atcaatctta taattttta cccaatactc acatacctta attaaataat    3000
caattacttc tggattattt gtatttaatt ttggcatttt ctgattaaag gcaaaagaat    3060
aaaatcgtcc atcctttgta tcgtgattat tatcatcaaa aggccactta tttaccataa    3120
accaactata atatttggaa ctaggaccat tttcaagtac atctaaccat ggtccaaact    3180
tagctccaca atgattaaac actccatcaa gcataatcct aatcccttt tcatgtgctt    3240 tatttacaag ctttctaaat acattttcat ctccaaaatt aggatctatt ttcatataat    3300
cagttgtatc atatttatgt gctgacggag attcgaatat tggatttaaa tatatgcctg    3360
taattcctat ttcttttaaa taatttaatt tatttattat ccctgcaaa tccccaccat    3420 aaaactcttc atttgtaacg cctccttat gccaaggctg gacccctttg ggattaattg    3480
aaggatttcc attacaaaaa cgctctggga atatctgata ccaaaccata tcatttaccc    3540
atgctggtgt tttatttata tcagcttcat tcatccatgg aaatgtaaaa cattgcaaca    3600
tttttccgtc caattgcatt tgttttcac ttaaaaaaca atcttcaaaa taaaaccagg    3660
tttcttcatt ccccgttaat tcaaaatagt atttacatct tttatacttc agtttcaaag    3720
tagttgtcca ccatatttgg tgctttaatc tctttttaaa tggaatttct tctcttttc    3780 ctttccattt ccattcgcca cctaaaattc ctccatcaaa tggatcacca taatatataa    3840
acactttttc tacatcataa ccagtcttta tatttacaat taaattgtct ttatcaattg    3900
aataacataa gttatctgag gctctatgat atacagcttc gaatctcata agaattcctt    3960
ccccttttca cttatatata actattacgc tactttgatc attggatttg atacctcctc    4020
catatttaac actaaagatt ccaaattatt tgtagaatct atagttccaa gatcaatctt    4080
gcctaaagtc tcatttacat tagatatagc taacgataat tccttacttt tatcatttaa    4140
aatcaatgat tctgaattca catcttcagc ttatgaatta acattactta ataaaattaa    4200
```

```
ttttaataaa agtaacgctg caaataatta ttattggaat aattgaaata cagaacatac    4260
tttccaataa tttaaaatgc aaacttttag atttttttaat agttacatca ttgttttttg    4320
aattttcttt agttgaaaga tttttataga aaaacttttt aattttatta aaattgctac    4380
ttattttcta atccttagtt ggcttcatta tatactcacg tccccacttt agccttttac    4440
tgatccagca gttaatcctt ttgcaaagaa ttttttgtgaa aatactgata tcaaaacaac    4500
tggtaatgat gccattattg cagccgctga atattgagtc cagttagctg aaaaatgatc    4560
tttaatgaat ccttgcatac ctgttgctag agtttctgta tattgatctt ttataagagc    4620
tgatgtaaat aaaaattcgc tataagctcc aacaaaagca aatataaata ttactattat    4680
catattcttt attagtggca atactacctt aatgaaagct tgaaaagttg ttgctccatc    4740
tatatatgca gtttcagtta attcttttgg aattccatcc atgtatccct tcataagcca    4800
gatgttatat gcactaccta ctgatataat taatattaat ggtaataaat tatccattcc    4860
accccgaata ttatatgcaa cacttaaaat tgctggtaat gccattgtat ttggaaacat    4920
ctgtaatatc aaaagtgtca taagtccaaa ttttctacct ttaaacctaa gcttagaaaa    4980
cgcaaaagct gctggaattg tcatgattag ctgcatcata gcaacgctaa aacaaacaac    5040
taatgaattt cttgcccata ttaaaaactt agtttgagtt attactttta cataattctc    5100
taaagtaaat gatttaggaa aaatagaggt ttgcgtaaat gaattacctt tagccataga    5160
tgctgaaaca actgccatga ttggaataag aactattaca atcataatcc aaagtactat    5220
ccttgaaatc catgcagttc ttatttctgc tggtcttaat ttttttacat attttaattt    5280
tatgttttgt atttcttcac tttgtccttc tgtattattt aatttcaaat tccctgcatt    5340
tgatgtcatt ttaatcaacc tcctcaaatt gtcctgatgc tttcatttgt atgtatgaaa    5400
ttgtagctaa aattataaat ataataatgc ttatagtgga agcaatttca tatcttccaa    5460
atgttattga caatttataa tttactgaag ccaatatatc tgtgaaacct gcaaattgtg    5520
ttccaggtct tgccggatta ccattagtaa ttaaatatgc ttgaccaaaa ttattaaagt    5580
taaatgcaaa ggatgaaata actaatggat atgctgtttg tgcaagcgaa ggtaaagtta    5640
ttttaataaa ttttacaaac ttgctggctc catcaacgtc agctgcttca taatatgttt    5700
taggtatcga ttgaagtgaa cccaaacaaa tattcatggc atatggaaat cctagccata    5760
tagttactat gattattgca attcttgccc ataatggatt agttaaccat ggaataggcg    5820
ctgaaatagc atgtacactt ataagtaaat tattaattgc cccataactt ccatttaata    5880
aaccttgcca tgaaagtatt gcaacagtag ctggtaatgc ccatggaata attaaaattg    5940
ctttataaag ccctcgttct tttatatttt cattatttac aagaattgcc ataattagtc    6000
ctaacaaaaa tgttcctgca gttgccaatg tagcaaagac acatgtccat ataaataccg    6060
gaaaaaatac ttctttaaat ggaccagcaa atacttcttt aaaatttgca attcctacaa    6120
aattaatttt tccttgtgaa tacatagtat agtctgtaaa tgccaaatat attgtattaa    6180
gtattggtaa tattgaaaat ataattattg aaataatggc tggtaataaa tacggcactg    6240
atttcaaagt atgtgttatt ttttttgttt tggcttgttt cataattgcc cacctctttg    6300
atataaaaaa atttaaatct agtatttctt aatcttactt tttttatata aataatttat    6360
ttaatctctt atgtcaatat cactaaaata tattatacta attgaattta ctaataaagc    6420
caaatttaaa tatatgcctt tttctctatg atttttatca tggaaaaaaa taaaattaat    6480
gaaatttatt catatatttta tccaaacaga taaacatatt gtgataacca atgtccaatt    6540
```

```
aaagaacatt gattgtttaa agttgctatt ttataacttg caaagttatc cttgaatgct    6600
aaactataac tttataacta agaccatcta gttcaaatcc atcaatagac tgtttgctat    6660
gtccaaaatt cataaatact ttaactcttt tttctgcata cactctttca aatgcaaaca    6720
tcatttcttt atgtccaaca aattgtatag tcccttttg caatgcttca ctactatttc     6780
taagttctat taaaccttt acatgattat atatatcata attccattta ctttcattcc     6840
attccatagt tcctctacaa taagggtcat tttctccttt catacctatt tcatctccat    6900
aatatacaag aggcattcct gggaataaaa ataaaatgc atagaataat ttttctctct     6960
ttatatctcc tctgcagaaa ttaaaaatcc tttctgtatc atgacttcca gacatattaa    7020
agcagcaatg tatattctgc ccgtatgttt cttctatgaa attccattca tctatgaata    7080
ttgatgcatc aatgctttgt cttataactg cttttttgcac taaatctcta aatgaataat   7140
tcattactcc atcaaaatat tgaggcacaa atttcttgcc acaccccat attcaccta      7200 ctatatataa gctagtagat tttcttattt tttctaacat agagtcttca atataatatg    7260
gtacatctag tcttaatcca tctatttca tcccttccca atacttaata acatcaacta     7320 tatactttg aacttcaaca ttttcagtat taagacgcgg catatctata catcctccaa     7380
aatttctata attaggtgga cttccactt taactgata actaaaaata gtataccaat      7440
ccttatattt tgatctttct tgattttcta atatatcttt gaaagcaaaa aaatctgggc    7500
tagtatggtt aaaaactcca tcaataataa ctttatatt tttttatga catgaatcta     7560 ctaattctct aaaatcatct aaagttccaa aagaactatc tatattataa tagttaacag    7620
tatcatactt atgattagaa tttgcctgaa aaattggatt taaataaatt gcactaacac    7680
cgagttttga tagataatca agtttctctt taattccaat taaatcacct cccataacac    7740
attgtccatc aacttcactt tcccattctt ttaaaccttc aacattatta ttttgtcttg    7800
atttattaaa tctgtctgga aaaatttgat atattattc acctttcatc aattattcct    7860 cctaattta acattattat ctacctatat ttcgcttcaa ttatggaaac atggatttta    7920
taaggcttta ggatctaacc atgcggtttt tccatttaga agcgaaaagt agatatttaa    7980 tattttgtg tgccaaatat aatatgcatg atgaaattt tctttaaatt aacatttata    8040
tttaacgatt tacagtacta tcaatcccag agtctatagc tgctgatgta gttgtattaa    8100
cgctcttcaa attactcttt acaccatcat ttatataatc ttctgcctta gtcacttta    8160 cattccaatt ctgtccacca ttattatccc aatagtctgt tggtgaaata atatgaatac    8220
agtaatttag aatatcatta ttatttactg taatagttgc ttcaaattct ccattggaat    8280
tcttagtcat atttacatct tgaatgtttt tccatccatt agttccataa tgaagtgtta    8340 cttttttgtgc attagtattc ttatatgaaa ctttatattg tacgttcttt tgatctggat    8400
ttggtgtttc attattaaca acataaatct tcccactatt ttctcctaaa ttcactgata    8460 tttgtttcc tgtaacacct ccttgttgaa ctgtgatcga atcatttaca tcaaaaagat    8520
ttacaaattt atctccaact tttatagtac tttcagctct aattggaatg gtcgcacttt    8580
gatctccatc tgaattatta aatacattta caacttcttg tccaacattt tctcctgaat    8640
ccatccttct tgagaatgca tataaatgtg gtgaagacca catttctctt tgagtacctt    8700
ctcttaaggc ttcatatttt tgcctaaatg aattcaattt gttaattagt ttataagtat    8760
ctgtattctc attaaaataa tctgtaatta catttccatt gtaatccttt ttaaccattg    8820
accaacgatt ccatgtatct gcaataccat ttatacttgc tccatttgca ttacctttgt    8880
tttgttctgt accttgaaat actgttggta cccctcttac agtaaacatg aaaacaagtg    8940
```

```
cattttgaag ttttttaca ttaccatttg ctactgttaa aaatctatta cgatcatgat      9000
tatctataaa agtcaccata tgatttgcat aaccattata tttattgtct tgtgctaaaa      9060 tattttaat agagcaagta cctgatgatg acatgtcatc aaaagattgt cctgatgcaa      9120
aatcattatt tattgcttga tataatggaa aatctagcat tccccattct gcatcggatc      9180
caacccactt cttcacaaaa tctacattca tatcaaaatt ttctccaaaa gtattaactc      9240
ctatatactt ttgtaactcg ttaatataag atggtttcat acattttgct gcgtcaaccc      9300
ttgctgcatc agctccagta taatcaaacc atgacttaat agcattattc atagctgcct      9360
tagcatcaga attatcttga tttaaatcat ctaaaccgcc caaatcatga tcatctaaca      9420
tttggggatc agagtgttct cttgaccaat caatatcgcc attatgatga taccaatttg      9480
gattattaaa aggtgctgcc ggctcaaacc ccttgatgtc ataataagct tgttttccta      9540
acatataatc cccaacatga tttggaacta tatctattat tactttaatc ccctttttcgt     9600 gagctttatc tactaactcc tttagctttt cttttgttcc aaaataagga tttgccttat      9660
tgggatcttt cacattatat ccatgataag ctgtaggcca tacttttcct gtgccatcag      9720
ctctagacca catttgtggt tccgcaaccg gtgatatcca aatggctgag tatcccatgc      9780
ccttaatata atctaactta tcaataacac cttgccaatc tccgccgtgc atatatctaa      9840
aatcatcttc aagattttct gtattacgaa atgcatctcc tgtagcatta tttgttttat      9900
ctccatcata aaatctgtct accataattt gataaatagt atcgttttca cttagatttc      9960
caattgccgc ttgtgccttg cttccactca taaacatgtt agtgcttgaa acaattgttg     10020
caactaagat agataatatt accttgttaa attttcttct aaacataact ttcccccact     10080
attatatatt tttattagtc attcacataa ttatgaaaaa ctaataaatg attttataaa     10140
attaccttgt cataatttca tcaaaataag cacataaaaa tcaaaaatat cgtcgtcttc     10200
gcattccttt atttctttaa atgtattaca ttaggtaaac cggtttccct atttagtata     10260
ctaccatctt aaatggattt caatacattt ctgaaaacat ttaccaatat aattacatag     10320
aatgtacact aaactccact atatagctag agaacttctt ttggcttgtg tattttgaaa     10380
atattaatat taaaaagatg ctaaagttaa ttgttttcaa tcactttagc actacatgtt     10440
attttcttaa tttacttttt tattttgtt gctttatacc ttctttaatt tgatctacta     10500
tttgttttgc agtttctttc gaatccattg atccgcttat taaagatatt atattatttt     10560
ttaccggagt ccaagtagtt tgaatttctg gaatattagg cattgctgta gcaacttcta     10620
attgtttagc aaatacatcc atgtttccgg ccgctttaaa cgcatcactt tctataccgt     10680
cttttgaaac tggaattcta tttccttgct taatcattag gtcatcacta ttttccataa     10740
gatacttcat taactcccat gataagtctt gattaggtga ctttgaactt acaaatgcag     10800
tttgaactcc catcaatgtt gaaacagttt tcccacctaa tgttggcatt ggagctatac     10860
caaaattaat tcctgaatct ttaaatgctt ctatatccca tggtcctgaa atataaaatg     10920
ctgatttacc tgattggaaa tctgctttag ctatatcatc agtaatatct tgagacatta     10980
atttgtcttt aacaattaaa tcttgaatga attgatatcc ttttatcgca ccttcattgc     11040
ctaatccaat atcgtttgaa tcaacagttc cattattatt tttaaaaata tagctacctt     11100
gcgatgctaa aaatccataa cttctgtata aatcagttac atcgtattca aatcctactt     11160
ttttgcctaa ttcaacaact tcttccatag ttttggtac ttctgaaact ttatctttat     11220
tataaaatag agcactagtt tcagctgcta atggaactgc atatttttt ccttctatag     11280
```

```
tcactgaatc tattacttgt ttagatgtat atttactctc atctataaaa ccacttggca   11340
cttctgaaag taaaccagct ttttgaaatg ttcctaagtt atcattaggt acaccaaaaa   11400
gtatatctgg acctttagaa ctattagcgg cttgtatata tgcttgcatc tcccctttat   11460
catctacaac attaaccttaa actcccttttt cacttcccca tttttccgct actttagtaa   11520
gctctgtaat ctcttttttct ttcaaatgtg accaaactgt aatttcttta gcattattac   11580
ttgtagctgt tgttcctcca catcctacaa atgttcctgc aactaaagtt gctgccacga   11640
ttgatgctaa tactttattt tttttttacca tttttcaatt ctccctccta atttataatc   11700
ttttacagaa aatatttact tcttgtaact actaggctta taaacaaaat actaaaaatc   11760 atcttttttat taattcattc aaataagcat attataaagt tgaaaattat attcttctgt   11820
cttacaaatt ctttaaatac attgaaaatt taagaaaccg gtttactcat tttagtatac   11880
tgcaatattg aatcaatttc aatatattgt attaacttcc accagatata ttgttttatt   11940
aaggcatatg ctaaaagact tatgaaaaaa ttaaaatata agtttataac acttaatacc   12000
tacattttag gtaatagtct ttatgcttgt gaacaaatct ataaattatg caatgagtac   12060
aattggaaat tcattttttca atttagagaa ggaactttaa atgagtttaa gaggatttag   12120
atgatataaa taaatttaat ctttagcact gaaatgtgca actatatatg tattttttaga   12180 ttattatgct aaacttatag aagtataaaa aatttctaaa atactttaca ataaatagta   12240
atattattaa taacaatgta catatcgaaa aaaatcaaat aatgttttat aatatttaaa   12300
taatcaattt cacacataag gagttaaaaa tgaaagttac tataaatgat atagctcacg   12360
cagcaaatgt atctaaatca acggtatcca aagttataaa taatcataaa tctatttctg   12420
aaagtacaaa gctcaaagta agaaacatta tgaaagagct taactatatt ccaaataatt   12480
cggcaaggca gctagctcgc cagaatagtt ttaatatagg tcttctagta gatattagca   12540
gaaaggaata ttttcttgat ttcttttttct ataatattat tggtggagtt gaaagtatag   12600
ttggaatcaa taactatgag ttaaccctat caaacataaa ttcactagaa tgcaaagcag   12660
aatttctaaa tcgattgata tatagtaaaa aagtagatgg aatcataata cctacctcaa   12720
tagtcaattc ggaaattatt agtaagctca acggtttaaa cttttccttat gtccttattg   12780 gtcagccaaa ggaatttaag aatagtacca gctgggttga tgttaataat actgtaggag   12840
gagaactggc cacatgtcat ttaatagaac aaggttataa aaatatagcc tttattggtg   12900
gcaaatcaaa tgaaataata tctttcaatc ggcttcttgg ttataaaaac atactttcta   12960
aattaaattt tactaaaaat aatttataca taaaagaagg caactcagac aaggaaagtg   13020
gttatgaact tacacttcaa ttattatcag attttcctga aatagatgcc atactatgca   13080
taaataatta tgttgcattt ggtgtactta agcacttaa agaaaagggc ttaaatagcc   13140
ccacagatat tggaattgtg acttttgaca atgaaccatt ttctgcttac accactccat   13200
ccttaacttg tctagatgta gatacattta aacttggtga agtggcagct gaaatttaa   13260 tgaaaaaaat tcaaaatcca aattctcaga atgaaataac cctaatatca cctaaattac   13320
ttatacgtga atctagccta ttgaaaaaac catgaac                           13357
```

CYCLODEXTRIN GLUCANOTRANSFERASE

INCORPORATION BY REFERENCE TO ANY PRIORITY APPLICATIONS

The entire contents of each of the applications listed in the accompanying Application Data Sheet is incorporated by reference herein.

REFERENCE TO SEQUENCE LISTING

A Sequence Listing submitted as in ASCII text file via EFS-Web is hereby incorporated by reference in accordance with 35 U.S.C. §1.52(e). The name of the ASCII text file for the Sequence Listing is 23415553.TXT, the date of creation of the ASCII text file is May 26, 2016, and the size of the ASCII text file is 99 KB.

The present invention relates to a novel cyclodextrin glucanotransferase (CGTase) enzyme which is obtainable from *Clostridium saccharoperbutylacetonicum* N1-4, N1-4 (HMT) or N1-504. The invention further relates to nucleic acids encoding the enzyme, vectors and host cells, and uses of the CGTase.

Cyclodextrins are cyclic glucose oligosaccharides which are generally composed of α-(1,4) linked glucopyranose subunits. Common cyclodextrins include α-cyclodextrin (6-membered sugar ring), β-cyclodextrin (7-membered sugar ring) and γ-cyclodextrin (8-membered sugar ring). Cyclodextrins have many uses in industry, including in separation and extraction processes, as drug-delivery agents and as stabilisers in the food industry. Cyclodextrins have also been used as intermediates in the production of ethanol (e.g. WO 89/03421).

Cyclodextrins are generally produced by the enzymatic conversion of starch using enzymes such as cyclodextrin glucanotransferases. Cyclodextrin glucanotransferases (CGTases) are also known as cyclodextrin glycosyl transferases and cyclodextrin glucosyltransferases. These enzymes are generally only found in bacteria, particularly bacteria of the genus *Bacillus* (e.g. *B. circulans, B. macerans* and *B. stearothermophilus*). It should be noted that wherein *Clostridium thermohydrosulfuricus* was previously classified as a Clostridial species, it has now been reclassified as *Thermoanaerobacter thermohydrosulfuricus* (Collins, M. D. et al. (1994). The phylogeny of the genus *Clostridium*: proposal of five new genera and eleven new species combinations. Int. J. Syst. Bacteriol., 44(4), 812-26). The genus *Thermoanaerobacter* has now clearly established by sequence analysis and shown that it forms a separate and distinct genus from *Clostridium sensu stricto* (Cluster I) (Stackebrandt et al. (1999) Phylogenetic basis for a taxonomic dissection of the genus *Clostridium*. FEMS Immunol. Med. Microbiol., 24(3), 253-8).

Whilst CGTases are generally capable of catalysing more than one reaction, the most important activity is the production of cyclic dextrins from substrates such as starch, amylose and other polysaccharides. In this process, the polysaccharide chain is cleaved and the ends are joined by the CGTase in order to produce a cyclic dextrin, i.e. a cyclodextrin. The size of the cyclodextrin (i.e. the number of sugar residues it incorporates) is dependent on the distance apart of the ends.

There remains a need, however, for novel CGTases, particularly those that are capable of producing novel cyclodextrins.

In one embodiment, therefore, the invention provides a polypeptide, wherein the amino acid sequence of the polypeptide:
  (a) comprises the amino acid sequence set forth in SEQ ID NO: 1 or 3;
  (b) comprises an amino acid sequence which has at least 70% sequence identity with SEQ ID NO: 1 or 3;
  (c) is encoded by the nucleotide sequence set forth in SEQ ID NO: 2 or 4; or
  (d) is encoded by a nucleotide sequence which has at least 70% sequence identity with the nucleotide sequence set forth in SEQ ID NO: 2 or 4.

The invention also provides a composition comprising the polypeptide of the invention.

The invention further provides a nucleic acid molecule comprising:
  (a) the nucleotide sequence set forth in SEQ ID NO: 2 or 4;
  (b) a nucleotide sequence which has at least 70% sequence identity with the nucleotide sequence set forth in SEQ ID NO: 2 or 4; or
  (c) the complement of (a) or (b), preferably operably associated with one or more regulatory elements.

The invention also provides a vector comprising a nucleic acid molecule of the invention. Also provided is a host cell comprising a vector of the invention.

The invention further provides a method of hydrolysing a polysaccharide, comprising contacting the polysaccharide with a polypeptide of the invention.

Also provided is a process for producing a cyclodextrin, the process comprising the steps:
  (i) contacting a polypeptide of the invention with a polysaccharide substrate in a reaction vessel, and
  (ii) isolating a cyclodextrin from the reaction vessel,
  and optionally purifying and/or concentrating the obtained cyclodextrin.

The invention also provides a cyclodextrin which is obtainable or obtained by a process of the invention.

The polypeptide of the invention may be isolated and/or purified. In particular, the polypeptide of the invention may be in a form which is isolated from one or more of the following: bacteria, polysaccharide (e.g. potato, starch), yeast extract, tryptone, other enzymes.

The polypeptide may be purified, i.e. the polypeptide may be substantially pure. In particular, the polypeptide may be at least 90%, preferably at least 95% and more preferably at least 99% pure. Purity may be assessed using SDS-PAGE or any other appropriate method.

The invention also provides variants or derivatives of the polypeptide of SEQ ID NO: 1 or 3. The proteins of the invention may be altered in various ways including substitutions, deletions, truncations, and/or insertions of one or more (e.g. 2-5, 2-10) amino acids, preferably in a manner which does not substantially alter the biological activity of the polypeptide of the invention. Guidance as to appropriate amino acid changes that do not affect biological activity of the protein of interest may be found in the model of Dayhoff et al. (1978) Atlas of Protein Sequence and Structure (Nat'l. Biomed. Res. Found., Washington, D.C.), herein incorporated by reference. Conservative substitutions, such as exchanging one amino acid with another having similar properties, may be also made.

In particular, substitution of one hydrophobic amino acid such as isoleucine, valine, leucine or methionine for another may be made; or the substitution of one polar amino acid residue for another, such as arginine for lysine, glutamic for aspartic acid, or glutamine for asparagine, may be made.

One or more (e.g. 1-5, 1-10) amino acids in the polypeptides of the invention may be substituted by their corresponding D-amino acids, preferably at the N- and/or C-terminus.

In particular, the invention provides a variant of the polypeptide of SEQ ID NO: 1 or 3, wherein the amino acid sequence of the variant comprises or consists of an amino acid sequence having at least 70%, preferably at least 80%, 85%, 90%, 95% or 99% sequence identity with SEQ ID NO: 1 or 3, preferably using the blastp method of alignment.

The invention particularly relates to polypeptides of SEQ ID NO: 1 or 3 or to variants of the polypeptide of SEQ ID NO: 1 or 3 as defined herein, wherein the amino acid which corresponds to the amino acid at position 223 is a small amino acid, e.g. glycine, alanine, leucine, serine, threonine or valine, preferably glycine. The size of the amino acid residue at position 223 may be involved in determining the size of any cyclodextrin products or ratio of any cyclodextrin products.

The CGTases of the invention are capable of producing one or more cyclodextrins from polysaccharides, e.g. starch.

The CGTases fall within the general EC classification 2.4.1. (hexosyltransferases). In some embodiments, the CGTase of the invention falls within classification EC 2.4.1.248 (cycloisomaltooligosaccharide glucanotransferase). In other embodiments of the invention, the CGTase falls within classification EC 2.4.1.19 (cyclomaltodextrin glucanotransferase).

The invention also provides a composition comprising or consisting essentially of a polypeptide of the invention. The polypeptide may be present in the composition in the absence of one or more of the following: bacteria, polysaccharide (e.g. potato, starch), yeast extract, tryptone.

The polypeptide of the invention may be provided in any suitable form, e.g. in lyophilised form or in a buffer.

As used herein, the term "nucleic acid molecule" refers to a DNA or RNA molecule, which might be single- or double-stranded. Preferably, the nucleic acid molecule is a DNA molecule, most preferably a double-stranded DNA molecule. The nucleic acid molecule is preferably one which contains no introns. The nucleic acid molecule may, for example, be intron-less genomic DNA or cDNA.

The nucleic acid molecule of the invention is preferably isolated or purified. As used herein, the term "isolated nucleic acid" means that the nucleic acid molecule is not contiguous with other genes with which it is normally associated in the natural source of the polypeptide-encoding nucleic acid. For example, an isolated nucleic acid of the invention will not be contiguous with a nucleic acid encoding a maltose binding protein periplasmic precursor; or it will not be contiguous with a nucleic acid encoding a neopullananse/cyclomaltodextrinase.

As used herein, the term "purified nucleic acid" means a nucleic acid molecule which is free or substantially free from other non-contiguous nucleic acids and/or is free or substantially free from one or more of the following: bacteria, polysaccharide (e.g. potato, starch), yeast extract, tryptone.

As used herein, the term "polysaccharide" or "polysaccharide substrate" refers preferably to a glucose-based polysaccharide, e.g. a starch or a starch-based material. Most preferably, the polysaccharide is starch or a starch-based material, e.g. corn, corn starch, corn mash, potato, potato starch, potato mash, potato peeling, potato chips, cassava, cassava starch, cassava chips, sago, sago starch or 'soluble starch'. e.g. as sold by Fisher/Sigma. In some embodiments of the invention, the nucleic acid molecule is a recombinant nucleic acid.

The nucleic acid of the invention is preferably operably associated with one or more regulatory elements, e.g. a promoter and/or a terminator element. As used herein the term "operably associated" or "operably linked" with a promoter means that the polypeptide-encoding region is transcribable from that promoter. The polypeptide-encoding region may, for example, be immediately 3' to the promoter, in which case the promoter will direct the transcription of the coding sequence. Alternatively, the polypeptide-encoding region may be part of an operon in which case the associated or linked promoter will direct the transcription of all of the polypeptide-encoding regions within that operon.

The promoter or promoters are preferably ones which are operable in bacterial cells. More preferably, the promoters are bacterial promoters. Suitable promoters include inducible promoters, such as those that are inducible with specific sugars or sugar analogues, e.g. arabinose (e.g. lac, ara), those inducible with antibiotics (e.g. tetracycline, tet), those inducible with IPTG (e.g. trp, tac, Pspac), those inducible with heat (e.g. hsp70), those inducible with anaerobic induction (e.g. nisA, pfl, trc, IPL, IPR, T7), P11, ldh, sec (secDF), SV40 promoter, those inducible with xylose (e.g. Pxyl promoter), those inducible with osmotic shock, cell density (quorum sensing), anaerobicity, antibiotics, or growth phase. In some embodiments, the promoter is a constitutive promoter, e.g. the promoters for the thiolase gene (thl) or the permease operon (hfuC). In other embodiments, the promoter is one from Clostridia, e.g. a promoter from the pta/ptb genes. In yet other embodiments, the promoter is one from a butanol and/or butyrate biosynthetic pathway gene.

In other embodiments, the promoter is an early onset promoter, i.e. a promoter from a gene which is upregulated during early exponential phase and reduced during transition phase and stationary phase. Examples of such promoters include promoters from glcK, hydA genes, or vitamin B12 synthesis, pta, ptb promoters.

In other embodiments, the promoter is a promoter from a gene which is normally active in the exponential phase of solventogenic bacteria. Examples include promoters from genes that are expressed constitutively throughout exponential phase, e.g. from glycolysis genes and those in the pathway to produce butyryl-CoA (pfk, gap, pgk, bcd).

Other examples of suitable promoters include the P2 (pta-ack, CAC1742, promoter), P6 (luxS, CAC2942, promoter) and P7 (CAC2941) promoters (Alsaker and Papoutsakis, 2005, J. Bacteriol. 187:7103-7118).

The P2 promoter is the promoter region from the operon encoding the phosphotransferase and the acetate kinase involved in acetate production from acetyl-CoA. The P6 promoter is the promoter region from a single chromosomal open reading frame encoding a LuxS homolog (CAC 2942), predicted to be involved in quorum sensing. The P7 promoter is the promoter region from a chromosomal operon (CAC 2938-2941) encoded downstream and in the reverse orientation to CAC 2942 and putatively involved in quorum sensing. The operon encodes a hydrolase (CAC 2941), a histidine kinase (CAC 2940), a response regulator (CAC 2939) and a hypothetical protein (CAC 2938).

In a further embodiment, the invention provides a variant of the nucleic acid molecule of SEQ ID NO: 2 or 4, wherein the nucleotide sequence of the variant comprises or consists of an nucleotide sequence having at least 70%, preferably at least 80%, 85%, 90%, 95% or 99% sequence identity with SEQ ID NO: 2 or 4, preferably using the BLASTN method of alignment.

Percentage amino acid sequence identities and nucleotide sequence identities may be obtained using the BLAST methods of alignment (Altschul et al. (1997), "Gapped BLAST and PSI-BLAST: a new generation of protein database search programs", Nucleic Acids Res. 25:3389-3402. Preferably the standard or default alignment parameters are used.

Standard protein-protein BLAST (blastp) may be used for finding similar sequences in protein databases. Like other BLAST programs, blastp is designed to find local regions of similarity. When sequence similarity spans the whole sequence, blastp will also report a global alignment, which is the preferred result for protein identification purposes. Preferably the standard or default alignment parameters are used. In some instances, the "low complexity filter" may be taken off.

BLAST protein searches may also be performed with the BLASTX program, score=50, wordlength=3. To obtain gapped alignments for comparison purposes, Gapped BLAST (in BLAST 2.0) can be utilized as described in Altschul et al. (1997) Nucleic Acids Res. 25: 3389. Alternatively, PSI-BLAST (in BLAST 2.0) can be used to perform an iterated search that detects distant relationships between molecules. (See Altschul et al. (1997) supra). When utilizing BLAST, Gapped BLAST, PSI-BLAST, the default parameters of the respective programs may be used.

With regard to nucleotide sequence comparisons, MEGA-BLAST, discontiguous-megablast, and blastn may be used to accomplish this goal. Preferably the standard or default alignment parameters are used. MEGABLAST is specifically designed to efficiently find long alignments between very similar sequences. Discontiguous MEGABLAST may be used to find nucleotide sequences which are similar, but not identical, to the nucleic acids of the invention. The BLAST nucleotide algorithm finds similar sequences by breaking the query into short subsequences called words. The program identifies the exact matches to the query words first (word hits). The BLAST program then extends these word hits in multiple steps to generate the final gapped alignments. In some embodiments, the BLAST nucleotide searches can be performed with the BLASTN program, score=100, wordlength=12.

One of the important parameters governing the sensitivity of BLAST searches is the word size. The most important reason that blastn is more sensitive than MEGABLAST is that it uses a shorter default word size (11). Because of this, blastn is better than MEGABLAST at finding alignments to related nucleotide sequences from other organisms. The word size is adjustable in blastn and can be reduced from the default value to a minimum of 7 to increase search sensitivity.

A more sensitive search can be achieved by using the newly-introduced discontiguous megablast page that is available through the website of the National Center for Biotechnology Information. This page uses an algorithm which is similar to that reported by Ma et al. (Bioinformatics. 2002 March; 18(3): 440-5). Rather than requiring exact word matches as seeds for alignment extension, discontiguous megablast uses non-contiguous word within a longer window of template. In coding mode, the third base wobbling is taken into consideration by focusing on finding matches at the first and second codon positions while ignoring the mismatches in the third position. Searching in discontiguous MEGABLAST using the same word size is more sensitive and efficient than standard blastn using the same word size. Parameters unique for discontiguous megablast are: word size: 11 or 12; template: 16, 18, or 21; template type: coding (0), non-coding (1), or both (2).

In yet other embodiments, the nucleic acid of the invention is present in an operon, preferably with one or more genes which are involved in starch metabolism. Preferably, the nucleic acid of the invention is in an operon, wherein the nucleic acid of the invention is contiguous with one or more nucleic acid molecules which encode one or more of the following: a maltose binding protein periplasmic precursor, a neopullanase/cyclomaltodextrinase, one or more maltose/maltodextrin ABC transporter permease proteins, an alpha amylase catalytic domain protein and a glycogen debranching protein.

As used herein, the term "operon" refers to a segment of a nucleic acid molecule which comprises a linear sequence of two, three, four or more polypeptide-encoding regions which are all in the same 5'-3' orientation and which are transcribable as a single (polycistronic) unit from an associated promoter. The promoter will in general be at the 5' end of the operon.

In this case, transcription will be initiated from the first promoter and a single polycistronic mRNA transcript will be produced from the said two, three, four or more of the polypeptide-encoding regions.

The remaining polypeptide-encoding regions of the nucleic acid molecule may independently be operably linked together with a second promoter in a second operon, wherein the second operon is transcribable from the second promoter; or they may each be operably linked to and transcribable from further promoters.

Preferably, the operon has the sequence as given in SEQ ID NO: 5, or a variant thereof having at least 70%, preferably at least 80%, 90%, 95% or 99% sequence identity with SEQ ID NO: 5 using the BLASTN method of alignment.

In some embodiments, the operon encodes the following polypeptides in the order 5'-3' (and each coding sequence being in the 5'-3' direction): a maltose binding protein periplasmic precursor, an isocyclomaltooligosaccharide glucanotransferase (of the invention), a neopullanase/cyclomaltodextrinase, two maltose/maltodextrin ABC transporter permease proteins, an alpha amylase catalytic domain protein and a glycogen debranching protein.

The nucleic acid molecule of the invention or operon will preferably be in the form of a vector, particularly an expression vector, or a plasmid. The vector or plasmid may comprise one or more selectable markers and/or other genetic elements. Preferably, the vector or plasmid is less than 100 Kb, more preferably less than 90, 80, 70, 60, 50, 40, 30 or 20 Kb. Preferably, the vector or plasmid additionally comprises one or more antibiotic resistance genes. Examples of such genes include genes conferring resistance to ampicillin, erythromycin, neomycin/kanamycin, tetracycline, chloramphenicol, spectinomycin, bleomycin and puromycin. In some embodiments, the vector or plasmid also comprises one or more genes conferring tolerance to one or more heavy metals, e.g. mercury. Other selectable markers include auxotrophy genes, e.g. genes for essential amino acids.

The vector or plasmid may also comprise an origin of replication, for example a Gram positive and/or a Gram negative origin of replication. The vector or plasmid may also comprise one or more insertion sequences, e.g. Tn10, Tn5, Tn1545, Tn916 and/or ISCb.

The nucleic acid molecule of the invention or operon or the plasmid or vector, may be introduced into a host cell, e.g. a micro-organism, preferably a bacterial cell.

The bacterial cell may, for example, be a Gram-positive or Gram-negative bacterium. In some embodiments, the micro-organism is a spore-forming bacterium. In other embodiments, the micro-organism is a saccharolytic bacterium.

The bacterium may be an aerobic or an anaerobic bacteria. Preferably it is an anaerobic bacteria. The bacteria may be a thermophilic bacterium. In yet other embodiments, the bacterium is a biphasic bacterium. As used herein, the term "biphasic" refers to a bacterium which has an acidogenic growth phase and a solventogenic growth phase. The term "acidogenic growth phase" refers to the ability of the bacterium to convert a substrate into R—COOH, for example, into acetate and/or butyrate. In this context, wherein R is an aliphatic C1-05, preferably C1-3, alkyl or alkenyl group. The term "solventogenic growth phase" refers to the ability of the bacterium to convert the RCOOH into a solvent, preferably into one or more of acetone, ethanol and/or butanol.

In other embodiments, the bacterium is a solvent-producing bacterium. As used herein, the term "solvent-producing" means that the bacterium is one which is capable of producing a solvent, preferably a solvent such as acetone, ethanol, propanol and/or butanol. In certain particularly preferred embodiments, the bacterium is capable of producing ethanol, acetone and butanol. Preferably, the bacteria is a butanol-producing bacteria or a butanol-tolerant bacterium.

In some preferred embodiments, the bacterium is of the genus *Clostridium*. Preferred *Clostridium* species include *C. acetobutylicum, C. aurantibutyricum, C. beijerinckii, C. thermocellum, C. thermobutyricum, C. pasteurianum, C. kluyveri, C. saccharobutylicum, C. thermosaccharolyticum, C. saccharolyticum, C. tyrobutyricum, C. butyricum, C. puniceum, C. diolis* and *C. roseum*.

In some embodiments, the bacteria is a Cluster I Clostridia. Preferred examples of Cluster I *Clostridia* include *C. acetobutylicum, C. arbusti, C. argentinense, C. beijerinckii, C. butyricum, C. cellulovorans, C. diolis, C. kluyveri, C. novyi, C. pasteurianum, C. puniceum, C. roseum, C. saccharobutylicum, C. saccharoperbutylacetonicum* and *C. tyrobutyricum*.

In some embodiments of the invention, the host cell is not *C. saccharoperbutylacetonicum* N1-4. In other embodiments of the invention, the host cell is not *C. saccharoperbutylacetonicum* N1-4(HMT). In yet other embodiments of the invention, the host cell is not *C. saccharoperbutylacetonicum* N1-504.

In other preferred embodiments, the bacterium is of the genus *Bacillus* or *Geobacillus*.

The invention further provides a process for making a recombinant bacterial host cell, comprising introducing a nucleic acid molecule of the invention, or an operon or a vector or plasmid of the invention, into a bacterial host. Methods of introducing nucleic acid molecules, operons, plasmids and vectors into bacterial hosts are well known in the art. These include transformation, transfection and electroporation techniques.

The invention also provides a recombinant bacterial host comprising a nucleic acid molecule of the invention, or an operon or a vector or plasmid of the invention.

The nucleic acid molecule or operon may be present in the cytoplasm of the host, e.g. as a plasmid or a vector, or it may be integrated in the host genome.

The invention therefore provides a bacterial cell comprising a nucleic acid molecule, an operon, a vector or plasmid of the invention, wherein the nucleic acid molecule, operon, vector or plasmid is present in the cytoplasm of the cell.

The invention also provides a bacterial cell comprising a nucleic acid molecule of the invention or an operon or vector or plasmid of the invention, wherein the nucleic acid molecule, operon, vector or plasmid is stably integrated into the genome of the cell.

In a further embodiment, the invention provides a method of hydrolysing a polysaccharide, comprising contacting the polysaccharide with a polypeptide of the invention. Preferably, the polypeptide is in isolated or purified form.

The invention also provides the use of a polypeptide of the invention in the hydrolysis of a polysaccharide.

The invention also provides a method of hydrolysing a polysaccharide, comprising contacting the polysaccharide with a host cell of the invention, preferably a recombinant bacterial host cell of the invention.

The invention particularly provides a method of hydrolysing a polysaccharide, comprising contacting the polysaccharide with a host cell of the invention which has been stably transformed with a nucleic acid or operon or vector or plasmid of the invention, such that the host cell expresses a CGTase and optionally one or more other polypeptides which are involved in starch metabolism.

As used herein, the term "polypeptides which are involved in starch metabolism" includes maltose binding protein periplasmic precursors, isocyclomaltooligosaccharide glucanotransferases, neopullanase/cyclomaltodextrinases, maltose/maltodextrin ABC transporter permease proteins, alpha amylase catalytic domain proteins and glycogen debranching proteins.

Preferably, the host cell is also capable of converting the hydrolysed polysaccharide to an acid such as R—COOH, for example into acetate and/or butyrate. Optionally, the host cell is also capable of converting the RCOOH into a solvent, preferably into one or more of acetone, ethanol and/or butanol.

The invention also provides a method of producing a solvent comprising the steps:
  (i) incubating a host cell of the invention, preferably a recombinant bacterial host cell of the invention, with a polysaccharide substrate;
wherein the host cell is also capable of converting hydrolysed polysaccharide to an acid such as R—COOH, for example into acetate and/or butyrate. Optionally, the host cell is also capable of converting the RCOOH into a solvent, preferably into one or more of acetone, ethanol and/or butanol.

Preferably, step (i) is carried out under conditions wherein the host cell expresses the CGTase and wherein the CGTase hydrolyses some or all of the polysaccharide substrate.

The host cell may be one which is naturally capable of converting the hydrolysed polysaccharide to an acid such as R—COOH and/or which is naturally capable of converting the RCOOH into a solvent. Alternatively, the host cell is one which has been transformed with one or more nucleic acid molecules encoding polypeptides which are capable of converting the hydrolysed polysaccharide to an acid such as R—COOH and/or which are capable of converting the RCOOH into a solvent.

The invention also provides a process for producing a cyclodextrin, the process comprising the steps:
  (i) contacting a polypeptide of the invention with a polysaccharide substrate in a reaction vessel, and (ii) isolating a cyclodextrin from the reaction vessel, and optionally purifying and/or concentrating the obtained cyclodextrin.

Preferably, the polysaccharide substrate a glucose-based polysaccharide. More preferably, the polysaccharide substrate is starch or a starch-based material, e.g. corn mash, potato mash, potato peeling, The invention also provides a cyclodextrin which is obtainable or obtained by a process of the invention.

The invention further provides a cyclodextrin with an elution profile as shown in FIG. 7 herein. Preferably, the cyclodextrin is resistant to hydrolysis by amylases.

BRIEF DESCRIPTION OF THE FIGURES

FIG. 4. The protein sequence of the *C. saccharoperbutylacetonicum* CGTase enzyme was aligned with various previously reported CGTases. It does not cluster with the well characterised α-, β-, γ-CGTases, instead being more closely related to enzymes that cyclise starch using various other mechanisms.

FIG. 5. Amino acid alignment of highly conserved residues required for cyclisation. α-, β-, γ-CGTases that use α1-4 linkages have a Tyr or Phe at this position (highlighted with arrow). The CGTases that use a different cyclisation mechanism, all have small residues, e.g. Gly. *C. saccharoperbutylacetonicum* (lines 31 and 32) sequences both have a Gly at this position. The sequences identified in FIG. 5 as numbers 1-41 correspond to SEQ ID NOs: 6-46.

FIG. 7. Crude supernatant extracts were added to 10 g/L starch solution and incubated overnight to compare starch degradation products by HPLC. *C. acetobutylicum* has a well studied α-amylase, glucoamylase, method of hydrolysing starch to glucose. *C. saccharoperbutylacetonicum*, on the other hand, does not convert starch to glucose, instead processing it only as far as the cyclic compound.

Figure 8A:
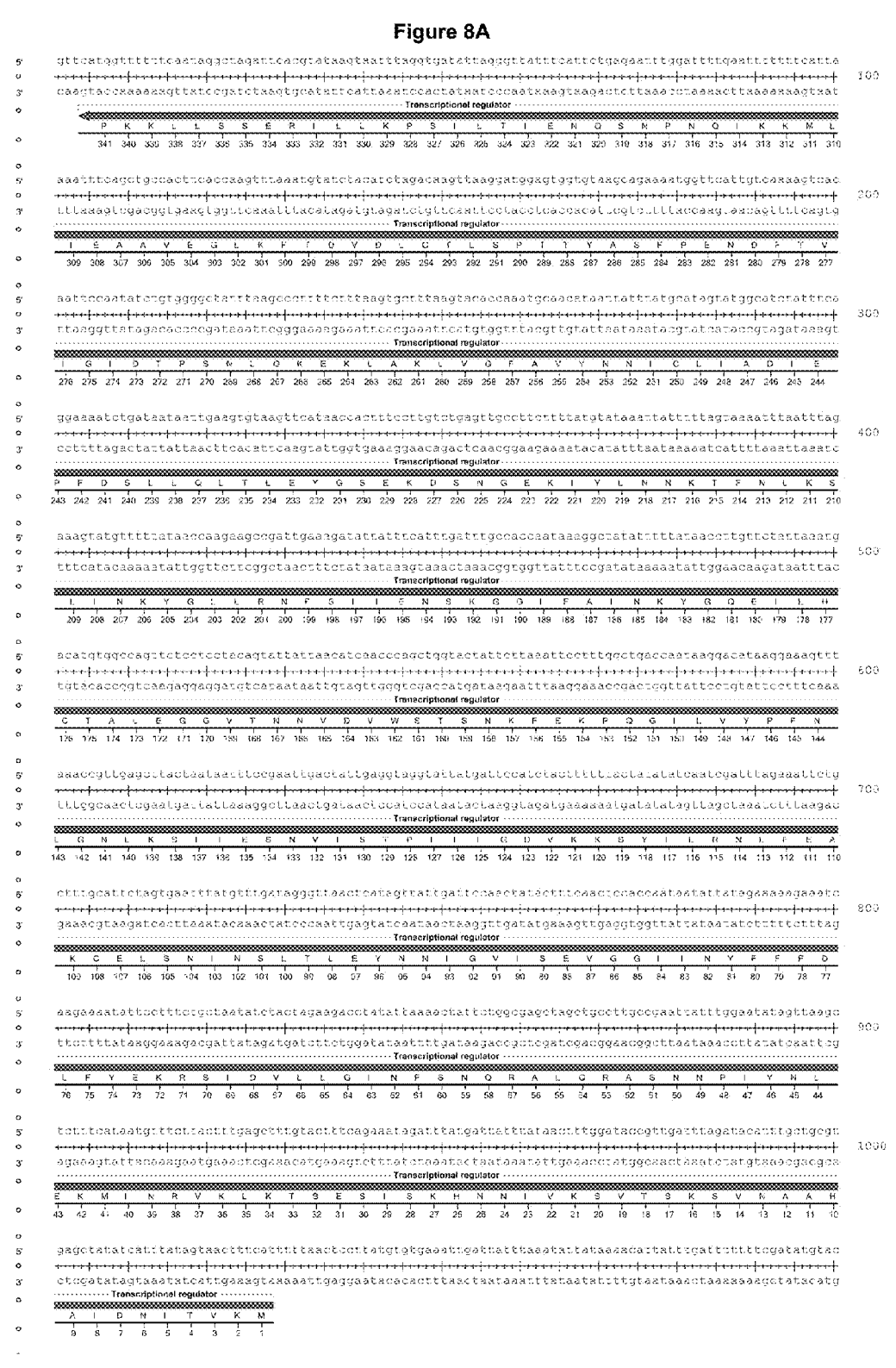
Figure 8B:
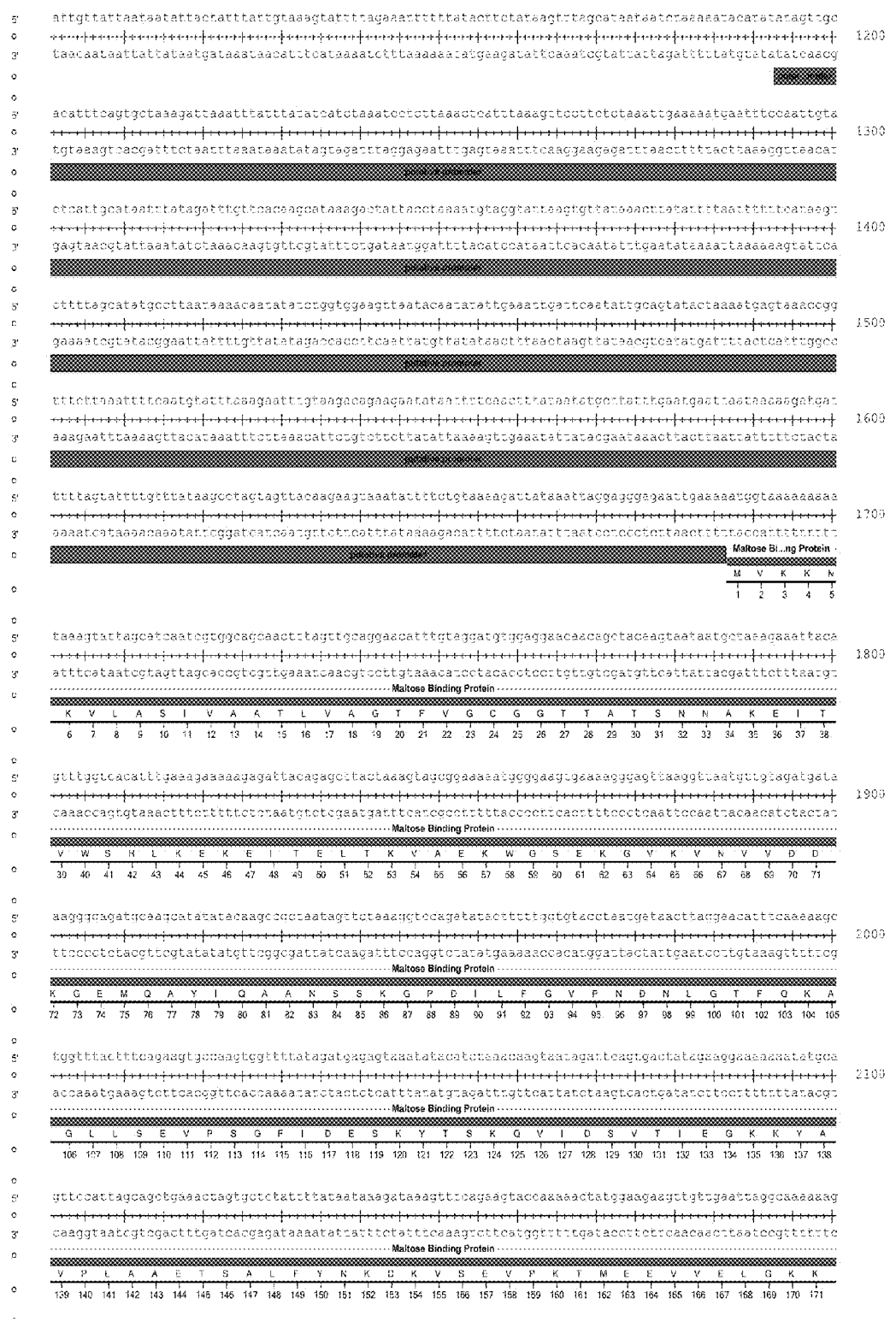
Figure 8C:
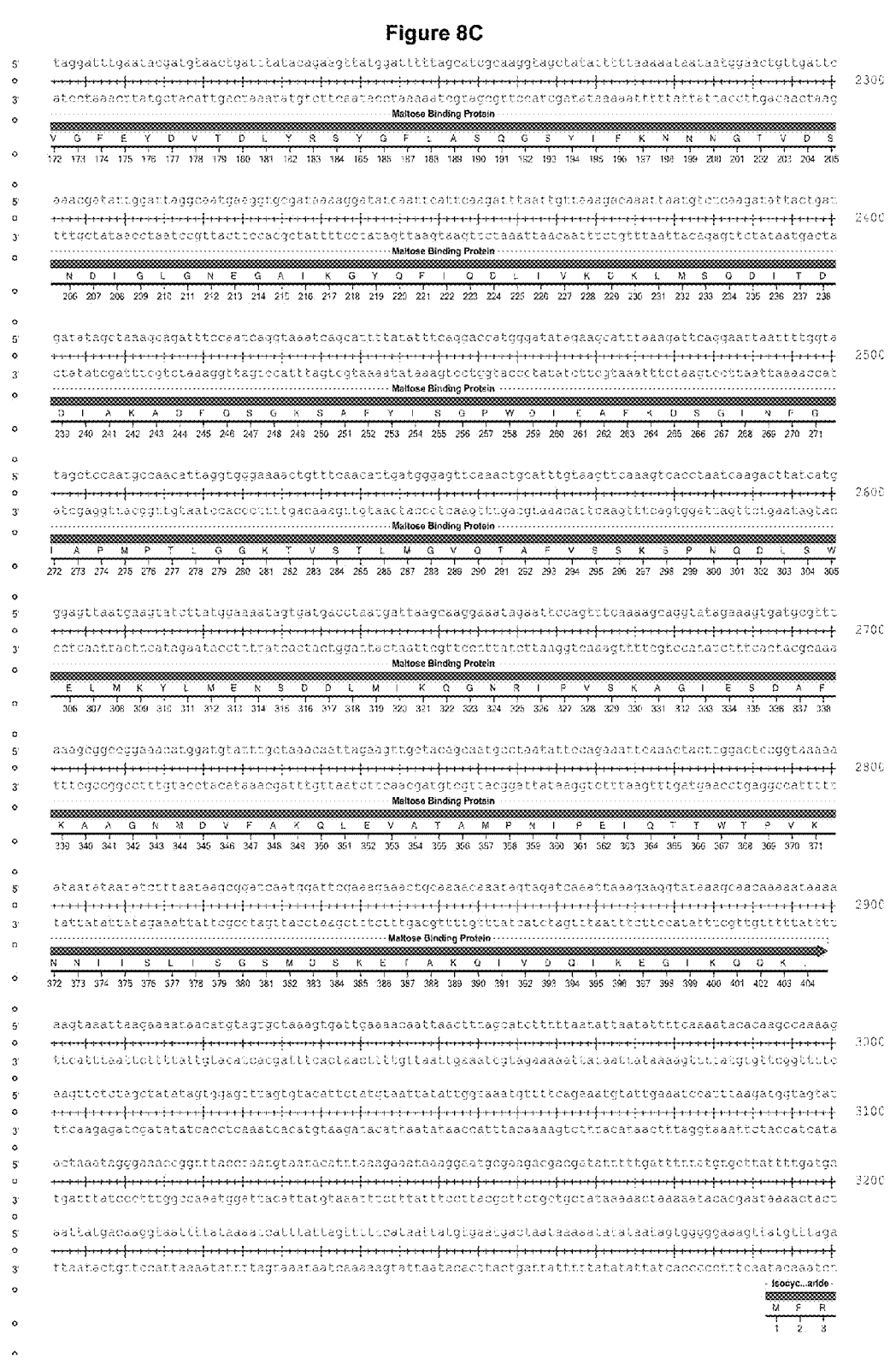
Figure 8D:
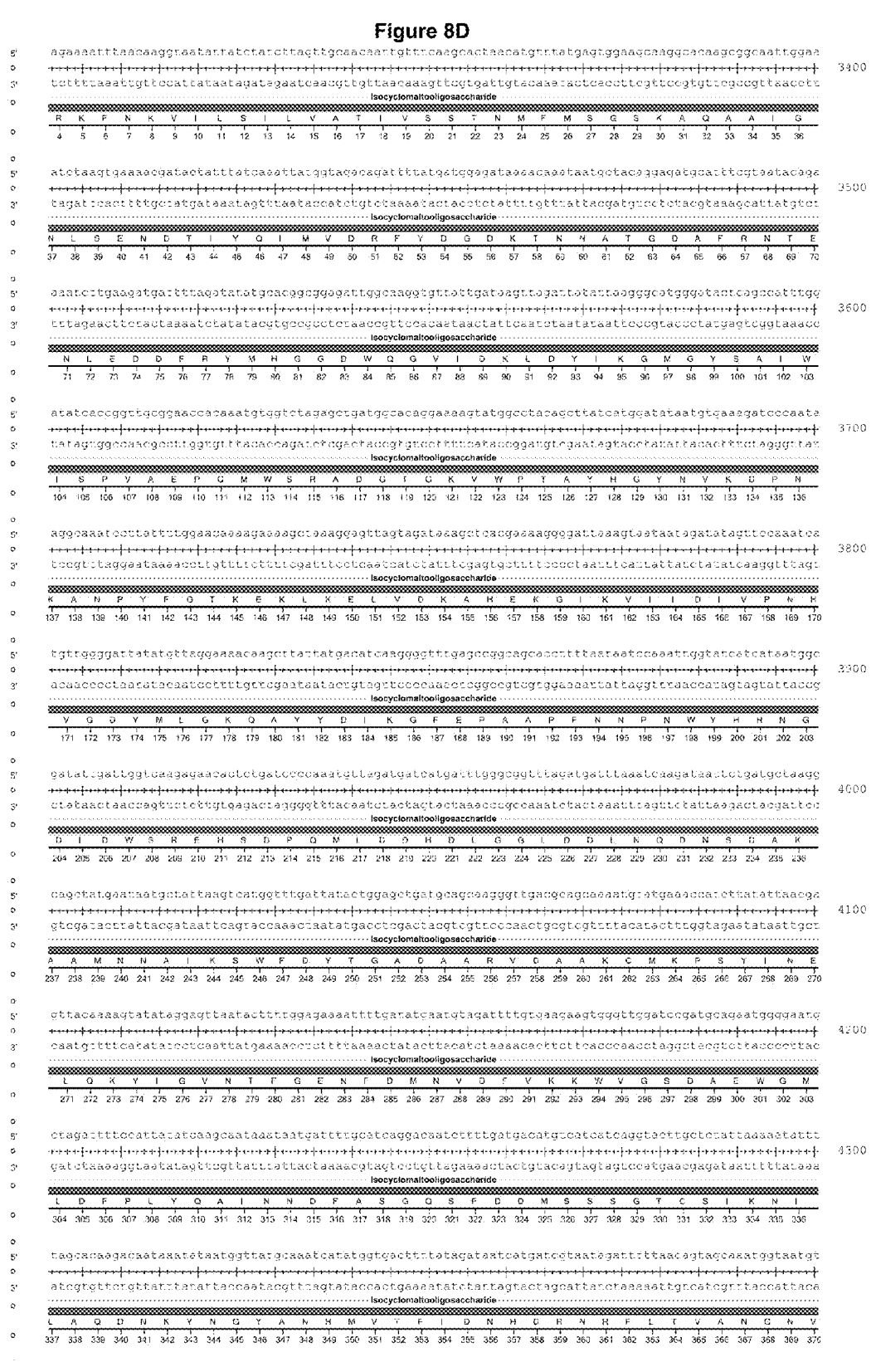
Figure 8E:
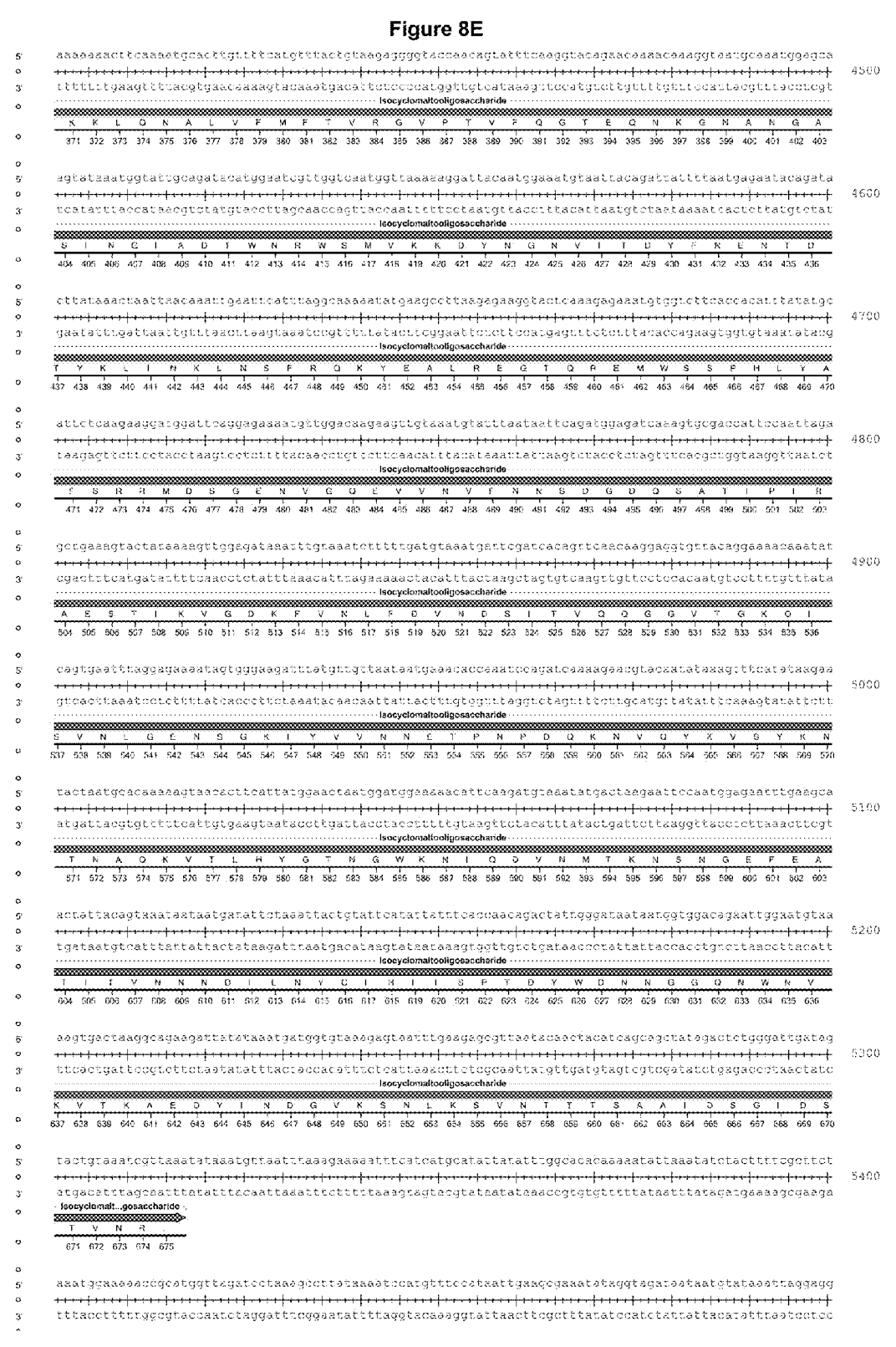
Figure 8F:
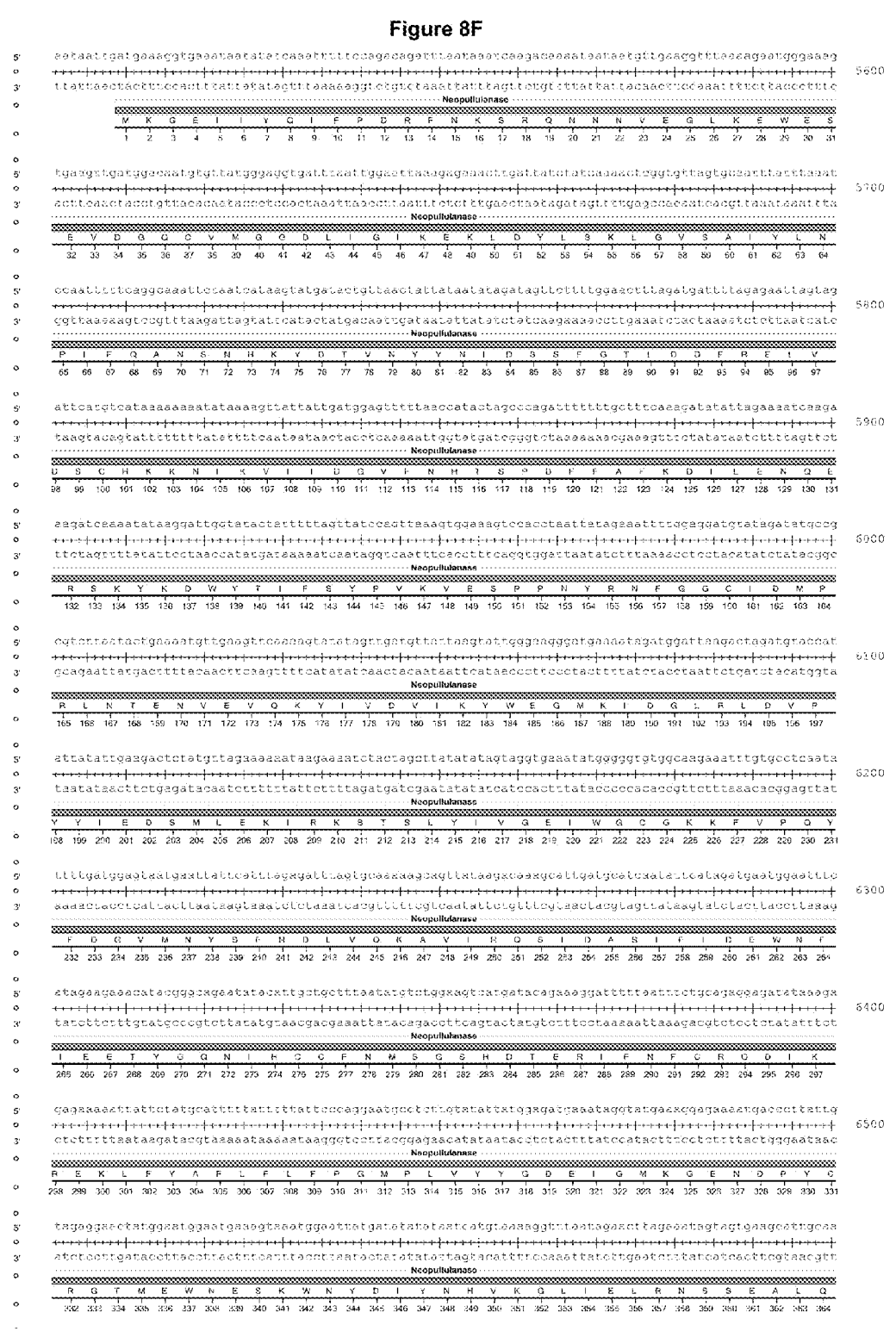
Figure 8G:
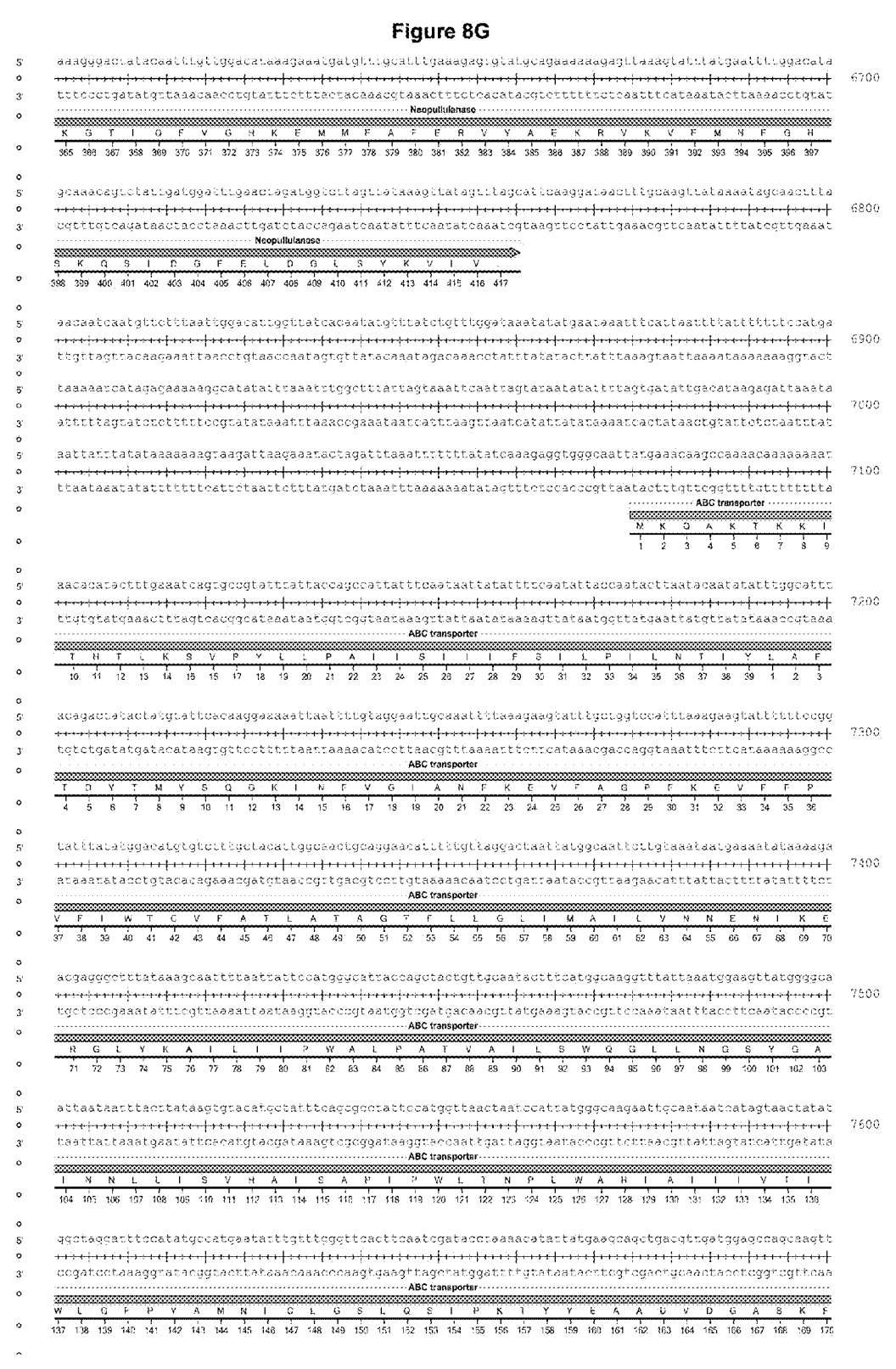
Figure 8H:
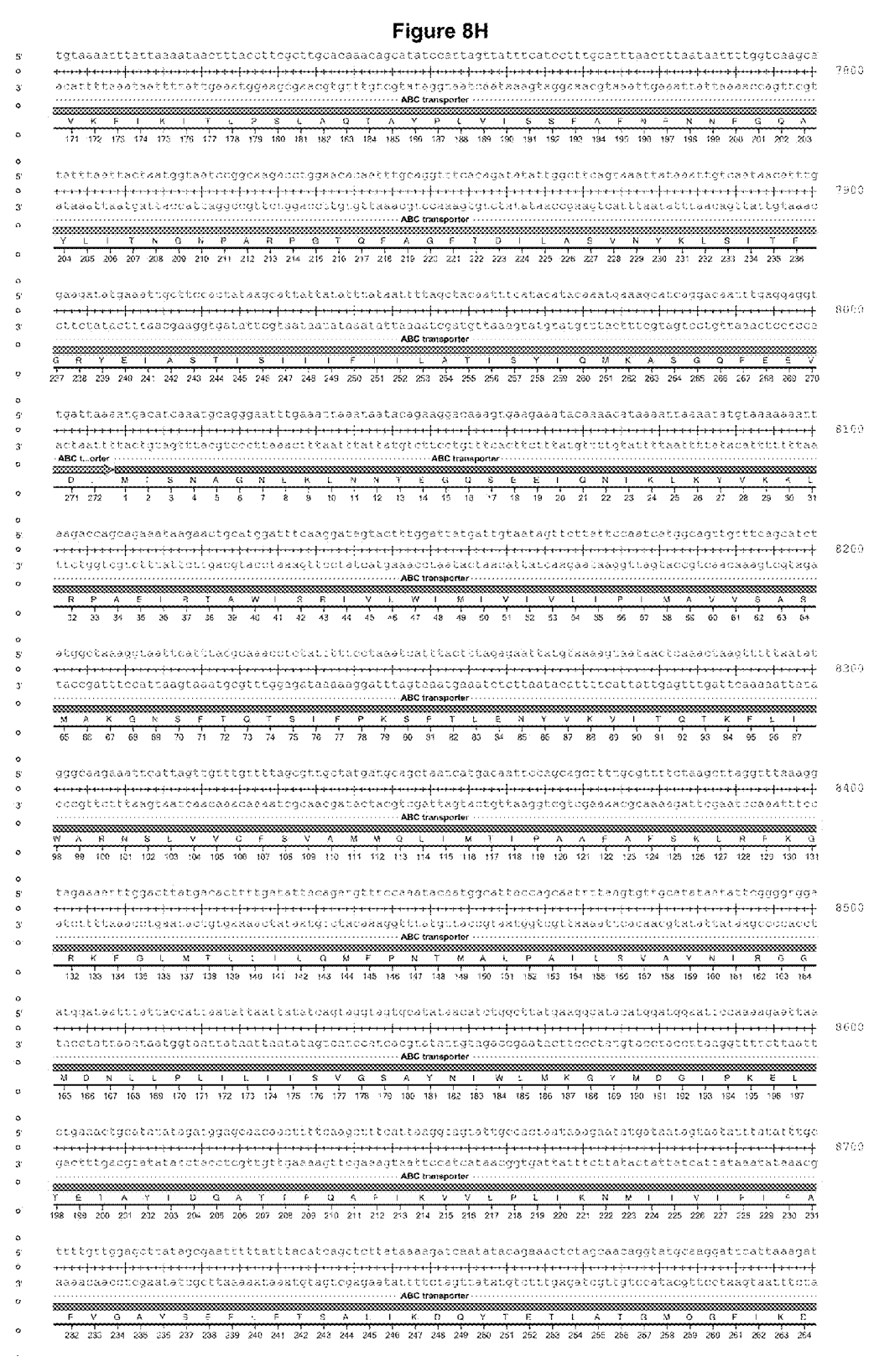
Figure 8I:
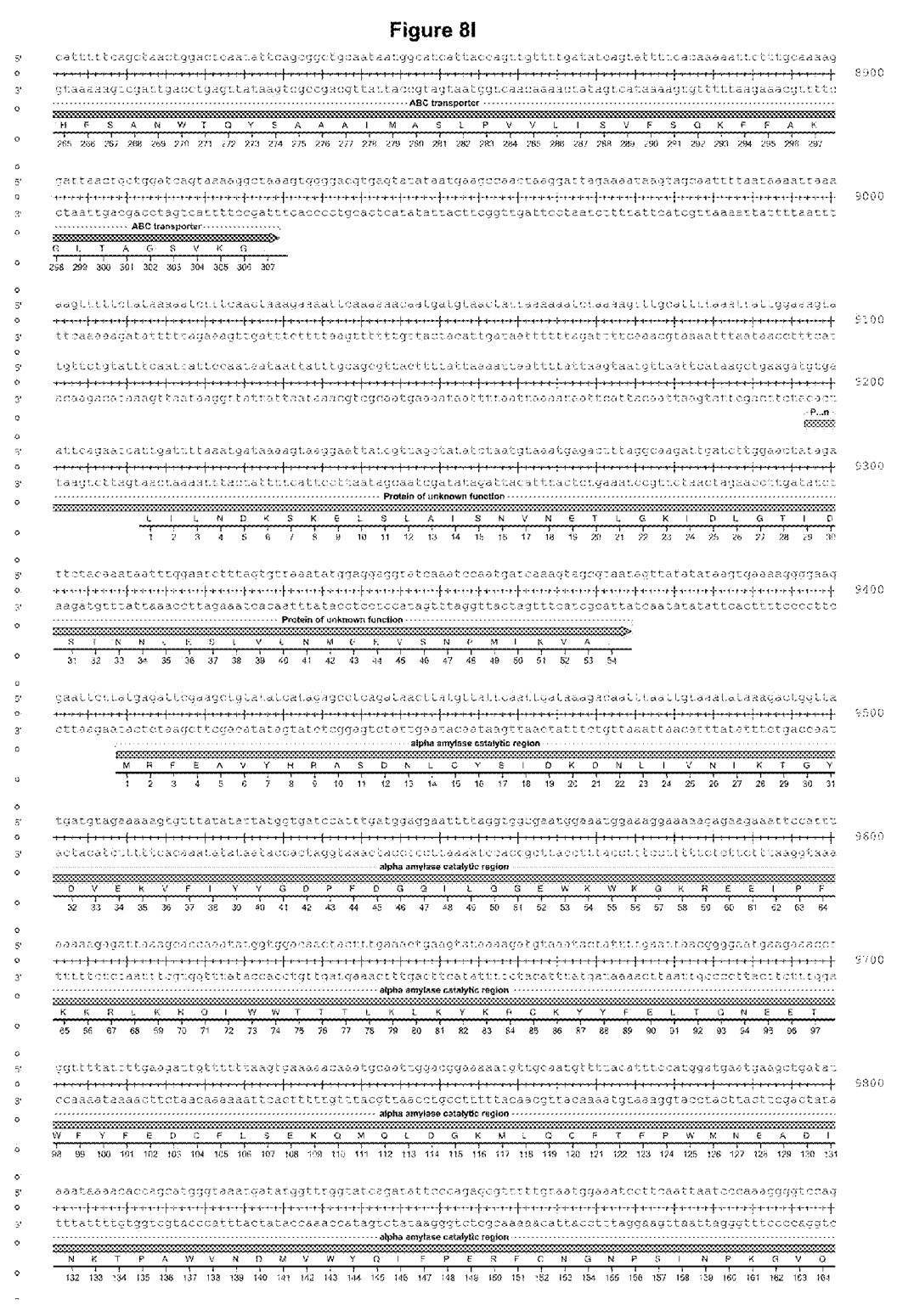
Figure 8J:
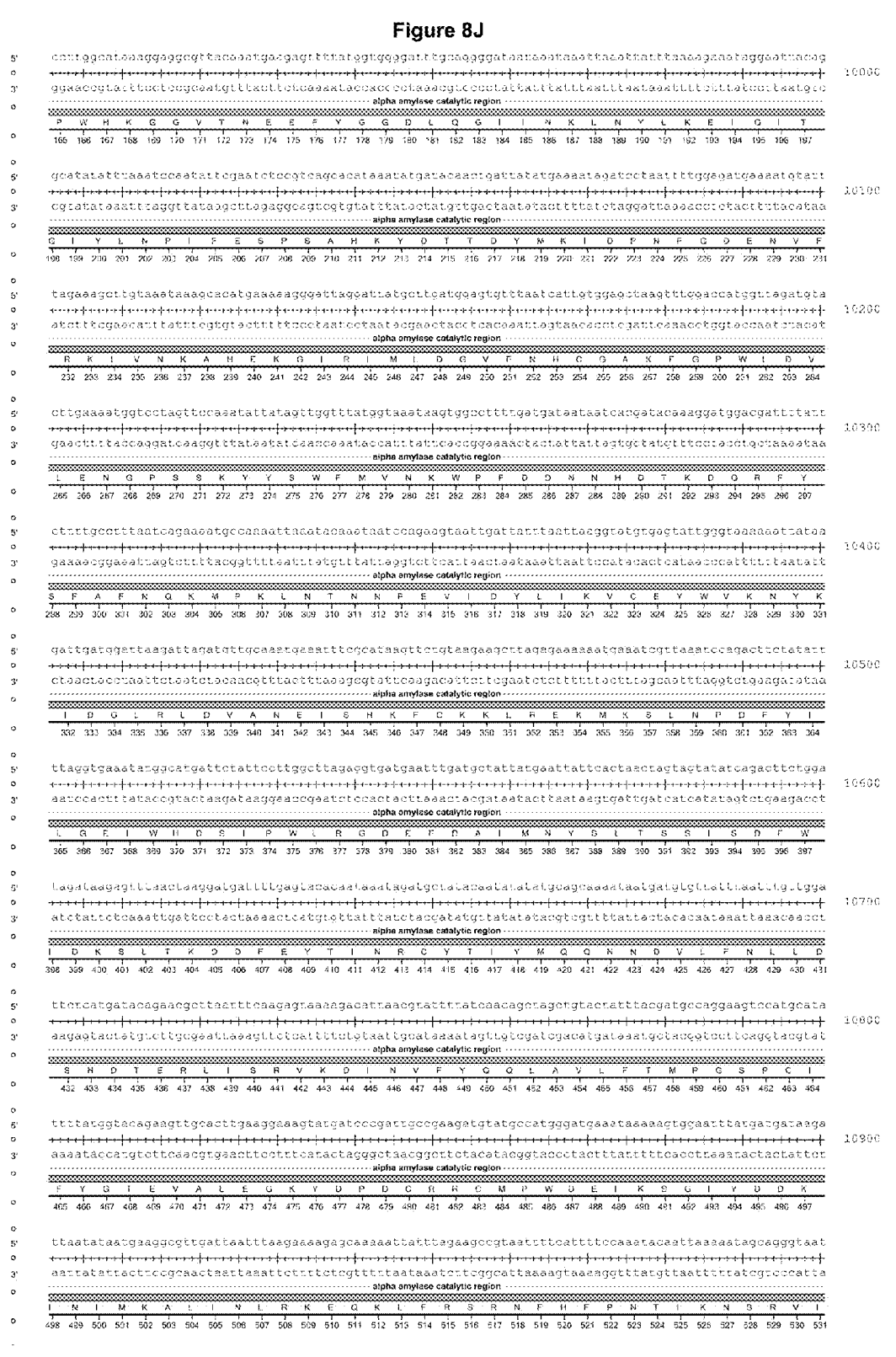
Figure 8K:
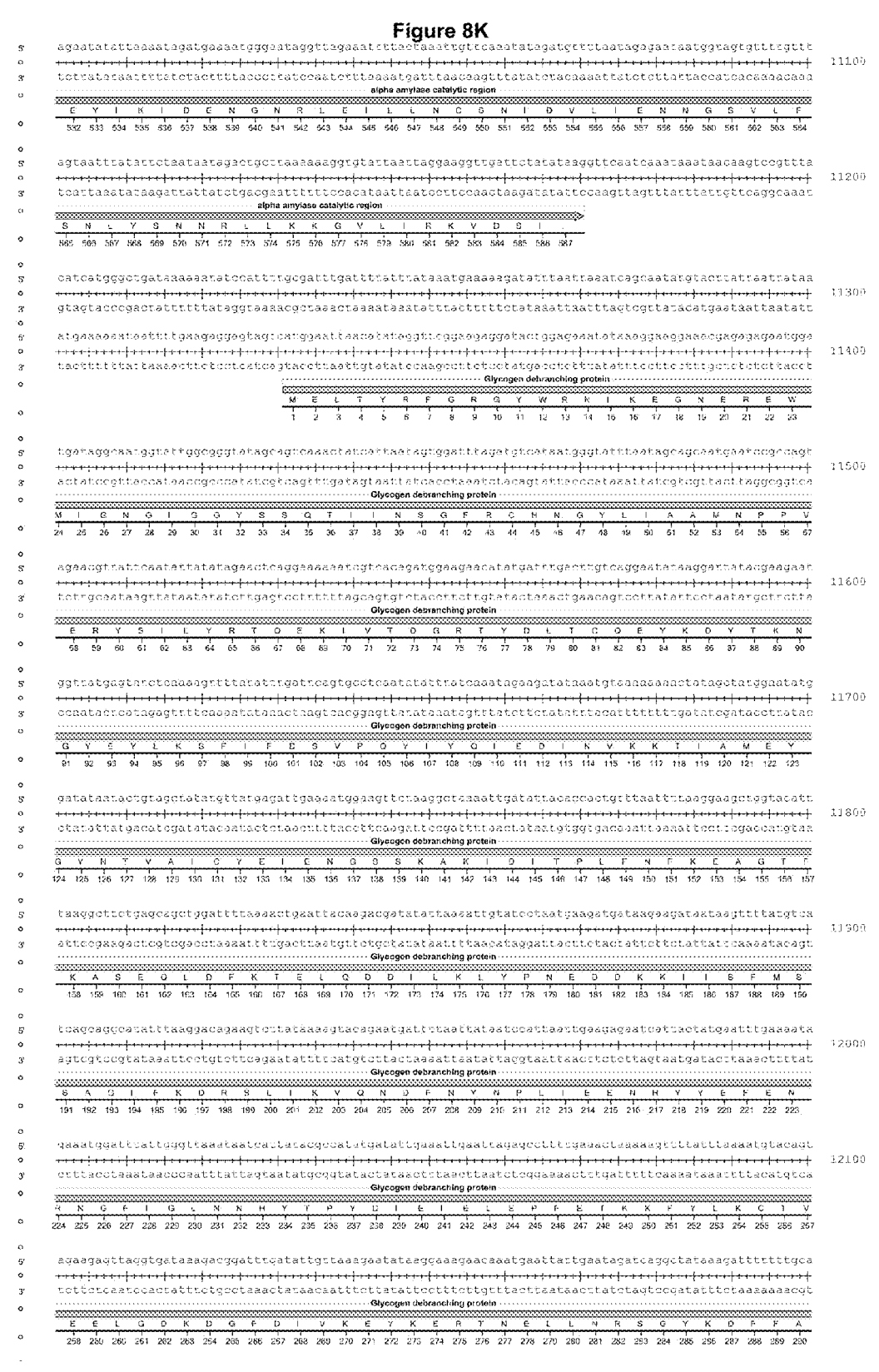
Figure 8L:
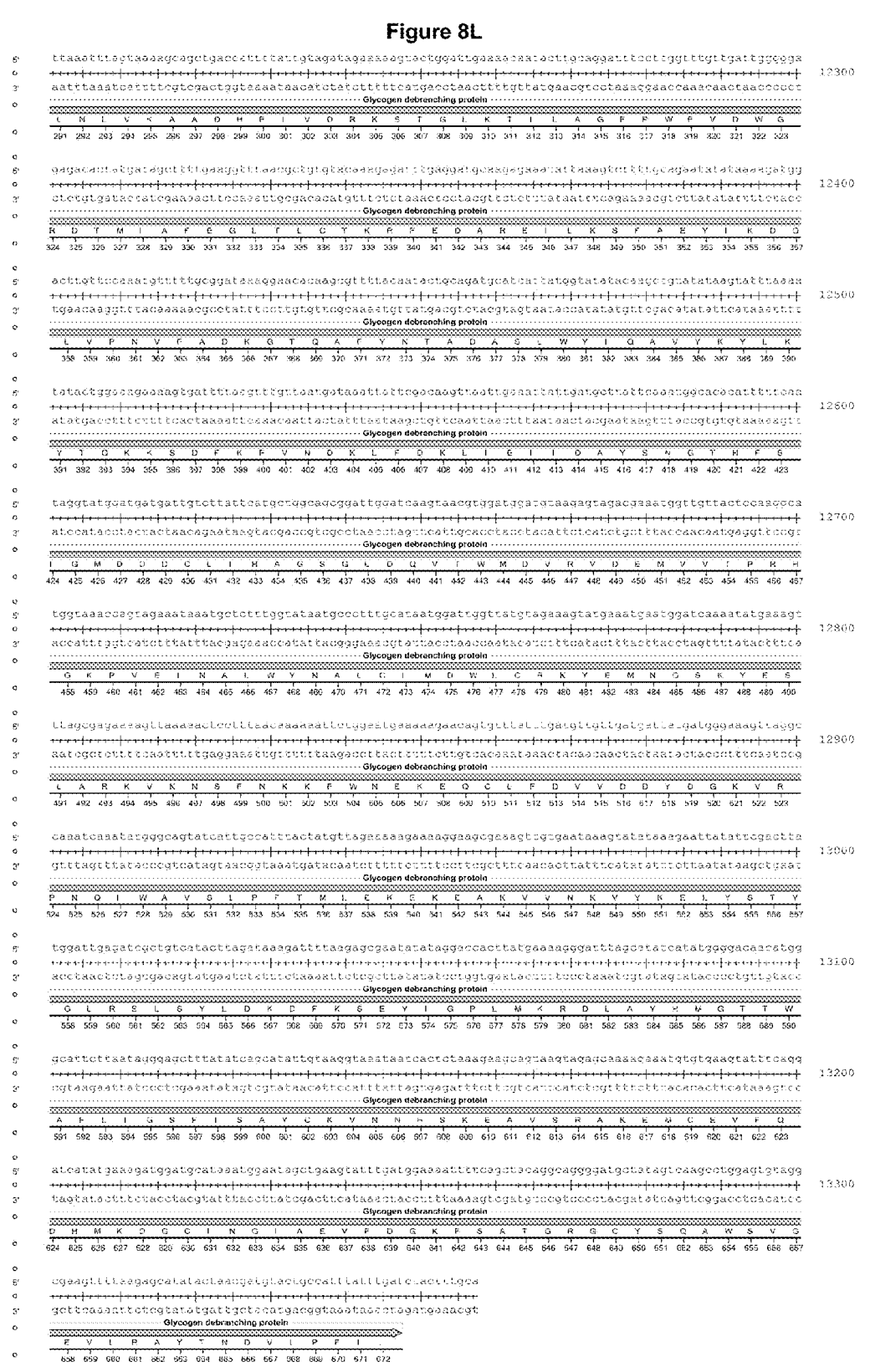

FIGS. 8A-8L. Starch metabolism operon from *C. saccharoperbutylacetonicum*, illustrating the location of the CGTase-encoding gene. The sense and anti-sense strand genomic sequences are SEQ ID NOs: 5 and 55, respectively. The SEQ ID NOs of the amino acid sequences are as follows: transcriptional regulator—SEQ ID NO: 47; maltose binding protein—SEQ ID NO: 48; isocyclomaltooligosaccharide—SEQ ID NO: 1; neopullanase—SEQ ID NO: 49; ABC transporters—SEQ ID NOs: 50 and 51; protein of unknown function—SEQ ID NO: 52; alpha amylase catalytic region—SEQ ID NO: 53; and glycogen debranching protein—SEQ ID NO: 54.

EXAMPLES

The present invention is further illustrated by the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims. The disclosure of each reference set forth herein is incorporated herein by reference in its entirety.

Example 1: Identification of Starch Hydrolytic Activity

Figure 1:
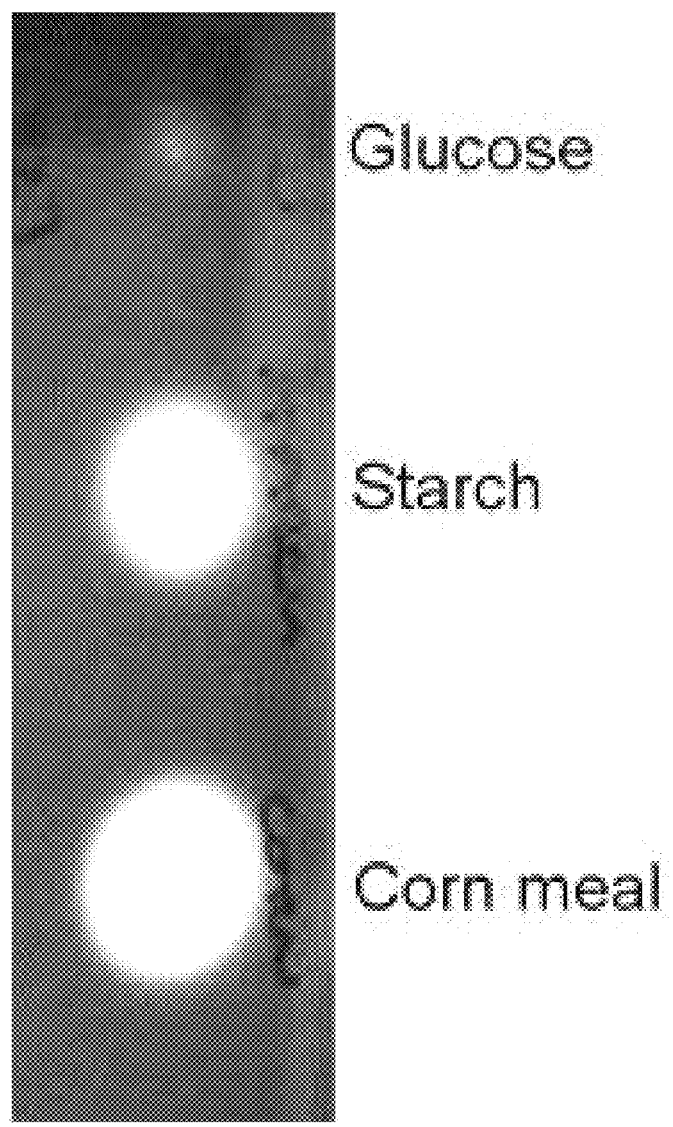
FIG. 1 shows starch plate onto which supernatant samples were spotted. Supernatant from *C. saccharoperbutylacetonicum* grown on glucose does not show any hydrolytic activity whereas supernatant from starch and corn does.

*C. saccharoperbutylacetonicum* was grown on various substrates. Supernatant samples were taken after 72 hours, concentrated and then spotted onto a starch plate. Supernatant from *C. saccharoperbutylacetonicum* grown on glucose does not show any hydrolytic activity, whereas supernatant from starch and corn does (FIG. 1).

Figure 2:
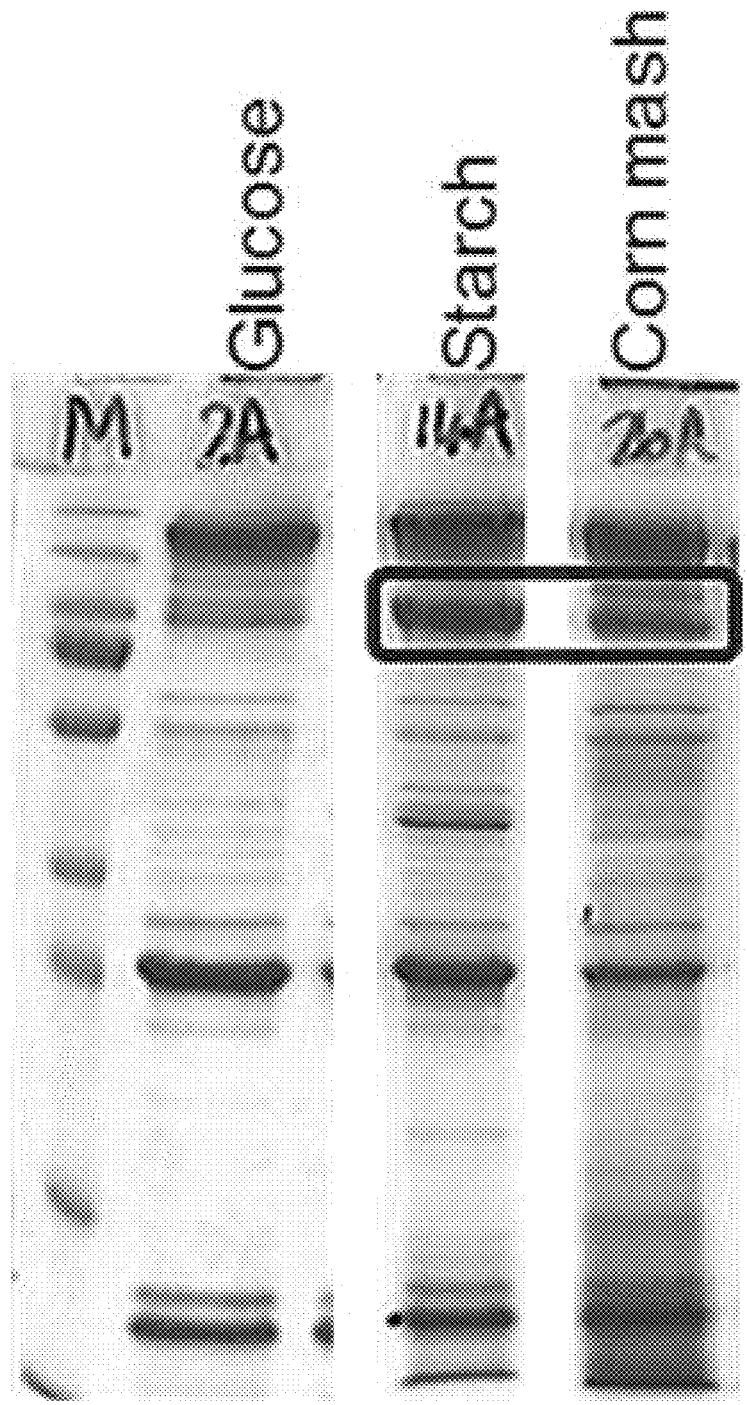
FIG. 2 shows *C. saccharoperbutylacetonicum* grown on glucose, starch or corn mash. Supernatants were concentrated and proteins analysed by 12.5% SDS-PAGE. The highlighted protein shows clear induction in starch and corn mash with no polypeptide in the glucose-grown sample.

These supernatant samples were also analysed by SDS-PAGE and an induced enzyme was identified (FIG. 2).

Example 2: Sequencing of the Novel Polypeptide

The induced peptide was excised from the SDS-PAGE gel and identified by mass spectrometry as being an isocyclomaltooligosaccharide glucanotransferase (CGTase).

Figure 3:
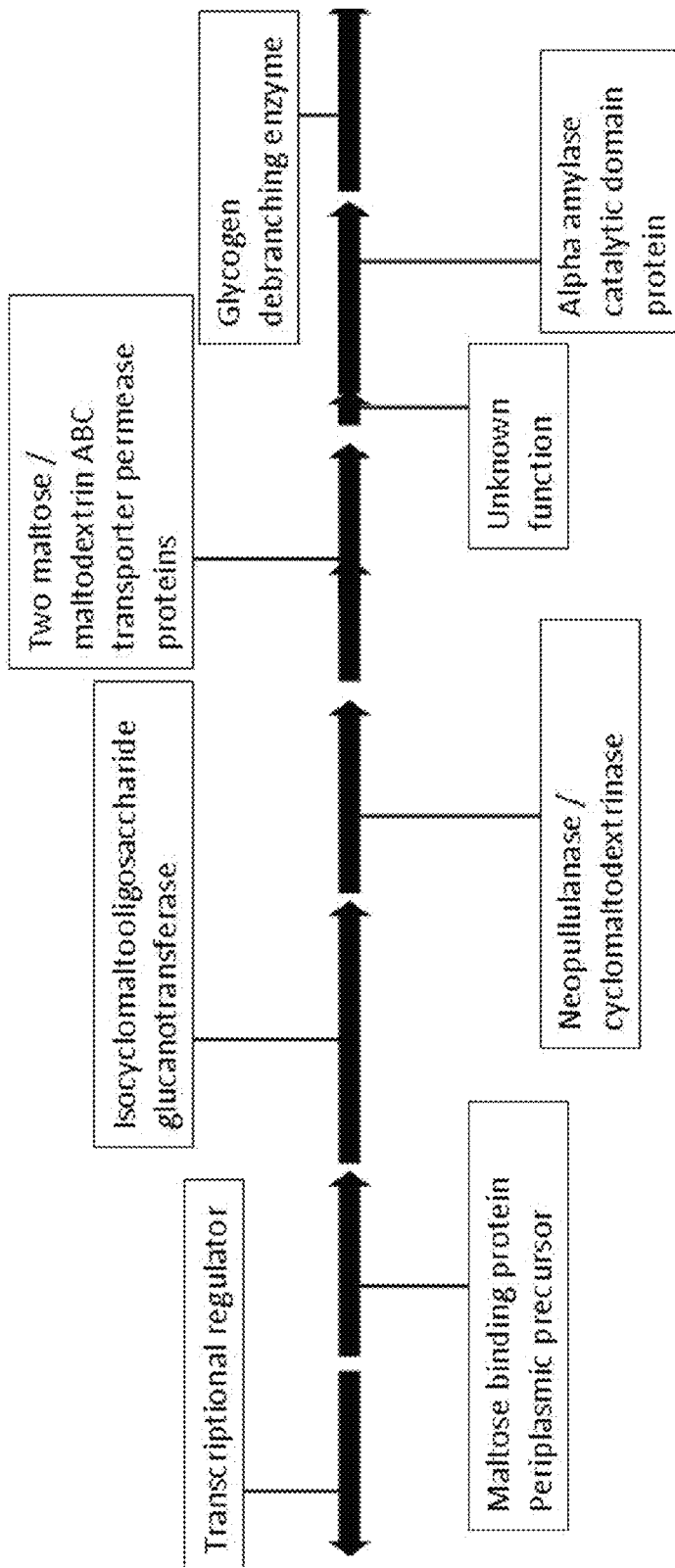
FIG. 3. The CGTase enzyme is located as the second gene in an operon in which the rest of the genes also appear to have a role in starch metabolism, from conversion to cyclodextrin through substrate uptake to internal conversion of the substrate, probably to glucose. Gene annotations are based on BLAST searches.

The portion of the *C. saccharoperbutylacetonicum* genome coding for the CGTase was sequenced. It was found that the CGTase is located within a starch metabolism operon (FIG. 3 and SEQ ID NO: 5).

The amino acid sequence of the CGTase from *C. saccharoperbutylacetonicum* N1-4(HMT) is given in SEQ ID NO: 1. The corresponding nucleic acid sequence is given in SEQ ID NO: 2.

The amino acid sequence of the CGTase from *C. saccharoperbutylacetonicum* N1-504 is given in SEQ ID NO: 3. The corresponding nucleic acid sequence is given in SEQ ID NO: 4.

Based on sequence alignments and homology searches, the CGTase from *C. saccharoperbutylacetonicum* appears to be a novel enzyme. A number of features make it different from the well-characterised α-, β-, and γ-CGTases for example, protein alignments show it clusters with CGTases from *B. circulans* and *Arthrobacter* which have been characterised and do not form the standard α-, β- or γ-cyclodextrins containing 6, 7 or 8 glucose units with α1-4 linkages (FIG. 4). Instead this class of CGTase enzymes appears to be much less conserved and converts starch to cyclodextrins containing 4, 5 or 6 glucose units with both α1-4 and α1-6 linkages. A key feature of these enzymes is a highly conserved residue required for efficient cyclisation. The α-, β-, and γ-CGTases all have tyr or phe at this position.

α-amylases have a small residue at this equivalent position, as do the CGTases from *B. circulans, Arthrobacter* and *C. saccharoperbutylacetonicum* (FIG. 5).

Based on these sequence comparisons, it is inferred that the CGTase from *C. saccharoperbutylacetonicum* does not convert starch through the well characterised α-, β-, γ-cyclodextrin route. Instead it appears to cyclise starch using a different mechanism.

Example 3: Initial Identification of Cyclodextrins

Proteins secreted into the supernatant during a *C. saccharoperbutylacetonicum* fermentation on a starch-based substrate were fractionated using ammonium sulphate cuts. The starch degradation activity was followed by spotting each fraction onto a starch plate and staining with iodine to detect zones of clearing. The fraction containing starch hydrolysis activity was added to a flask containing 10 g/L starch solution and incubated overnight at 35° C. in a shaking incubator. The starch solution was known to contain some linear dextrins.

In the morning, a mixture of starch and various starch hydrolysis products were detected in the flask, including linear- and cyclo-dextrins.

Example 4: Purification of Cyclodextrin

Figure 6:
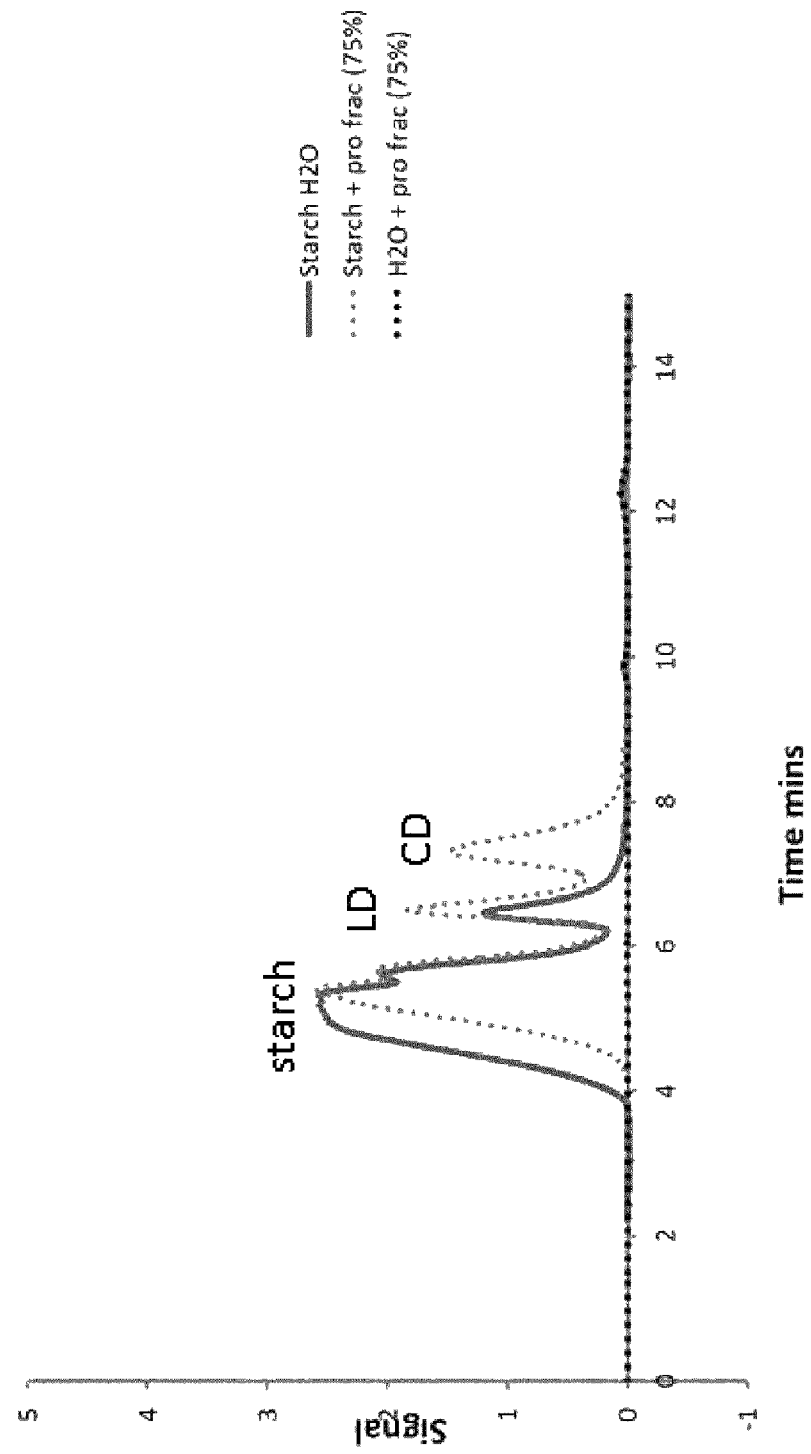
FIG. 6. The 75% fraction from ammonium sulphate cuts was found to have the most starch degradation activity so this was added to a starch solution to identify conversion products. Soluble starch already contains some linear dextrins (labelled LD). This peak increased in size and a new peak was also observed when the starch was treated with the 75% 'cut' (labelled CD).

The hydrolysis products from Example 3 were detected by HPLC. As shown in FIG. 6, various starch hydrolysis products were detected, including linear- and cyclo-dextrins.

The 75% ammonium sulphate 'cut' was also separated on an SDS-PAGE gel and the bands were isolated. Mass spectrometry was used to confirm the CGTase was still present in this fraction (data not shown).

The CGTase enzyme from *C. saccharoperbutylacetonicum* produced a cyclic dextrin with an elution profile which was different from known α-, β- and γ-cyclodextrins (FIG. 7). The elution profile was also clearly different to the elution profile one would expect to see if the strain was converting starch to dextrins and glucose using α-amylase and glucoamylase.

Furthermore, the cyclic compound was found to be relatively resistant to further hydrolysis by other amylases.

SEQUENCES

```
                                               SEQ ID NO: 1
C. saccharoperbutylacetonicum strain N1-4(HMT)
MFRRKFNKVILSILVATIVSSTNMFMSGSKAQAAIGNLSENDTIYQIMVD

RFYDGDKTNNATGDAFRNTENLEDDFRYMHGGDWQGVIDKLDYIKGMGYS

AIWISPVAEPQMWSRADGTGKVWPTAYHGYNVKDPNKANPYFGTKEKLKE

LVDKAHEKGIKVIIDIVPNHVGDYMLGKQAYYDIKGFEPAAPFNNPNWYH

HNGDIDWSREHSDPQMLDDHDLGGLDDLNQDNSDAKAAMNNAIKSWFDYT

GADAARVDAAKCMKPSYINELQKYIGVNTFGENFDMNVDFVKKWVGSDAE

WGMLDFPLYQAINNDFASGQSFDDMSSSGTCSIKNILAQDNKYNGYANHM

VTFIDNHDRNRFLTVANGNVKKLQNALVFMFTVRGVPTVFQGTEQNKGNA

NGASINGIADTWNRWSMVKKDYNGNVITDYFNENTDTYKLINKLNSFRQK

YEALREGTQREMWSSPHLYAFSRRMDSGENVGQEVVNVFNNSDGDQSATI

PIRAESTIKVGDKFVNLFDVNDSITVQQGGVTGKQISVNLGENSGKIYVV

NNETPNPDQKNVQYKVSYKNTNAQKVTLHYGTNGWKNIQDVNMTKNSNGE

FEATITVNNNDILNYCIHIISPTDYWDNNGGQNWNVKVTKAEDYINDGVK

SNLKSVNTTTSAAIDSGIDSTVNR
```

The predicted N-terminal signal sequence is highlighted (predicted using signalP).

```
                                               SEQ ID NO: 2
C. saccharoperbutylacetonicum strain N1-4(HMT)
ATGTTTAGAAGAAAATTTAACAAGGTAATATTATCTATCTTAGTTGCAAC

AATTGTTTCAAGCACTAACATGTTTATGAGTGGAAGCAAGGCACAAGCGG

CAATTGGAAATCTAAGTGAAAACGATACTATTTATCAAATTATGGTAGAC

AGATTTTATGATGGAGATAAAACAAATAATGCTACAGGAGATGCATTTCG

TAATACAGAAAATCTTGAAGATGATTTTAGATATATGCACGGCGGAGATT

GGCAAGGTGTTATTGATAAGTTAGATTATATTAAGGGCATGGGATACTCA

GCCATTTGGATATCACCGGTTGCGGAACCACAAATGTGGTCTAGAGCTGA

TGGCACAGGAAAAGTATGGCCTACAGCTTATCATGGATATAATGTGAAAG

ATCCCAATAAGGCAAATCCTTATTTTGGAACAAAAGAAAAGCTAAAGGAG

TTAGTAGATAAAGCTCACGAAAAGGGGATTAAAGTAATAATAGATATAGT

TCCAAATCATGTTGGGGATTATATGTTAGGAAAACAAGCTTATTATGACA

TCAAGGGGTTTGAGCCGGCAGCACCTTTTAATAATCCAAATTGGTATCAT

CATAATGGCGATATTGATTGGTCAAGAGAACACTCTGATCCCCAAATGTT

AGATGATCATGATTTGGGCGGTTTAGATGATTTAAATCAAGATAATTCTG

ATGCTAAGGCAGCTATGAATAATGCTATTAAGTCATGGTTTGATTATACT

GGAGCTGATGCAGCAAGGGTTGACGCAGCAAATGTATGAAACCATCTTA

TATTAACGAGTTACAAAAGTATATAGGAGTTAATACTTTTGGAGAAAATT

TTGATATGAATGTAGATTTTGTGAAGAAGTGGGTTGGATCCGATGCAGAA

TGGGGAATGCTAGATTTTCCATTATATCAAGCAATAAATAATGATTTTGC

ATCAGGACAATCTTTTGATGACATGTCATCATCAGGTACTTGCTCTATTA

AAAATATTTTAGCACAAGACAATAAATATAATGGTTATGCAAATCATATG

GTGACTTTTATAGATAATCATGATCGTAATAGATTTTTAACAGTAGCAAA

TGGTAATGTAAAAAAACTTCAAAATGCACTTGTTTTCATGTTTACTGTAA

GAGGGGTACCAACAGTATTTCAAGGTACAGAACAAAACAAAGGTAATGCA

AATGGAGCAAGTATAAATGGTATTGCAGATACATGGAATCGTTGGTCAAT

GGTTAAAAAGGATTACAATGGAAATGTAATTACAGATTATTTTAATGAGA

ATACAGATACTTATAAACTAATTAACAAATTGAATTCATTTAGGCAAAAA

TATGAAGCCTTAAGAGAAGGTACTCAAAGAGAAATGTGGTCTTCACCACA

TTTATATGCATTCTCAAGAAGGATGGATTCAGGAGAAATGTTGGACAAG

AAGTTGTAAATGTATTTAATAATTCAGATGGAGATCAAAGTGCGACCATT

CCAATTAGAGCTGAAAGTACTATAAAAGTTGGAGATAAATTTGTAAATCT

TTTTGATGTAAATGATTCGATCACAGTTCAACAAGGAGGTGTTACAGGAA

AACAAATATCAGTGAATTTAGGAGAAAATAGTGGGAAGATTTATGTTGTT
```

-continued

AATAATGAAACACCAAATCCAGATCAAAAGAACGTACAATATAAAGTTTC

ATATAAGAATACTAATGCACAAAAAGTAACACTTCATTATGGAACTAATG

GATGGAAAAACATTCAAGATGTAAATATGACTAAGAATTCCAATGGAGAA

TTTGAAGCAACTATTACAGTAAATAATAATGATATTCTAAATTACTGTAT

TCATATTATTTCACCAACAGACTATTGGGATAATAATGGTGGACAGAATT

GGAATGTAAAAGTGACTAAGGCAGAAGATTATATAAATGATGGTGTAAAG

AGTAATTTGAAGAGCGTTAATACAACTACATCAGCAGCTATAGACTCTGG

GATTGATAGTACTGTAAATCGTTAA

SEQ ID NO: 3
C. saccharoperbutylacetonicum strain N1-504
MFRRKFNKVILSILVATIVSSTNMFMSGSKAQAAIGNLSENDTIYQIMVD

RFYDGDKTNNATGDAFRNTENLEDDFRYMHGGDWQ

GVIDKLDYIKGMGYSAIWISPVAEPQMWSRADGTGKVWPTAYHGYNVKDP

-continued

NKANPYFGTKEKLKELVDKAHEKGIKVIIDIVPNHVGDYMLGKQAYYDIK

GFEPAAPFNNPNWYHHNGDIDWSREHSDPQMLDDHDLGGLDDLNQDNSDA

KAAMNNAIKSWFDYTGADAARVDAAKCMKPSYINELQKYIGVNTFGENFD

MNVDFVKKWVGSDAEWGMLDFPLYQAINNDFASGQSFDDMSSSGTCSIKN

ILAQDNKYNGYANHMVTFIDNHDRNRFLTVANGNVKKLQNALVFMFTVRG

VPTVFQGTEQNKGNGNGAILNGIADTWNRWSMVKKDYNGNIITDYFNENT

DTYKLISKLNSFRQKYEALREGTQREMWSSPHLYAFSRRMDSGENVGQEV

VNVFNNSDGDQSATIPIRAESTIKVGDKLVNLFDVNDSITVQQGGVTGKQ

ISVNLGENSGKIYVVNNETPNPDQKNVQYKVSYKNTNAQKVTLHYGTNGW

KNIQDVNMTKNSNGEFEATITVNNNDILNYCIHIISPTDYWDNNGGQNWN

VKVTKAEDYINDGVKSNLKSVNTTTSAAIESGIDSTVNR

The predicted N-terminal signal sequence is highlighted (predicted using signalP).

SEQ ID NO: 4
C. saccharoperbutylacetonicum strain N1-504
atgtttagaagaaaatttaacaaggtaatattatctattttagttgcaacaattgtttca agcactaacatgttt

ATGAGTGGAAGCAAGGCACAAGCGGCAATTGGAAATTTAAGTGAAAACGATACTATTTAT

CAAATTATGGTAGACAGATTTTATGATGGAGATAAAACAAATAATGCTACAGGAGATGCA

TTTCGTAATACAGAAAATCTTGAAGATGATTTTAGATATATGCACGGCGGAGATTGGCAA

GGTGTTATTGATAAGTTAGATTATATTAAGGGCATGGGATACTCAGCCATTTGGATATCA

CCGGTTGCGGAACCACAAATGTGGTCTAGAGCTGATGGCACAGGAAAAGTATGGCCTACA

GCTTACCATGGATATAATGTGAAAGATCCCAATAAGGCAAATCCTTATTTTGGAACAAAA

GAAAAGCTAAAGGAGTTAGTAGATAAAGCTCACGAAAAGGGGATTAAAGTAATAATAGAT

ATAGTTCCAAATCATGTTGGGGATTATATGTTAGGAAAACAAGCTTATTATGACATCAAG

GGGTTTGAGCCGGCAGCACCTTTTAATAATCCAAATTGGTATCATCATAATGGCGATATT

GATTGGTCAAGAGAACACTCTGATCCCCAAATGTTAGATGATCATGATTTGGGCGGTTTA

GATGATTTAAATCAAGATAATTCTGATGCTAAGGCAGCTATGAATAATGCTATTAAGTCA

TGGTTTGATTATACTGGAGCTGATGCAGCAAGGGTTGACGCAGCAAAATGTATGAAACCA

TCTTATATTAACGAGTTACAAAAGTATATAGGAGTTAATACTTTTGGAGAAAATTTTGAT

ATGAATGTAGATTTTGTGAAGAAGTGGGTTGGATCCGATGCAGAATGGGGAATGCTAGAT

TTTCCATTATATCAAGCAATAAATAATGATTTTGCATCAGGACAATCTTTTGATGACATG

TCATCATCAGGTACTTGCTCTATTAAAAATATTTTAGCACAAGACAATAAATATAATGGT

TATGCAAATCATATGGTGACTTTTATAGATAATCATGATCGTAATAGATTTTTAACAGTA

GCAAATGGTAATGTTAAAAAACTTCAAAATGCACTTGTTTTCATGTTTACTGTAAGAGGG

GTACCAACAGTATTTCAAGGTACAGAACAAAACAAAGGTAATGGAAATGGAGCAATTCTA

AATGGTATTGCAGATACATGGAATCGTTGGTCAATGGTTAAAAAGGACTATAATGGAAAT

ATAATTACAGATTATTTTAATGAGAATACAGATACTTATAAACTAATTAGCAAATTGAAT

TCATTTAGGCAAAAATATGAAGCCTTAAGAGAAGGTACTCAAAGAGAAATGTGGTCTTCA

CCACATTTATATGCATTCTCAAGAAGGATGGATTCAGGAGAAAATGTTGGACAAGAAGTT

GTAAATGTATTTAATAATTCAGATGGAGATCAAAGTGCGACCATTCCAATTAGAGCTGAA

-continued

```
AGTACTATAAAAGTTGGAGATAAACTTGTAAATCTTTTTGATGTAAATGATTCGATCACA

GTTCAACAAGGAGGTGTTACAGGAAAACAAATATCAGTGAATTTAGGAGAAAATAGTGGG

AAGATTTATGTTGTTAATAATGAAACACCAAATCCAGATCAAAAGAACGTACAATATAAA

GTTTCATATAAGAATACTAATGCACAAAAAGTAACACTTCATTATGGAACTAATGGATGG

AAAAACATTCAAGATGTAAATATGACTAAGAATTCCAATGGAGAATTTGAAGCAACTATT

ACAGTAAATAATAATGATATTCTAAATTACTGTATTCATATTATTTCACCAACAGACTAT

TGGGATAATAATGGTGGACAGAATTGGAATGTAAAAGTGACTAAGGCAGAAGATTATATA

AATGATGGTGTAAAGAGTAATTTGAAGAGCGTTAATACAACTACATCAGCAGCGATAGAA

TCTGGTATTGATAGTACTGTAAATCGTTAA
```

SEQ ID NO: 5
*C. saccharoperbutylacetonicum* strain N1-4(HMT)

```
gttcatggttttttcaataggctagattcacgtataagtaatttaggtgatattaggttatttca ttctgagaatttggattttgaattttttcattaaaatttcagctgccacttcaccaagtttaaat gtatctacatctagacaagttaaggatggagtggtgtaagcagaaaatggttcattgtcaaaagtc acaattccaatatctgtggggctatttaagccctttctttaagtgctttaagtacaccaaatgca acataattatttatgcatagtatggcatctatttcaggaaaatctgataataattgaagtgtaagt tcataaccacttccttgtctgagttgccttcttttatgtataaattattttagtaaaatttaat ttagaaagtatgtttttataaccaagaagccgattgaaagatattatttcatttgatttgccacca ataaaggctatattttataaccttgttctattaaatgacatgtggccagttctcctcctacagta ttattaacatcaacccagctggtactattcttaaattcctttggctgaccaataaggacataagga aagtttaaaccgttgagcttactaataatttccgaattgactattgaggtaggtattatgattcca tctacttttttactatatatcaatcgatttagaaattctgctttgcattctagtgaatttatgttt gatagggttaactcatagttattgattccaactatactttcaactccaccaataatattatagaaa aagaaatcaagaaaatattcctttctgctaatatctactagaagacctatattaaaactattctgg cgagctagctgccttgccgaattatttggaatatagttaagctcttttcataatgtttcttactttg agctttgtactttcagaaatagatttatgattatttataactttggataccgttgatttagataca tttgctgcgtgagctatatcatttatagtaacttttcatttttaactccttatgtgtgaaattgatt atttaaatattataaaacattatttgatttttttcgatatgtacattgttattaataatattacta tttattgtaaagtattttagaaatttttatacttctataagtttagcataataatctaaaaatac atatatagttgcacatttcagtgctaaagattaaatttatttatatcatctaaatcctcttaaact catttaaagttccttctctaaattgaaaaatgaatttccaattgtactcattgcataatttataga tttgttcacaagcataaagactattacctaaaatgtaggtattaagtgttataaacttatattta attttttcataagtcttttagcatatgccttaataaaacaatatatctggtggaagttaatacaat atattgaaattgattcaatattgcagtatactaaaatgagtaaaccggtttcttaaattttcaatg tatttaaagaatttgtaagacagaagaatataattttcaactttataatatgcttatttgaatgaa ttaataaaaagatgatttttagtattttgtttataagcctagtagttacaagaagtaaatattttc tgtaaaagattataaattaggagggagaattgaaaaatggtaaaaaaaataaagtattagcatca atcgtggcagcaactttagttgcaggaacatttgtaggatgtggaggaacaacagctacaagtaat aatgctaaagaaattacagtttggtcacatttgaaagaaaaagagattacagagcttactaaagta gcggaaaaatggggaagtgaaaagggagttaaggttaatgttgtagatgataaaggggagatgcaa gcatatatacaagccgctaatagttctaaaggtccagatatacttttggtgtacctaatgataac
```

-continued ttaggaacatttcaaaaagctggtttactttcagaagtgccaagtggttttatagatgagagtaaa
tatacatctaaacaagtaatagattcagtgactatagaaggaaaaaaatatgcagttccattagca
gctgaaactagtgctctattttataataaagataaagtttcagaagtaccaaaaactatggaagaa
gttgttgaattaggcaaaaaagtaggatttgaatacgatgtaactgatttatacagaagttatgga
tttttagcatcgcaaggtagctatattttaaaaataataatggaactgttgattcaaacgatatt
ggattaggcaatgaaggtgcgataaaaggatatcaattcattcaagatttaattgttaaagacaaa
ttaatgtctcaagatattactgatgatatagctaaagcagatttccaatcaggtaaatcagcattt
tatatttcaggaccatgggatatagaagcattttaaagattcaggaattaattttggtatagctcca
atgccaacattaggtgggaaaactgtttcaacattgatgggagttcaaactgcatttgtaagttca
aagtcacctaatcaagacttatcatgggagttaatgaagtatcttatggaaaatagtgatgaccta
atgattaagcaaggaaatagaattccagtttcaaaagcaggtatagaaagtgatgcgtttaaagcg
gccggaaacatggatgtatttgctaaacaattagaagttgctacagcaatgcctaatattccagaa
attcaaactacttggactccggtaaaaaataatataatatctttaataagcggatcaatggattcg
aaagaaactgcaaacaaatagtagatcaaattaaagaaggtataaagcaacaaaaataaaaaagt
aaattaagaaaataacatgtagtgctaaagtgattgaaacaattaactttagcatctttttaata
ttaatattttcaaaatacacaagccaaagaagttctctagctatatagtggagtttagtgtacat
tctatgtaattatattggtaaatgttttcagaaatgtattgaaatccatttaagatggtagtatac
taaatagggaaaccggtttacctaatgtaatacatttaaagaaataaaggaatgcgaagacgacga
tattttgattttatgtgcttattttgatgaaattatgacaaggtaattttataaaatcatttat
tagttttcataattatgtgaatgactaataaaaatatataatagtgggggaaagttatgtttaga
agaaaatttaacaaggtaatattatctatcttagttgcaacaattgtttcaagcactaacatgttt
atgagtggaagcaaggcacaagcggcaattggaaatctaagtgaaaacgatactatttatcaaatt
atggtagacagattttatgatggagataaaacaaataatgctacaggagatgcatttcgtaataca
gaaaatcttgaagatgattttagatatatgcacggcggagattggcaaggtgttattgataagtta
gattatattaagggcatgggatactcagccatttggatatcaccggttgcggaaccacaaatgtgg
tctagagctgatggcacaggaaaagtatggcctacagcttatcatggatataatgtgaaagatccc
aataaggcaaatccttattttggaacaaaagaaaagctaaaggagttagtagataaagctcacgaa
aaggggattaaagtaataatagatatagttccaaatcatgttggggattatatgttaggaaaacaa
gcttattatgacatcaaggggtttgagccggcagcaccttttaataatccaaattggtatcatcat
aatggcgatattgattggtcaagagaacactctgatccccaaatgttagatgatcatgatttgggc
ggtttagatgatttaaatcaagataattctgatgctaaggcagctatgaataatgctattaagtca
tggtttgattatactggagctgatgcagcaagggttgacgcagcaaaatgtatgaaaccatcttat
attaacgagttacaaaagtatataggagttaatacttttggagaaaattttgatatgaatgtagat
tttgtgaagaagtgggttggatccgatgcagaatggggaatgctagattttccattatatcaagca
ataaataatgattttgcatcaggacaatcttttgatgacatgtcatcatcaggtacttgctctatt
aaaaatattttagcacaagacaataaatataatggttatgcaaatcatatggtgacttttatagat
aatcatgatcgtaatagatttttaacagtagcaaatggtaatgtaaaaaaacttcaaaatgcactt
gttttcatgtttactgtaagaggggtaccaacagtatttcaaggtacagaacaaacaaaggtaat
gcaaatggagcaagtataaatggtattgcagatacatggaatcgttggtcaatggttaaaaaggat
tacaatggaaatgtaattacagattattttaatgagaatacagatacttataaactaattaacaaa
ttgaattcatttaggcaaaaatatgaagccttaagagaaggtactcaaagagaaatgtggtcttca -continued ccacatttatatgcattctcaagaaggatggattcaggagaaaatgttggacaagaagttgtaaat gtatttaataattcagatggagatcaaagtgcgaccattccaattagagctgaaagtactataaaa gttggagataaatttgtaaatcttttgatgtaaatgattcgatcacagttcaacaaggaggtgtt acaggaaaacaaatatcagtgaatttaggagaaaatagtgggaagatttatgttgttaataatgaa acaccaaatccagatcaaaagaacgtacaatataaagtttcatataagaatactaatgcacaaaaa gtaacacttcattatggaactaatggatggaaaaacattcaagatgtaaatatgactaagaattcc aatggagaatttgaagcaactattacagtaaataataatgatattctaaattactgtattcatatt atttcaccaacagactattgggataataatggtggacagaattggaatgtaaaagtgactaaggca gaagattatataaatgatggtgtaaagagtaatttgaagagcgttaatacaactacatcagcagct atagactctgggattgatagtactgtaaatcgttaaatataaatgttaatttaaagaaaaatttca tcatgcatattatatttggcacacaaaaatattaaatatctacttttcgcttctaaatggaaaaac cgcatggttagatcctaaagccttataaaatccatgtttccataattgaagcgaaatataggtaga taataatgtataaattaggaggaataattgatgaaaggtgaaataatatatcaaattttttccagac agatttaataaatcaagacaaaataataatgttgaaggtttaaaagaatgggaaagtgaagttgat ggacaatgtgttatgggaggtgatttaattggaattaaagagaaacttgattatctatcaaaactc ggtgttagtgcaatttatttaaatccaatttttcaggcaaattctaatcataagtatgatactgtt aactattataatatagatagttcttttggaactttagatgattttagagaattagtagattcatgt cataaaaaaaatataaaagttattattgatggagttttttaaccatactagcccagatttttttgct ttcaaagatatattagaaaatcaagaaagatcaaaatataaggattggtatactatttttagttat ccagttaaagtggaaagtccacctaattatagaaattttggaggatgtatagatatgccgcgtctt aatactgaaaatgttgaagttcaaaagtatatagttgatgttattaagtattgggaagggatgaaa atagatggattaagactagatgtaccatattatattgaagactctatgttagaaaaaataagaaaa tctactagcttatatatagtaggtgaaatatgggggtgtggcaagaaatttgtgcctcaatattt gatggagtaatgaattattcatttagagatttagtgcaaaaagcagttataagacaaagcattgat gcatcaatattcatagatgaatggaatttcatagaagaaacatacgggcagaatatacattgctgc tttaatatgtctggaagtcatgatacagaaaggattttttaatttctgcagaggagatataaagaga gaaaaattattctatgcattttattttattcccaggaatgcctcttgtatattatggagatgaa ataggtatgaaaggagaaaatgacccttattgtagaggaactatggaatggaatgaaagtaaatgg aattatgatatataatcatgtaaaaggtttaatagaacttagaaatagtagtgaagcattgcaa aaagggactatacaatttgttggacataaagaaatgatgtttgcatttgaaagagtgtatgcagaa aaaagagttaaagtatttatgaattttggacatagcaaacagtctattgatggatttgaactagat ggtcttagttataaagttatagtttagcattcaaggataactttgcaagttataaaatagcaactt taaacaatcaatgttctttaattggacattggttatcacaatatgtttatctgtttggataaatat atgaataaatttcattaatttttattttttccatgataaaaatcatagagaaaaggcatatatttt aaatttggctttattagtaaattcaattagtataatatattttagtgatattgacataagagatta aataaattatttatataaaaaagtaagattaagaaatactagatttaaatttttttatatcaaag aggtgggcaattatgaaacaagccaaaacaaaaaaataacacatactttgaaatcagtgccgtat ttattaccagccattatttcaataattatattttcaatattaccaatacttaatacaatatatttg gcatttacagactatactatgtattcacaaggaaaaattaattttgtaggaattgcaaattttaaa gaagtatttgctggtccatttaaagaagtattttttccggtatttatatggacatgtgtctttgct -continued acattggcaactgcaggaacattttgttaggactaattatggcaattcttgtaaataatgaaaat ataaaagaacgagggctttataaagcaattttaattattccatgggcattaccagctactgttgca atactttcatggcaaggtttattaaatggaagttatggggcaattaataatttacttataagtgta catgctatttcagcgcctattccatggttaactaatccattatgggcaagaattgcaataatcata gtaactatatggctaggatttccatatgccatgaatatttgtttgggttcacttcaatcgatacct aaaacatattatgaagcagctgacgttgatggagccagcaagtttgtaaaatttattaaaataact ttaccttcgcttgcacaaacagcatatccattagttatttcatcctttgcatttaactttaataat tttggtcaagcatatttaattactaatggtaatccggcaagacctggaacacaatttgcaggtttc acagatatattggcttcagtaaattataaattgtcaataacatttggaagatatgaaattgcttcc actataagcattattatatttataattttagctacaatttcatacatacaaatgaaagcatcagga caatttgaggaggttgattaaaatgacatcaaatgcaggaatttgaaattaaataatacagaagg acaaagtgaagaaatacaaaacataaaaattaaaatatgtaaaaaaattaagaccagcagaaataag aactgcatggatttcaaggatagtactttggattatgattgtaatagttcttattccaatcatggc agttgtttcagcatctatggctaaaggtaattcatttacgcaaacctctattttcctaaatcatt tactttagagaattatgtaaaagtaataactcaaactaagttttaatatgggcaagaaattcatt agttgtttgttttagcgttgctatgatgcagctaatcatgacaattccagcagcttttgcgttttc taagcttaggtttaaaggtagaaaatttggacttatgacacttttgatattacagatgtttccaaa tacaatggcattaccagcaattttaagtgttgcatataatattcggggtggaatggataatttatt accattaatattaattatatcagtaggtagtgcatataacatctggcttatgaagggatacatgga tggaattccaaaagaattaactgaaactgcatatatagatggagcaacaacttttcaagctttcat taaggtagtattgccactaataaagaatatgataatagtaatatttatatttgcttttgttggagc ttatagcgaattttatttacatcagctcttataaaagatcaatatacagaaactctagcaacagg tatgcaaggattcattaaagatcattttttcagctaactggactcaatattcagcggctgcaataat ggcatcattaccagttgttttgatatcagtattttcacaaaaaattctttgcaaaaggattaactgc tggatcagtaaaaggctaaagtggggacgtgagtatataatgaagccaactaaggattagaaaata agtagcaattttaataaaattaaaaagttttctataaaaatctttcaactaaagaaaattcaaaa aacaatgatgtaactattaaaaaatctaaaagtttgcattttaaattattggaaagtatgttctgt atttcaattattccaataataatttatttgcagcgttacttttattaaaattaattttattaagtaa tgttaattcataagctgaagatgtgaattcagaatcattgattttaaatgataaaagtaaggaatt atcgttagctatatctaatgtaaatgagactttaggcaagattgatcttggaactatagattctac aaataatttggaatctttagtgttaaatatggaggaggtatcaaatccaatgatcaaagtagcgta atagttatatataagtgaaaaggggaaggaattcttatgagattcgaagctgtatatcatagagcc tcagataacttatgttattcaattgataaagacaatttaattgtaaatataaagactggttatgat gtagaaaagtgtttatatattatggtgatccatttgatggaggaattttaggtggcgaatggaaa tggaaaggaaaagagaagaaattccatttaaaaagagattaaagcaccaaatggtggacaact actttgaaactgaagtataaaagatgtaaatactattttgaattaacggggaatgaagaaacctgg ttttattttgaagattgtttttttaagtgaaaaacaaatgcaattggacggaaaaatgttgcaatgt tttacatttccatggatgaatgaagctgatataaataaaacaccagcatgggtaaatgatatggtt tggtatcagatattcccagagcgttttgtaatggaaatccttcaattaatcccaagggggtccag ccttggcataaaggaggcgttacaaatgaagagttttatggtgggatttgcaggggataataaat aaattaaattatttaaaagaaataggaattacaggcatatatttaaatccaatattcgaatctccg -continued tcagcacataaatatgatacaactgattatatgaaaatagatcctaattttggagatgaaaatgta tttagaaagcttgtaaataaagcacatgaaaaagggattaggattatgcttgatggagtgtttaat cattgtggagctaagtttggaccatggttagatgtacttgaaaatggtcctagttccaaatattat agttggtttatggtaaataagtggccttttgatgataataatcacgatacaaaggatggacgattt tattcttttgcctttaatcagaaaatgccaaaattaaatacaaataatccagaagtaattgattat ttaattaaggtatgtgagtattgggtaaaaaattataagattgatggattaagattagatgttgca aatgaaatttcgcataagttctgtaagaagcttagagaaaaaatgaaatcgttaaatccagacttc tatattttaggtgaaatatggcatgattctattccttggcttagaggtgatgaatttgatgctatt atgaattattcactaactagtagtatatcagacttctggatagataagagtttaactaaggatgat tttgagtacacaataaatagatgctatacaatatatgcagcaaaataatgatgtgttatttaat ttgttggattctcatgatacagaacgcttaatttcaagagtaaaagacattaacgtattttatcaa cagctagctgtactatttacgatgccaggaagtccatgcatattttatggtacagaagttgcactt gaaggaaagtatgatcccgattgccgaagatgtatgccatgggatgaaataaaaagtggaatttat gatgataagattaatataatgaaggcgttgattaatttaagaaaagagcaaaaattatttagaagc cgtaattttcattttccaaatacaattaaaaatagcagggtaatagaatatattaaaatagatgaa aatgggaataggttagaaattttactaaattgttcaaatatagatgttttaatagagaataatggt agtgttttgtttagtaatttatattctaataatagactgcttaaaaaaggtgtattaattaggaag gttgattctatataaggttcaatcaaataaataacaagtccgtttacatcatgggctgataaaaaa tatccatttgcgatttgatttttatttataaatgaaaaagatatttaattaaatcagcaatatgta cttattaattataaatgaaaaaataattttgaagaggagtagtcatggaattaacatataggttcg gaagaggatactggagaaatataaaggaaggaaacgagagagaatggatgataggcaatggtattg gcgggtatagcagtcaaactatcattaatagtggatttagatgtcataatgggtatttaatagcag caatgaatccgccagtagaacgttattcaatattatatagaactcaggaaaaaatcgtcacagatg gaagaacatatgatttgacttgtcaggaatataaggattatacgaagaatggttatgagtatctca aaagttttatatttgattcagtgcctcaatatatttatcaaatagaagatataaatgtaaaaaaaa ctatagctatggaatatggatataatactgtagctatatgttatgagattgaaaatggaagttcta aggctaaaattgatattacaccactgtttaattttaaggaagctggtacatttaaggcttctgagc agctggattttaaaactgaattacaagacgatatattaaaattgtatcctaatgaagatgataaga agataataagttttatgtcatcagcaggcatatttaaggacagaagtcttataaaagtacagaatg attttaattataatccattaattgaagagaatcattactatgaatttgaaaatagaaatggattta ttgggttaaataatcattatacgccatatgatattgaaattgaattagagccttttgaaactaaaa agttttatttaaaatgtacagtagaagagttaggtgataaagacggatttgatattgttaaagaat ataaggaaagaacaaatgaattattgaatagatcaggctataaagatttttttgcattaaatttag taaaagcagctgaccatttattgtagatagaaaaagtactggattgaaaacaatacttgcaggat ttccttggtttgttgattgggggagagacactatgatagcttttgaaggtttaacgctgtgtacaa agagatttgaggatgcaagagaaatattaaagtcttttgcagaatatataaaagatggacttgttc caaatgttttgcggataaaggaacacaagcgttttacaatactgcagatgcatcattatggtata tacaagctgtatataagtatttaaaatatactggaaagaaaagtgattttaagtttgttaatgata aattattcgacaagttaattgaaattattgatgcttattcaaatggcacacattttcaataggta tggatgatgattgtcttattcatgctggcagcggattggatcaagtaacgtggatggatgtaagag -continued

```
tagacgaaatggttgttactccaaggcatggtaaaccagtagaaataaatgctctttggtataatg ccctttgcataatggattggttatgtagaaagtatgaaatgaatggatcaaaatatgaaagtttag cgagaaaagttaaaaactcctttaacaaaaaattctggaatgaaaaagaacagtgtttatttgatg ttgttgatgattatgatgggaaagttaggccaaatcaaatatgggcagtatcattgccatttacta tgttagaaaagaaaaggaagcgaaagttgtgaataaagtatataaagaattatattcgacttatg gattgagatcgctgtcatacttagataaagattttaagagcgaatatataggaccacttatgaaaa gggatttagcatatcatatggggacaacatgggcattcttaatagggagctttatatcagcatatt gtaaggtaaataatcactctaaagaagcagtaagtagagcaaaagaaatgtgtgaagtatttcagg atcatatgaaagatggatgcataaatggaatagctgaagtatttgatggaaaattttcagctacag gcagggatgctatagtcaagcctggagtgtaggcgaagttttaagagcatatactaacgatgtac tgccatttatttgatctactttgca
```

In the above sequence, the coding regions have been underlined and the start and stop codons have been highlighted.

---

What is claimed is:

1. A method of producing a solvent comprising the steps:
   (i) incubating a recombinant host cell comprising a heterologous nucleic acid molecule which is integrated into the host cell genome, wherein the nucleotide sequence of the heterologous nucleic acid molecule:
      (a) encodes the amino acid sequence set forth in SEQ ID NO: 1 or 3;
      (b) encodes a cyclodextrin glucanotransferase (CGTase) having at least 80% amino acid sequence identity with SEQ ID NO: 1 or 3;
      (c) is set forth in SEQ ID NO: 2 or 4; or
      (d) has at least 80% sequence identity with the nucleotide sequence set forth in SEQ ID NO: 2 or 4, and which encodes a CGTase,
   wherein the host cell is neither *Clostridium saccharoperbutylacetonicum* N1-4 (HMT) nor *Clostridium saccharoperbutylacetonicum* N1-504, with a polysaccharide substrate;
   wherein the host cell is capable of converting hydrolysed polysaccharide to an acid R—COOH, and wherein the host cell is further capable of converting the R—COOH into a solvent.

2. The method as claimed in claim 1, wherein the solvent is selected from the group consisting of acetone, ethanol and/or butanol.

3. The method as claimed in claim 1, wherein the host cell is a bacterial cell.

4. The method as claimed in claim 3, wherein the bacterial cell is of the genus *Clostridium* or *Bacillus*.

5. The method as claimed in claim 3, wherein the host cell is a biphasic bacteria.

6. The method as claimed in claim 4, wherein the host cell is selected from the group consisting of *C. acetobutylicum, C. aurantibutyricum, C. beijerinckii, C. thermocellum, C. thermobutyricum, C. pasteurianum, C. kluyveri, C. saccharobutylicum, C. thermosaccharolyticum, C. saccharolyticum, C. saccharoperbutylacetonicum, C. tyrobutyricum, C. butyricum, C. puniceum, C. diolis* and *C. roseum*; or the host cell is a Cluster I *Clostridia*.

7. A method of producing a solvent comprising the steps:
   (i) incubating a host cell comprising a nucleic acid molecule which is integrated into the host cell genome, wherein the nucleotide sequence of the nucleic acid molecule:
      (a) encodes the amino acid sequence set forth in SEQ ID NO: 1 or 3;
      (b) encodes a cyclodextrin glucanotransferase (CGTase) having at least 80% amino acid sequence identity with SEQ ID NO: 1 or 3;
      (c) is set forth in SEQ ID NO: 2 or 4; or
      (d) has at least 80% sequence identity with the nucleotide sequence set forth in SEQ ID NO: 2 or 4, and which encodes a CGTase,
   wherein the nucleic acid molecule is operably associated with a constitutive promoter, with a polysaccharide substrate;
   wherein the host cell is capable of converting hydrolysed polysaccharide to an acid R—COOH, and wherein the host cell is further capable of converting the R—COOH into a solvent.

8. The method as claimed in claim 7, wherein the solvent is selected from the group consisting of acetone, ethanol and/or butanol.

9. The method as claimed in claim 7, wherein the host cell is a bacterial cell.

10. The method as claimed in claim 9, wherein the bacterial cell is of the genus *Clostridium* or *Bacillus*.

11. The method as claimed in claim 9, wherein the host cell is a biphasic bacteria.

12. The method as claimed in claim 10, wherein the host cell is selected from the group consisting of *C. acetobutylicum, C. aurantibutyricum, C. beijerinckii, C. thermocellum, C. thermobutyricum, C. pasteurianum, C. kluyveri, C. saccharobutylicum, C. thermosaccharolyticum, C. saccharolyticum, C. saccharoperbutylacetonicum, C. tyrobutyricum, C. butyricum, C. puniceum, C. diolis* and *C. roseum*; or the host cell is a Cluster I *Clostridia*.

13. A method of producing a solvent comprising the steps:
   (i) incubating a host cell comprising two or more nucleic acid molecules which are integrated into the host cell genome, wherein the nucleotide sequence of the nucleic acid molecules:
      (a) encodes the amino acid sequence set forth in SEQ ID NO: 1 or 3;
      (b) encodes a cyclodextrin glucanotransferase (CGTase) having at least 80% amino acid sequence identity with SEQ ID NO: 1 or 3;
      (c) is set forth in SEQ ID NO: 2 or 4; or
      (d) has at least 80% sequence identity with the nucleotide sequence set forth in SEQ ID NO: 2 or 4, and which encodes a CGTase,
   with a polysaccharide substrate;
   wherein the host cell is capable of converting hydrolysed polysaccharide to an acid R—COOH, and wherein the host cell is further capable of converting the R—COOH into a solvent.

14. The method as claimed in claim 13, wherein the solvent is selected from the group consisting of acetone, ethanol and/or butanol.

15. The method as claimed in claim 13, wherein the host cell is a bacterial cell.

16. The method as claimed in claim 15, wherein the bacterial cell is of the genus *Clostridium* or *Bacillus*.

17. The method as claimed in claim 15, wherein the host cell is a biphasic bacteria.

18. The method as claimed in claim 16, wherein the host cell is selected from the group consisting of *C. acetobutylicum, C. aurantibutyricum, C. beijerinckii, C. thermocellum, C. thermobutyricum, C. pasteurianum, C. kluyveri, C. saccharobutylicum, C. thermosaccharolyticum, C. saccharolyticum, C. saccharoperbutylacetonicum, C. tyrobutyricum, C. butyricum, C. puniceum, C. diolis* and *C. roseum*; or the host cell is a Cluster I *Clostridia*.

* * * * *